US012752083B2

(12) United States Patent
Tran et al.

(10) Patent No.: US 12,752,083 B2
(45) Date of Patent: Oct. 6, 2026

(54) MAGNETIC TRAJECTORY PREDICTION AND POSITION IDENTIFICATION

(71) Applicant: Bard Access Systems, Inc., Salt Lake City, UT (US)

(72) Inventors: Huy Ngoc Tran, Riverton, UT (US); Jordan P. Diamond, Salt Lake City, UT (US); Paul T. Westwood, Kaysville, UT (US); Andrew J. Lengyel, Sandy, UT (US); Trevor Teerlink, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 766 days.

(21) Appl. No.: 17/484,868

(22) Filed: Sep. 24, 2021

(65) Prior Publication Data

US 2022/0096800 A1 Mar. 31, 2022

Related U.S. Application Data

(60) Provisional application No. 63/083,624, filed on Sep. 25, 2020.

(51) Int. Cl.

*A61M 25/00* (2006.01)
*A61M 25/01* (2006.01)
*G01R 33/28* (2006.01)

(52) U.S. Cl.

CPC .... *A61M 25/0158* (2013.01); *A61M 25/0127* (2013.01); *G01R 33/287* (2013.01); *A61M 2025/0166* (2013.01)

(58) Field of Classification Search

CPC ...... A61M 25/20158; A61M 25/20127; A61M 2025/0166; G01R 33/287
See application file for complete search history.

(56) References Cited

U.S. PATENT DOCUMENTS 2,619,515 A 11/1952 Doane
2,646,086 A 7/1953 Smith
(Continued)

FOREIGN PATENT DOCUMENTS

AU 642647 B2 10/1993
AU 706052 B2 6/1999
(Continued)

OTHER PUBLICATIONS

EP 10786978.6 filed Dec. 19, 2011 Office Action dated Jan. 16, 2019.
(Continued)

*Primary Examiner* — Keith M Raymond
*Assistant Examiner* — Adam D. Kolkin
(74) *Attorney, Agent, or Firm* — Rutan & Tucker LLP

(57) ABSTRACT

Embodiments disclosed herein are directed to trackable medical device, e.g. a catheter placement system, having a needle formed of a magnetizable material, and magnetized to produce a magnetic field having a magnetic field strength or a magnetic field signature detectable by a sensor of a tracking system. The medical device further includes a spring formed of a non-magnetizable material, e.g. silver coated copper beryllium or the like, and configured to display the same mechanical performance properties as a spring formed of the magnetizable material. Also disclosed is a method of tracking a medical device including magnetizing the catheter placement system to produce a magnetic field having a strength or a magnetic field signature and detecting the magnetic field by a sensor of a tracking system.

26 Claims, 9 Drawing Sheets

(56) References Cited

U.S. PATENT DOCUMENTS

| | | | |
|---|---|---|---|
| 3,133,244 | A | 5/1964 | Wojtulewicz |
| 3,297,020 | A | 1/1967 | Mathiesen |
| 3,625,200 | A | 12/1971 | Muller |
| 3,674,014 | A | 7/1972 | Tillander |
| 3,794,041 | A | 2/1974 | Frei et al. |
| 3,795,855 | A | 3/1974 | Browning |
| 3,817,241 | A | 6/1974 | Grausz |
| 3,847,157 | A | 11/1974 | Caillouette et al. |
| 3,868,565 | A | 2/1975 | Kuipers |
| 3,896,373 | A | 7/1975 | Zelby |
| 3,902,501 | A | 9/1975 | Citron et al. |
| 3,986,373 | A | 10/1976 | Goodlaxson |
| 3,995,623 | A | 12/1976 | Blake et al. |
| 4,003,369 | A | 1/1977 | Heilman et al. |
| 4,063,561 | A | 12/1977 | McKenna |
| 4,072,146 | A | 2/1978 | Howes |
| 4,092,867 | A | 6/1978 | Matzuk |
| 4,114,601 | A | 9/1978 | Abels |
| 4,149,535 | A | 4/1979 | Volder |
| 4,161,943 | A | 7/1979 | Nogier |
| 4,173,228 | A | 11/1979 | Van Steenwyk et al. |
| 4,175,566 | A | 11/1979 | Millar |
| 4,181,120 | A | 1/1980 | Kunii et al. |
| 4,224,949 | A | 9/1980 | Scott et al. |
| 4,244,362 | A | 1/1981 | Anderson |
| 4,289,139 | A | 9/1981 | Enjoji et al. |
| 4,317,078 | A | 2/1982 | Weed et al. |
| 4,327,722 | A | 5/1982 | Groshong et al. |
| 4,327,723 | A | 5/1982 | Frankhouser |
| 4,362,166 | A | 12/1982 | Furler et al. |
| 4,365,639 | A | 12/1982 | Goldreyer |
| 4,380,237 | A | 4/1983 | Newbower |
| 4,407,294 | A | 10/1983 | Vilkomerson |
| 4,417,886 | A | 11/1983 | Frankhouser et al. |
| 4,429,693 | A | 2/1984 | Blake et al. |
| 4,431,005 | A | 2/1984 | McCormick |
| 4,431,214 | A | 2/1984 | Buffington |
| 4,445,501 | A | 5/1984 | Bresler |
| 4,459,854 | A | 7/1984 | Richardson et al. |
| 4,469,106 | A | 9/1984 | Harui |
| 4,483,343 | A | 11/1984 | Beyer et al. |
| 4,491,137 | A | 1/1985 | Jingu |
| 4,565,201 | A | 1/1986 | Lass |
| 4,572,198 | A | 2/1986 | Codrington |
| 4,577,634 | A | 3/1986 | Gessman |
| 4,582,067 | A | 4/1986 | Silverstein et al. |
| 4,587,975 | A | 5/1986 | Salo et al. |
| 4,588,394 | A | 5/1986 | Schulte et al. |
| 4,593,687 | A | 6/1986 | Gray |
| 4,595,012 | A | 6/1986 | Webler et al. |
| 4,601,706 | A | 7/1986 | Aillon |
| 4,608,989 | A | 9/1986 | Drue |
| 4,608,992 | A | 9/1986 | Hakim et al. |
| 4,619,247 | A | 10/1986 | Inoue et al. |
| 4,622,644 | A | 11/1986 | Hansen |
| 4,644,960 | A | 2/1987 | Johans |
| 4,652,820 | A | 3/1987 | Maresca |
| 4,660,571 | A | 4/1987 | Hess et al. |
| 4,665,925 | A | 5/1987 | Millar |
| 4,667,230 | A | 5/1987 | Arakawa et al. |
| 4,674,518 | A | 6/1987 | Salo |
| 4,676,249 | A | 6/1987 | Arenas et al. |
| 4,681,106 | A | 7/1987 | Kensey et al. |
| 4,681,117 | A | 7/1987 | Brodman et al. |
| 4,688,578 | A | 8/1987 | Takano et al. |
| 4,692,148 | A | 9/1987 | Kantrowitz et al. |
| 4,697,595 | A | 10/1987 | Breyer et al. |
| 4,700,997 | A | 10/1987 | Strand |
| 4,706,681 | A | 11/1987 | Breyer et al. |
| 4,710,708 | A | 12/1987 | Rorden et al. |
| 4,733,669 | A | 3/1988 | Segal |
| 4,737,794 | A | 4/1988 | Jones |
| 4,741,356 | A | 5/1988 | Letzo et al. |
| 4,742,356 | A | 5/1988 | Kuipers |
| 4,753,247 | A | 6/1988 | Kirsner |
| 4,770,185 | A | 9/1988 | Silverstein et al. |
| 4,771,788 | A | 9/1988 | Millar |
| 4,781,685 | A | 11/1988 | Lehmann et al. |
| 4,784,646 | A | 11/1988 | Feingold |
| 4,787,070 | A | 11/1988 | Suzuki et al. |
| 4,787,396 | A | 11/1988 | Pidorenko |
| 4,790,809 | A | 12/1988 | Kuntz |
| 4,793,361 | A | 12/1988 | DuFault |
| 4,794,930 | A | 1/1989 | Machida et al. |
| 4,796,632 | A | 1/1989 | Boyd et al. |
| 4,798,588 | A | 1/1989 | Aillon |
| 4,798,598 | A | 1/1989 | Bonello et al. |
| 4,809,681 | A | 3/1989 | Kantrowitz et al. |
| 4,809,713 | A | 3/1989 | Grayzel |
| 4,813,729 | A | 3/1989 | Speckhart |
| 4,821,731 | A | 4/1989 | Martinelli et al. |
| 4,834,709 | A | 5/1989 | Banning et al. |
| 4,836,214 | A | 6/1989 | Sramek |
| 4,840,182 | A | 6/1989 | Carlson |
| 4,840,622 | A | 6/1989 | Hardy |
| 4,841,977 | A | 6/1989 | Griffith et al. |
| 4,849,692 | A | 7/1989 | Blood |
| 4,850,358 | A | 7/1989 | Millar |
| 4,852,580 | A | 8/1989 | Wood |
| 4,856,317 | A | 8/1989 | Pidorenko et al. |
| 4,856,529 | A | 8/1989 | Segal |
| 4,860,757 | A | 8/1989 | Lynch et al. |
| 4,867,169 | A | 9/1989 | Machida et al. |
| 4,869,263 | A | 9/1989 | Segal et al. |
| 4,869,718 | A | 9/1989 | Brader |
| 4,873,987 | A | 10/1989 | Djordjevich et al. |
| 4,887,606 | A | 12/1989 | Yock et al. |
| 4,887,615 | A | 12/1989 | Taylor |
| 4,889,128 | A | 12/1989 | Millar |
| 4,899,756 | A | 2/1990 | Sonek |
| 4,901,725 | A | 2/1990 | Nappholz et al. |
| 4,905,698 | A | 3/1990 | Strohl, Jr. et al. |
| 4,911,173 | A | 3/1990 | Terwilliger |
| 4,911,174 | A | 3/1990 | Pederson et al. |
| 4,917,669 | A | 4/1990 | Bonaldo |
| 4,924,870 | A | 5/1990 | Wlodarczyk et al. |
| 4,943,770 | A | 7/1990 | Ashley-Rollman et al. |
| 4,945,305 | A | 7/1990 | Blood |
| 4,947,852 | A | 8/1990 | Nassi et al. |
| 4,957,110 | A | 9/1990 | Vogel et al. |
| 4,957,111 | A | 9/1990 | Millar |
| 4,961,433 | A | 10/1990 | Christian |
| 4,966,148 | A | 10/1990 | Millar |
| 4,967,753 | A | 11/1990 | Haase et al. |
| 4,977,886 | A | 12/1990 | Takehana et al. |
| 4,989,608 | A | 2/1991 | Ratner |
| 4,989,610 | A | 2/1991 | Patton et al. |
| 4,995,396 | A | 2/1991 | Inaba et al. |
| 4,998,916 | A | 3/1991 | Hammerslag et al. |
| 5,004,456 | A | 4/1991 | Botterbusch et al. |
| 5,005,592 | A | 4/1991 | Cartmell |
| 5,016,173 | A | 5/1991 | Kenet et al. |
| 5,025,799 | A | 6/1991 | Wilson |
| 5,029,585 | A | 7/1991 | Lieber et al. |
| 5,040,548 | A | 8/1991 | Yock |
| 5,042,486 | A | 8/1991 | Pfeiler et al. |
| 5,045,071 | A | 9/1991 | McCormick et al. |
| 5,046,497 | A | 9/1991 | Millar |
| 5,050,607 | A | 9/1991 | Bradley et al. |
| 5,055,813 | A | 10/1991 | Johnson |
| 5,057,095 | A | 10/1991 | Fabian |
| 5,058,583 | A | 10/1991 | Geddes et al. |
| 5,058,595 | A | 10/1991 | Kern |
| 5,067,489 | A | 11/1991 | Lind |
| 5,076,278 | A | 12/1991 | Vilkomerson et al. |
| 5,078,140 | A | 1/1992 | Kwoh |
| 5,078,148 | A | 1/1992 | Nassi et al. |
| 5,078,149 | A | 1/1992 | Katsumata et al. |
| 5,078,678 | A | 1/1992 | Katims |
| 5,078,714 | A | 1/1992 | Katims |
| 5,084,022 | A | 1/1992 | Claude |
| 5,090,418 | A | 2/1992 | Squires et al. |
| 5,092,341 | A | 3/1992 | Kelen |
| 5,099,845 | A | 3/1992 | Besz et al. |

(56) References Cited

U.S. PATENT DOCUMENTS 5,099,850 A 3/1992 Matsui et al.
5,100,387 A 3/1992 Ng
5,105,829 A 4/1992 Fabian et al.
5,109,862 A 5/1992 Kelen et al.
5,114,401 A 5/1992 Stuart et al.
5,121,750 A 6/1992 Katims
5,125,410 A 6/1992 Misono et al.
5,134,370 A 7/1992 Jefferts et al.
5,144,955 A 9/1992 O'Hara
5,146,151 A 9/1992 Korn
5,148,809 A 9/1992 Biegeleisen-Knight et al.
5,156,151 A 10/1992 Imran
5,158,086 A 10/1992 Brown et al.
5,160,342 A 11/1992 Reger et al.
5,161,536 A 11/1992 Vilkomerson et al.
5,174,295 A 12/1992 Christian et al.
5,174,299 A 12/1992 Nelson
5,181,513 A 1/1993 Touboul et al.
5,184,601 A 2/1993 Putman
5,184,627 A 2/1993 de Toledo
5,190,045 A 3/1993 Frazin
5,202,985 A 4/1993 Goyal
5,205,830 A 4/1993 Dassa et al.
5,211,165 A 5/1993 Dumoulin et al.
5,211,636 A 5/1993 Mische
5,212,988 A 5/1993 White et al.
5,214,615 A 5/1993 Bauer
5,217,026 A 6/1993 Stoy et al.
5,220,924 A 6/1993 Frazin
5,233,994 A 8/1993 Shmulewitz
5,235,987 A 8/1993 Wolfe
5,239,464 A 8/1993 Blair et al.
5,240,004 A 8/1993 Walinsky et al.
5,243,995 A 9/1993 Maier
5,246,007 A 9/1993 Frisbie et al.
5,246,426 A 9/1993 Lewis et al.
5,247,171 A 9/1993 Wlodarczyk et al.
5,251,635 A 10/1993 Dumoulin et al.
5,255,680 A 10/1993 Darrow et al.
5,257,636 A 11/1993 White
5,257,979 A 11/1993 Jagpal
5,261,409 A 11/1993 Dardel
5,265,610 A 11/1993 Darrow et al.
5,265,614 A 11/1993 Hayakawa et al.
5,267,569 A 12/1993 Lienhard
5,269,306 A 12/1993 Warnking et al.
5,269,759 A 12/1993 Hernandez et al.
5,270,810 A 12/1993 Nishimura
5,271,404 A 12/1993 Corl et al.
5,273,025 A 12/1993 Sakiyama et al.
5,273,042 A 12/1993 Lynch et al.
5,274,551 A 12/1993 Corby, Jr.
5,275,053 A 1/1994 Wlodarczyk et al.
5,279,129 A 1/1994 Ito
5,279,607 A 1/1994 Schentag et al.
5,280,786 A 1/1994 Wlodarczyk et al.
5,287,331 A 2/1994 Schindel et al.
5,289,373 A 2/1994 Zarge et al.
5,292,342 A 3/1994 Nelson et al.
5,307,072 A 4/1994 Jones, Jr.
5,311,871 A 5/1994 Yock
5,313,949 A 5/1994 Yock
5,318,025 A 6/1994 Dumoulin et al.
5,325,293 A 6/1994 Dorne
5,325,860 A 7/1994 Seward et al.
5,325,873 A 7/1994 Hirschi et al.
5,330,496 A 7/1994 Alferness
5,331,491 A 7/1994 Hayakawa et al.
5,331,966 A 7/1994 Bennett et al.
5,333,614 A 8/1994 Feiring
5,337,678 A 8/1994 Grout
5,341,807 A 8/1994 Nardella
5,343,865 A 9/1994 Gardineer et al.
5,345,940 A 9/1994 Seward et al.
5,348,020 A 9/1994 Hutson
5,350,352 A 9/1994 Buchholtz et al.
5,357,961 A 10/1994 Fields et al.
5,365,935 A 11/1994 Righter et al.
5,366,443 A 11/1994 Eggers et al.
5,368,048 A 11/1994 Stoy et al.
5,375,596 A 12/1994 Twiss et al.
5,376,083 A 12/1994 Mische
5,377,678 A 1/1995 Dumoulin et al.
5,385,053 A 1/1995 Wlodarczyk et al.
5,385,146 A 1/1995 Goldreyer
5,391,199 A 2/1995 Ben-Haim
5,394,876 A 3/1995 Ma
5,394,877 A 3/1995 Orr et al.
5,395,366 A 3/1995 D'Andrea et al.
5,398,683 A 3/1995 Edwards et al.
5,398,691 A 3/1995 Martin et al.
5,411,485 A 5/1995 Tennican et al.
5,413,107 A 5/1995 Oakley et al.
5,417,208 A 5/1995 Winkler
5,417,701 A 5/1995 Holmes
5,422,478 A 6/1995 Wlodarczyk et al.
5,423,334 A 6/1995 Jordan
5,423,877 A 6/1995 Mackey
5,425,367 A 6/1995 Shapiro et al.
5,425,370 A 6/1995 Vilkomerson
5,425,382 A 6/1995 Golden et al.
5,427,114 A 6/1995 Colliver et al.
5,429,132 A 7/1995 Guy et al.
5,429,617 A 7/1995 Hammersmark et al.
5,431,641 A 7/1995 Grozinger et al.
5,433,729 A 7/1995 Adams et al.
5,437,276 A 8/1995 Takada
5,437,277 A 8/1995 Dumoulin et al.
5,438,873 A 8/1995 Wlodarczyk et al.
5,441,052 A 8/1995 Miyajima
5,443,066 A 8/1995 Dumoulin et al.
5,443,489 A 8/1995 Ben-Haim
5,445,150 A 8/1995 Dumoulin et al.
5,445,166 A 8/1995 Taylor
5,450,846 A 9/1995 Goldreyer
5,453,575 A 9/1995 O'Donnell et al.
5,453,576 A 9/1995 Krivitski
5,456,256 A 10/1995 Schneider et al.
5,456,718 A 10/1995 Szymaitis
5,464,016 A 11/1995 Nicholas et al.
5,474,065 A 12/1995 Meathrel et al.
5,476,090 A 12/1995 Kishi
5,480,409 A * 1/1996 Riza .................. A61B 17/2909
606/208
5,480,422 A 1/1996 Ben-Haim
5,487,729 A 1/1996 Avellanet et al.
5,490,522 A 2/1996 Dardel
5,492,538 A 2/1996 Johlin, Jr.
5,494,038 A 2/1996 Wang et al.
5,500,011 A 3/1996 Desai
5,500,012 A 3/1996 Brucker et al.
5,505,205 A 4/1996 Solomon et al.
5,509,822 A 4/1996 Negus et al.
5,513,637 A 5/1996 Twiss et al.
5,515,160 A 5/1996 Schulz et al.
5,515,853 A 5/1996 Smith et al.
5,517,989 A 5/1996 Frisbie et al.
5,522,878 A 6/1996 Montecalvo et al.
5,522,880 A 6/1996 Barone et al.
5,526,812 A 6/1996 Dumoulin et al.
5,531,664 A 7/1996 Adachi et al.
5,536,248 A 7/1996 Weaver et al.
5,540,230 A 7/1996 Vilkomerson
5,540,681 A 7/1996 Strul et al.
5,542,938 A 8/1996 Avellanet et al.
5,546,949 A 8/1996 Frazin et al.
5,546,951 A 8/1996 Ben-Haim
5,555,618 A 9/1996 Winkler
5,558,091 A 9/1996 Acker et al.
5,568,809 A 10/1996 Ben-Haim
D375,450 S 11/1996 Bidwell et al.
5,570,671 A 11/1996 Hickey
5,575,291 A 11/1996 Hayakawa et al.
5,588,442 A 12/1996 Scovil et al.

(56) References Cited

U.S. PATENT DOCUMENTS

| | | | |
|---|---|---|---|
| 5,592,939 | A | 1/1997 | Martinelli |
| 5,598,846 | A | 2/1997 | Peszynski |
| 5,599,299 | A | 2/1997 | Weaver et al. |
| 5,600,330 | A | 2/1997 | Blood |
| 5,603,333 | A | 2/1997 | Konings |
| 5,606,981 | A | 3/1997 | Tartacower et al. |
| 5,610,967 | A | 3/1997 | Moorman et al. |
| 5,617,866 | A | 4/1997 | Marian, Jr. |
| 5,622,169 | A | 4/1997 | Golden et al. |
| 5,622,170 | A | 4/1997 | Schulz |
| 5,622,184 | A | 4/1997 | Ashby et al. |
| 5,623,931 | A | 4/1997 | Wung et al. |
| 5,624,430 | A | 4/1997 | Eton et al. |
| 5,626,554 | A | 5/1997 | Ryaby et al. |
| 5,626,870 | A | 5/1997 | Monshipouri et al. |
| 5,630,419 | A | 5/1997 | Ranalletta |
| 5,638,819 | A | 6/1997 | Manwaring et al. |
| 5,640,967 | A | 6/1997 | Fine et al. |
| 5,644,612 | A | 7/1997 | Moorman et al. |
| 5,645,065 | A | 7/1997 | Shapiro et al. |
| 5,651,047 | A | 7/1997 | Moorman et al. |
| 5,654,864 | A | 8/1997 | Ritter et al. |
| D383,968 | S | 9/1997 | Bidwell et al. |
| 5,662,115 | A | 9/1997 | Torp et al. |
| 5,665,103 | A | 9/1997 | Lafontaine et al. |
| 5,665,477 | A | 9/1997 | Meathrel et al. |
| 5,666,473 | A | 9/1997 | Wallace |
| 5,666,958 | A | 9/1997 | Rothenberg et al. |
| 5,669,383 | A | 9/1997 | Johnson |
| 5,669,388 | A | 9/1997 | Vilkomerson |
| 5,676,159 | A | 10/1997 | Navis |
| 5,676,673 | A | 10/1997 | Ferre et al. |
| 5,682,890 | A | 11/1997 | Kormos et al. |
| 5,691,898 | A | 11/1997 | Rosenberg et al. |
| 5,694,945 | A | 12/1997 | Ben-Haim |
| 5,695,479 | A | 12/1997 | Jagpal |
| 5,697,377 | A | 12/1997 | Wittkampf |
| 5,699,801 | A | 12/1997 | Atalar et al. |
| 5,700,889 | A | 12/1997 | Blair |
| 5,701,898 | A | 12/1997 | Adam et al. |
| 5,702,433 | A | 12/1997 | Taylor et al. |
| 5,711,299 | A | 1/1998 | Manwaring et al. |
| 5,713,362 | A | 2/1998 | Vilkomerson |
| 5,713,363 | A | 2/1998 | Seward et al. |
| 5,713,858 | A | 2/1998 | Heruth et al. |
| 5,713,946 | A | 2/1998 | Ben-Haim |
| 5,715,817 | A | 2/1998 | Stevens-Wright et al. |
| 5,716,389 | A | 2/1998 | Walinsky et al. |
| 5,718,241 | A | 2/1998 | Ben-Haim et al. |
| D391,838 | S | 3/1998 | Bidwell et al. |
| 5,722,412 | A | 3/1998 | Pflugrath et al. |
| 5,727,550 | A | 3/1998 | Montecalvo |
| 5,727,552 | A | 3/1998 | Ryan |
| 5,727,553 | A | 3/1998 | Saad |
| 5,729,055 | A | 3/1998 | Manning |
| 5,729,129 | A | 3/1998 | Acker |
| 5,729,584 | A | 3/1998 | Moorman et al. |
| 5,730,129 | A | 3/1998 | Darrow et al. |
| 5,731,996 | A | 3/1998 | Gilbert |
| 5,733,323 | A | 3/1998 | Buck et al. |
| 5,738,096 | A | 4/1998 | Ben-Haim |
| 5,740,808 | A | 4/1998 | Panescu et al. |
| 5,742,394 | A | 4/1998 | Hansen |
| 5,744,953 | A | 4/1998 | Hansen |
| 5,748,767 | A | 5/1998 | Raab |
| 5,749,835 | A | 5/1998 | Glantz |
| 5,749,938 | A | 5/1998 | Coombs |
| 5,751,785 | A | 5/1998 | Moorman et al. |
| 5,752,513 | A | 5/1998 | Acker et al. |
| 5,758,650 | A | 6/1998 | Miller et al. |
| 5,762,064 | A | 6/1998 | Polvani |
| 5,767,669 | A | 6/1998 | Hansen et al. |
| 5,767,960 | A | 6/1998 | Orman |
| 5,769,786 | A | 6/1998 | Wiegel |
| 5,769,843 | A | 6/1998 | Abela et al. |
| 5,769,881 | A | 6/1998 | Schroeppel et al. |
| 5,771,896 | A | 6/1998 | Sliwa, Jr. et al. |
| 5,775,322 | A | 7/1998 | Silverstein et al. |
| 5,775,332 | A | 7/1998 | Goldman |
| 5,776,064 | A | 7/1998 | Kalfas et al. |
| 5,776,080 | A | 7/1998 | Thome et al. |
| 5,779,638 | A | 7/1998 | Vesely et al. |
| 5,782,767 | A | 7/1998 | Pretlow, III |
| 5,782,773 | A | 7/1998 | Kuo et al. |
| 5,785,657 | A | 7/1998 | Breyer et al. |
| 5,792,055 | A | 8/1998 | McKinnon |
| 5,795,297 | A | 8/1998 | Daigle |
| 5,795,298 | A | 8/1998 | Vesely et al. |
| 5,795,632 | A | 8/1998 | Buchalter |
| 5,797,849 | A | 8/1998 | Vesely et al. |
| 5,800,352 | A | 9/1998 | Ferre et al. |
| 5,800,410 | A | 9/1998 | Gawreluk |
| 5,800,497 | A | 9/1998 | Bakels et al. |
| 5,803,089 | A | 9/1998 | Ferre et al. |
| 5,810,733 | A | 9/1998 | Van Creveld et al. |
| RE35,924 | E | 10/1998 | Winkler |
| 5,817,022 | A | 10/1998 | Vesely |
| 5,817,024 | A | 10/1998 | Ogle et al. |
| 5,820,549 | A | 10/1998 | Marian, Jr. |
| 5,820,560 | A | 10/1998 | Sinderby et al. |
| 5,824,031 | A | 10/1998 | Cookston et al. |
| 5,827,192 | A | 10/1998 | Gopakumaran et al. |
| 5,829,444 | A | 11/1998 | Ferre et al. |
| 5,830,145 | A | 11/1998 | Tenhoff |
| 5,831,260 | A | 11/1998 | Hansen |
| 5,833,608 | A | 11/1998 | Acker |
| 5,833,622 | A | 11/1998 | Meathrel et al. |
| 5,835,561 | A | 11/1998 | Moorman et al. |
| 5,836,882 | A | 11/1998 | Frazin |
| 5,836,990 | A | 11/1998 | Li |
| 5,840,024 | A | 11/1998 | Taniguchi et al. |
| 5,840,025 | A | 11/1998 | Ben-Haim |
| 5,840,030 | A | 11/1998 | Ferek-Petric et al. |
| 5,840,031 | A | 11/1998 | Crowley |
| 5,842,986 | A | 12/1998 | Avrin et al. |
| 5,842,998 | A | 12/1998 | Gopakumaran et al. |
| 5,843,076 | A | 12/1998 | Webster, Jr. et al. |
| 5,843,153 | A | 12/1998 | Johnston et al. |
| 5,844,140 | A | 12/1998 | Seale |
| 5,846,198 | A | 12/1998 | Killmann |
| 5,851,218 | A | 12/1998 | Lev |
| 5,855,553 | A | 1/1999 | Tajima et al. |
| 5,859,893 | A | 1/1999 | Moorman et al. |
| 5,865,748 | A | 2/1999 | Co et al. |
| 5,868,673 | A | 2/1999 | Vesely |
| 5,873,822 | A | 2/1999 | Ferre et al. |
| 5,876,328 | A | 3/1999 | Fox et al. |
| 5,879,297 | A | 3/1999 | Haynor et al. |
| 5,893,363 | A | 4/1999 | Little et al. |
| 5,897,495 | A | 4/1999 | Aida et al. |
| 5,899,860 | A | 5/1999 | Pfeiffer et al. |
| 5,902,238 | A | 5/1999 | Golden et al. |
| 5,907,487 | A | 5/1999 | Rosenberg et al. |
| 5,908,385 | A | 6/1999 | Chechelski et al. |
| 5,908,387 | A | 6/1999 | LeFree et al. |
| 5,910,113 | A | 6/1999 | Pruter |
| 5,910,120 | A | 6/1999 | Kim et al. |
| 5,913,820 | A | 6/1999 | Bladen et al. |
| 5,913,830 | A | 6/1999 | Miles |
| 5,919,141 | A | 7/1999 | Money et al. |
| 5,919,170 | A | 7/1999 | Woessner |
| 5,928,145 | A | 7/1999 | Ocali et al. |
| 5,929,607 | A | 7/1999 | Rosenberg et al. |
| 5,931,788 | A | 8/1999 | Keen et al. |
| 5,931,818 | A | 8/1999 | Werp et al. |
| 5,931,863 | A | 8/1999 | Griffin, III et al. |
| 5,935,160 | A | 8/1999 | Auricchio et al. |
| 5,941,858 | A | 8/1999 | Johnson |
| 5,941,889 | A | 8/1999 | Cermak |
| 5,941,904 | A | 8/1999 | Johnston et al. |
| 5,944,022 | A | 8/1999 | Nardella et al. |
| 5,944,023 | A | 8/1999 | Johnson et al. |
| 5,951,472 | A | 9/1999 | Van Vaals et al. |
| 5,951,598 | A | 9/1999 | Bishay et al. |

(56) References Cited

U.S. PATENT DOCUMENTS

| | | | |
|---|---|---|---|
| 5,953,683 | A | 9/1999 | Hansen et al. |
| 5,957,857 | A | 9/1999 | Hartley |
| 5,961,923 | A | 10/1999 | Nova et al. |
| 5,967,978 | A | 10/1999 | Littmann et al. |
| 5,967,980 | A | 10/1999 | Ferre et al. |
| 5,967,984 | A | 10/1999 | Chu et al. |
| 5,967,991 | A | 10/1999 | Gardineer et al. |
| 5,969,722 | A | 10/1999 | Palm |
| 5,970,119 | A | 10/1999 | Hofmann |
| 5,971,933 | A | 10/1999 | Gopakumaran et al. |
| 5,971,983 | A | 10/1999 | Lesh |
| 5,978,705 | A | 11/1999 | KenKnight et al. |
| 5,983,126 | A | 11/1999 | Wittkampf |
| 5,984,908 | A | 11/1999 | Davis et al. |
| 5,991,693 | A | 11/1999 | Zalewski |
| 5,997,473 | A | 12/1999 | Taniguchi et al. |
| 5,997,481 | A | 12/1999 | Adams et al. |
| 6,004,270 | A | 12/1999 | Urbano et al. |
| 6,006,123 | A | 12/1999 | Nguyen et al. |
| 6,011,988 | A | 1/2000 | Ynch et al. |
| 6,014,473 | A | 1/2000 | Hossack et al. |
| 6,014,580 | A | 1/2000 | Blume et al. |
| 6,015,414 | A | 1/2000 | Werp et al. |
| 6,017,496 | A | 1/2000 | Nova et al. |
| 6,019,724 | A | 2/2000 | Gronningsaeter et al. |
| 6,019,725 | A | 2/2000 | Vesely et al. |
| 6,022,342 | A | 2/2000 | Mukherjee |
| 6,023,638 | A | 2/2000 | Swanson |
| 6,026,312 | A | 2/2000 | Shemwell et al. |
| 6,031,765 | A | 2/2000 | Lee et al. |
| 6,032,070 | A | 2/2000 | Flock et al. |
| 6,039,694 | A | 3/2000 | Larson et al. |
| 6,050,718 | A | 4/2000 | Schena et al. |
| 6,052,610 | A | 4/2000 | Koch |
| 6,052,618 | A | 4/2000 | Dahlke et al. |
| D424,693 | S | 5/2000 | Pruter |
| 6,058,323 | A | 5/2000 | Lemelson |
| 6,059,718 | A | 5/2000 | Taniguchi et al. |
| 6,060,970 | A | 5/2000 | Bell |
| 6,063,032 | A | 5/2000 | Grunwald |
| 6,064,905 | A | 5/2000 | Webster, Jr. et al. |
| 6,066,094 | A | 5/2000 | Ben-Haim |
| 6,068,599 | A | 5/2000 | Saito et al. |
| 6,073,043 | A | 6/2000 | Schneider |
| 6,074,367 | A | 6/2000 | Hubbell |
| 6,075,442 | A | 6/2000 | Welch |
| 6,076,007 | A | 6/2000 | England et al. |
| 6,081,737 | A | 6/2000 | Shah |
| 6,082,366 | A | 7/2000 | Andra et al. |
| 6,083,170 | A | 7/2000 | Ben-Haim |
| 6,099,524 | A | 8/2000 | Lipson et al. |
| 6,100,026 | A | 8/2000 | Nova et al. |
| 6,102,044 | A | 8/2000 | Naidyhorski |
| 6,102,862 | A | 8/2000 | Grunwald et al. |
| 6,107,699 | A | 8/2000 | Swanson |
| 6,112,111 | A | 8/2000 | Glantz |
| 6,112,115 | A | 8/2000 | Feldman et al. |
| 6,113,504 | A | 9/2000 | Kuesters |
| 6,115,624 | A | 9/2000 | Lewis et al. |
| 6,120,445 | A | 9/2000 | Grunwald |
| 6,122,538 | A | 9/2000 | Sliwa, Jr. et al. |
| 6,128,174 | A | 10/2000 | Ritter et al. |
| 6,129,668 | A | 10/2000 | Haynor et al. |
| 6,129,724 | A | 10/2000 | Fleischman et al. |
| 6,132,378 | A | 10/2000 | Marino |
| 6,132,379 | A | 10/2000 | Patacsil et al. |
| 6,135,961 | A | 10/2000 | Pflugrath et al. |
| 6,136,274 | A | 10/2000 | Nova et al. |
| 6,138,681 | A | 10/2000 | Chen et al. |
| 6,139,496 | A | 10/2000 | Chen et al. |
| 6,139,502 | A | 10/2000 | Fredriksen |
| 6,139,540 | A | 10/2000 | Rost et al. |
| 6,144,300 | A | 11/2000 | Dames |
| 6,148,823 | A | 11/2000 | Hastings |
| 6,152,933 | A | 11/2000 | Werp et al. |
| 6,157,853 | A | 12/2000 | Blume et al. |
| 6,165,144 | A | 12/2000 | Talish et al. |
| 6,165,977 | A | 12/2000 | Mochly-Rosen |
| 6,166,496 | A | 12/2000 | Lys et al. |
| 6,166,806 | A | 12/2000 | Tjin |
| 6,167,765 | B1 | 1/2001 | Weitzel |
| 6,172,499 | B1 | 1/2001 | Ashe |
| 6,173,199 | B1 | 1/2001 | Gabriel |
| 6,173,715 | B1 | 1/2001 | Sinanan et al. |
| 6,175,756 | B1 | 1/2001 | Ferre et al. |
| 6,176,829 | B1 | 1/2001 | Vilkomerson |
| 6,187,744 | B1 | 2/2001 | Rooney |
| 6,190,370 | B1 | 2/2001 | Tsui |
| 6,191,136 | B1 | 2/2001 | Marban |
| 6,193,743 | B1 | 2/2001 | Brayton et al. |
| 6,197,001 | B1 | 3/2001 | Wilson et al. |
| 6,200,305 | B1 | 3/2001 | Berthiaume et al. |
| 6,203,499 | B1 | 3/2001 | Imling et al. |
| 6,208,884 | B1 | 3/2001 | Kumar et al. |
| 6,211,626 | B1 | 4/2001 | Lys et al. |
| 6,211,666 | B1 | 4/2001 | Acker |
| 6,212,426 | B1 | 4/2001 | Swanson |
| 6,212,430 | B1 | 4/2001 | Kung |
| 6,216,027 | B1 | 4/2001 | Willis et al. |
| 6,216,028 | B1 | 4/2001 | Haynor et al. |
| 6,216,029 | B1 | 4/2001 | Paltieli |
| 6,217,517 | B1 | 4/2001 | Grunwald |
| 6,223,087 | B1 | 4/2001 | Williams |
| 6,226,547 | B1 | 5/2001 | Lockhart et al. |
| 6,230,042 | B1 | 5/2001 | Slettenmark |
| 6,230,046 | B1 | 5/2001 | Crane et al. |
| 6,231,518 | B1 | 5/2001 | Grabek et al. |
| 6,233,476 | B1 | 5/2001 | Strommer et al. |
| 6,233,994 | B1 | 5/2001 | Roy et al. |
| 6,236,883 | B1 | 5/2001 | Ciaccio et al. |
| 6,238,344 | B1 | 5/2001 | Gamelsky et al. |
| 6,241,673 | B1 | 6/2001 | Williams |
| 6,245,018 | B1 | 6/2001 | Lee |
| 6,246,231 | B1 | 6/2001 | Ashe |
| 6,246,898 | B1 | 6/2001 | Vesely et al. |
| 6,248,072 | B1 | 6/2001 | Murkin |
| 6,248,074 | B1 | 6/2001 | Ohno et al. |
| 6,248,075 | B1 | 6/2001 | McGee et al. |
| 6,249,234 | B1 | 6/2001 | Ely et al. |
| 6,253,770 | B1 | 7/2001 | Acker et al. |
| 6,254,543 | B1 | 7/2001 | Grunwald et al. |
| 6,258,035 | B1 | 7/2001 | Hoeksel et al. |
| 6,259,938 | B1 | 7/2001 | Zarychta et al. |
| 6,259,941 | B1 | 7/2001 | Chia et al. |
| 6,261,231 | B1 | 7/2001 | Damphousse et al. |
| 6,263,230 | B1 | 7/2001 | Haynor et al. |
| 6,266,550 | B1 | 7/2001 | Selmon et al. |
| 6,266,551 | B1 | 7/2001 | Osadchy et al. |
| 6,266,552 | B1 | 7/2001 | Slettenmark |
| 6,266,563 | B1 | 7/2001 | KenKnight et al. |
| 6,270,493 | B1 | 8/2001 | Lalonde et al. |
| 6,271,833 | B1 | 8/2001 | Rosenberg et al. |
| 6,272,371 | B1 | 8/2001 | Shlomo |
| 6,272,374 | B1 | 8/2001 | Flock et al. |
| 6,275,258 | B1 | 8/2001 | Chim |
| 6,275,724 | B1 | 8/2001 | Dickinson et al. |
| 6,277,077 | B1 | 8/2001 | Brisken et al. |
| 6,284,459 | B1 | 9/2001 | Nova et al. |
| 6,285,898 | B1 | 9/2001 | Ben-Haim |
| 6,287,259 | B1 | 9/2001 | Grunwald |
| 6,287,260 | B1 | 9/2001 | Hascoet et al. |
| 6,288,704 | B1 | 9/2001 | Flack et al. |
| 6,292,678 | B1 | 9/2001 | Hall et al. |
| 6,292,680 | B1 | 9/2001 | Somogyi et al. |
| 6,292,901 | B1 | 9/2001 | Lys et al. |
| 6,293,955 | B1 | 9/2001 | Houser et al. |
| 6,296,604 | B1 | 10/2001 | Garibaldi et al. |
| 6,298,261 | B1 | 10/2001 | Rex |
| 6,301,496 | B1 | 10/2001 | Reisfeld |
| 6,304,768 | B1 | 10/2001 | Blume et al. |
| 6,306,097 | B1 | 10/2001 | Park et al. |
| 6,306,105 | B1 | 10/2001 | Rooney et al. |
| 6,310,532 | B1 | 10/2001 | Santa Cruz et al. |
| 6,311,082 | B1 | 10/2001 | Creighton, IV et al. |

(56) References Cited

U.S. PATENT DOCUMENTS 6,315,709 B1 11/2001 Garibaldi et al.
6,315,727 B1 11/2001 Coleman et al.
6,319,668 B1 11/2001 Nova et al.
6,323,769 B1 11/2001 Dames
6,323,770 B1 11/2001 Dames
6,324,416 B1 11/2001 Seibert
6,325,540 B1 12/2001 Lounsberry et al.
6,325,762 B1 12/2001 Tjin
6,329,139 B1 12/2001 Nova et al.
6,329,916 B1 12/2001 Dames
6,330,467 B1 12/2001 Creighton, IV et al.
6,332,089 B1 12/2001 Acker et al.
6,332,874 B1 12/2001 Eliasen et al.
6,340,588 B1 1/2002 Nova et al.
6,340,868 B1 1/2002 Lys et al.
6,341,231 B1 1/2002 Ferre et al.
6,346,081 B1 2/2002 Vilkomerson
6,348,911 B1 2/2002 Rosenberg et al.
6,350,160 B1 2/2002 Feuersanger et al.
6,352,363 B1 3/2002 Munger et al.
6,354,999 B1 3/2002 Dgany et al.
6,355,026 B1 3/2002 Mick
6,356,791 B1 3/2002 Westlund et al.
6,360,123 B1 3/2002 Kimchi et al.
6,361,499 B1 3/2002 Bates et al.
6,364,823 B1 4/2002 Garibaldi et al.
6,364,839 B1 4/2002 Little et al.
6,366,804 B1 4/2002 Mejia
6,368,141 B1 4/2002 VanAntwerp et al.
6,368,285 B1 4/2002 Osadchy et al.
6,369,564 B1 4/2002 Khalfin et al.
6,370,411 B1 4/2002 Osadchy et al.
6,373,240 B1 4/2002 Govari
6,373,388 B1 4/2002 Dames
6,374,134 B1 4/2002 Bladen et al.
6,374,670 B1 4/2002 Spelman et al.
6,375,606 B1 4/2002 Garibaldi et al.
6,375,615 B1 4/2002 Flaherty et al.
6,375,639 B1 4/2002 Duplessie et al.
6,377,857 B1 4/2002 Brayton et al.
6,379,302 B1 4/2002 Kessman et al.
6,379,303 B1 4/2002 Seitz et al.
6,379,307 B1 4/2002 Filly et al.
6,381,485 B1 4/2002 Hunter et al.
6,385,472 B1 5/2002 Hall et al.
6,385,476 B1 5/2002 Osadchy et al.
6,398,736 B1 6/2002 Seward
6,398,738 B1 6/2002 Millar
6,401,723 B1 6/2002 Garibaldi et al.
6,406,422 B1 6/2002 Landesberg
6,406,442 B1 6/2002 McFann et al.
6,412,978 B1 7/2002 Watanabe et al.
6,412,980 B1 7/2002 Lounsberry et al.
6,417,839 B1 7/2002 Odell
6,418,332 B1 7/2002 Mastrototaro et al.
6,418,335 B2 7/2002 Avrin et al.
6,423,002 B1 7/2002 Hossack
6,423,050 B1 7/2002 Twardowski
6,427,079 B1 7/2002 Schneider et al.
6,428,551 B1 8/2002 Hall et al.
6,430,315 B1 8/2002 Makram-Ebeid
6,432,069 B1 8/2002 Godo et al.
6,436,043 B2 8/2002 Bonnefous
6,438,411 B1 8/2002 Guttman et al.
6,442,416 B1 8/2002 Schultz
6,445,943 B1 9/2002 Ferre et al.
6,456,874 B1 9/2002 Hafer et al.
6,459,919 B1 10/2002 Lys et al.
6,463,121 B1 10/2002 Milnes
6,466,815 B1 10/2002 Saito et al.
6,471,656 B1 10/2002 Shalman et al.
6,471,658 B1 10/2002 Daniels et al.
6,471,700 B1 10/2002 Burbank et al.
6,473,167 B1 10/2002 Odell
6,474,341 B1 11/2002 Hunter et al.
6,475,152 B1 11/2002 Kelly, Jr. et al.
6,475,223 B1 11/2002 Werp et al.
6,477,402 B1 11/2002 Lynch et al.
6,484,118 B1 11/2002 Govari
6,487,916 B1 12/2002 Gomm et al.
6,491,671 B1 12/2002 Larson, III et al.
6,493,573 B1 12/2002 Martinelli et al.
6,494,832 B1 12/2002 Feldman et al.
6,496,715 B1 12/2002 Lee et al.
6,498,942 B1 12/2002 Esenaliev et al.
6,498,944 B1 12/2002 Ben-Haim et al.
6,500,141 B1 12/2002 Irion et al.
6,503,205 B2 1/2003 Manor et al.
6,505,062 B1 1/2003 Ritter et al.
6,506,159 B2 1/2003 Hascoet et al.
6,507,751 B2 1/2003 Blume et al.
6,508,769 B2 1/2003 Bonnefous
6,508,802 B1 1/2003 Rosengart et al.
6,511,413 B2 1/2003 Landesberg
6,512,958 B1 1/2003 Swoyer et al.
6,514,202 B2 2/2003 Grunwald
6,514,226 B1 2/2003 Levin et al.
6,514,249 B1 2/2003 Maguire et al.
6,515,657 B1 2/2003 Zanelli
6,516,212 B1 2/2003 Bladen et al.
6,516,231 B1 2/2003 Flammang
6,516,807 B1 2/2003 Panescu et al.
6,517,520 B2 2/2003 Chang et al.
6,522,906 B1 2/2003 Salisbury, Jr. et al.
6,522,907 B1 2/2003 Bladen et al.
6,522,909 B1 2/2003 Garibaldi et al.
6,524,249 B2 2/2003 Moehring et al.
6,524,303 B1 2/2003 Garibaldi
6,528,954 B1 3/2003 Lys et al.
6,528,991 B2 3/2003 Ashe
6,529,761 B2 3/2003 Creighton, IV et al.
6,529,766 B1 3/2003 Guendel
6,534,982 B1 3/2003 Jakab
6,535,625 B1 3/2003 Chang et al.
6,537,192 B1 3/2003 Elliott et al.
6,537,196 B1 3/2003 Creighton, IV et al.
6,538,634 B1 3/2003 Chui et al.
6,540,699 B1 4/2003 Smith
6,542,766 B2 4/2003 Hall et al.
6,544,251 B1 4/2003 Crawford
6,545,678 B1 4/2003 Ohazama
6,546,270 B1 4/2003 Goldin et al.
6,546,279 B1 4/2003 Bova et al.
6,546,787 B1 4/2003 Schiller et al.
6,552,841 B1 4/2003 Asser et al.
6,556,858 B1 4/2003 Zeman
6,562,019 B1 5/2003 Sell
6,564,087 B1 5/2003 Pitris et al.
6,569,101 B2 5/2003 Quistgaard et al.
6,569,103 B2 5/2003 Hoeksel et al.
6,569,160 B1 5/2003 Goldin et al.
6,569,862 B1 5/2003 Marban
6,571,004 B1 5/2003 Florent et al.
6,574,518 B1 6/2003 Lounsberry et al.
6,575,908 B2 6/2003 Barnes et al.
6,577,080 B2 6/2003 Lys et al.
6,577,896 B2 6/2003 Werner et al.
6,584,343 B1 6/2003 Ransbury et al.
6,589,181 B2 7/2003 Grunwald et al.
6,592,520 B1 7/2003 Peszynski et al.
6,592,565 B2 7/2003 Twardowski
6,593,754 B1 7/2003 Steber et al.
6,593,884 B1 7/2003 Gilboa et al.
6,597,943 B2 7/2003 Taha et al.
6,599,249 B1 7/2003 Nordgren et al.
6,607,488 B1 8/2003 Jackson et al.
6,610,058 B2 8/2003 Flores
6,611,141 B1 8/2003 Schulz et al.
6,615,071 B1 9/2003 Casscells, III et al.
6,615,155 B2 9/2003 Gilboa
6,616,610 B2 9/2003 Steininger et al.
6,618,612 B1 9/2003 Acker et al.
6,623,431 B1 9/2003 Sakuma et al.
6,626,832 B1 9/2003 Paltieli et al.

(56) References Cited

U.S. PATENT DOCUMENTS

| | | | |
|---|---|---|---|
| 6,626,834 | B2 | 9/2003 | Dunne et al. |
| 6,626,902 | B1 | 9/2003 | Kucharczyk et al. |
| 6,630,879 | B1 | 10/2003 | Creighton, IV et al. |
| 6,635,027 | B1 | 10/2003 | Cragg et al. |
| 6,641,538 | B2 | 11/2003 | Nakaya et al. |
| 6,645,148 | B2 | 11/2003 | Nguyen-Dinh et al. |
| 6,647,135 | B2 | 11/2003 | Bonnefous |
| 6,648,875 | B2 | 11/2003 | Simpson et al. |
| 6,649,914 | B1 | 11/2003 | Moorman et al. |
| 6,652,505 | B1 | 11/2003 | Tsugita |
| 6,652,506 | B2 | 11/2003 | Bowe et al. |
| 6,654,643 | B1 | 11/2003 | Schmid |
| 6,660,024 | B1 | 12/2003 | Flaherty et al. |
| 6,662,034 | B2 | 12/2003 | Segner et al. |
| 6,663,661 | B2 | 12/2003 | Boneau |
| 6,666,828 | B2 | 12/2003 | Greco et al. |
| 6,672,308 | B1 | 1/2004 | Gaspari |
| 6,677,752 | B1 | 1/2004 | Creighton, IV et al. |
| 6,679,857 | B1 | 1/2004 | Bastia et al. |
| 6,684,176 | B2 | 1/2004 | Willins et al. |
| 6,685,644 | B2 | 2/2004 | Seo et al. |
| 6,687,386 | B1 | 2/2004 | Ito et al. |
| 6,687,531 | B1 | 2/2004 | Ferre et al. |
| 6,689,119 | B1 | 2/2004 | Di Caprio et al. |
| 6,690,963 | B2 | 2/2004 | Ben-Haim et al. |
| 6,690,964 | B2 | 2/2004 | Bieger et al. |
| 6,690,968 | B2 | 2/2004 | Mejia |
| 6,694,167 | B1 | 2/2004 | Ferre et al. |
| 6,695,786 | B2 | 2/2004 | Wang et al. |
| 6,701,179 | B1 | 3/2004 | Martinelli et al. |
| 6,701,918 | B2 | 3/2004 | Fariss et al. |
| 6,702,804 | B1 | 3/2004 | Ritter et al. |
| 6,704,590 | B2 | 3/2004 | Haldeman |
| 6,709,390 | B1 | 3/2004 | Marie Pop |
| 6,711,429 | B1 | 3/2004 | Gilboa et al. |
| 6,711,431 | B2 | 3/2004 | Sarin et al. |
| 6,719,699 | B2 | 4/2004 | Smith |
| 6,719,724 | B1 | 4/2004 | Walker et al. |
| 6,719,756 | B1 | 4/2004 | Muntermann |
| 6,720,745 | B2 | 4/2004 | Lys et al. |
| 6,733,458 | B1 | 5/2004 | Steins et al. |
| 6,733,473 | B1 | 5/2004 | Reifart et al. |
| 6,733,511 | B2 | 5/2004 | Hall et al. |
| 6,736,782 | B2 | 5/2004 | Pfeiffer et al. |
| 6,738,656 | B1 | 5/2004 | Ferre et al. |
| 6,740,103 | B2 | 5/2004 | Hall et al. |
| 6,743,177 | B2 | 6/2004 | Ito |
| 6,749,569 | B1 | 6/2004 | Pellegretti |
| 6,754,596 | B2 | 6/2004 | Ashe |
| 6,754,608 | B2 | 6/2004 | Svanerudh et al. |
| 6,755,789 | B2 | 6/2004 | Stringer et al. |
| 6,755,816 | B2 | 6/2004 | Ritter et al. |
| 6,755,822 | B2 | 6/2004 | Reu et al. |
| 6,757,557 | B1 | 6/2004 | Bladen et al. |
| 6,763,261 | B2 | 7/2004 | Casscells, III et al. |
| 6,764,449 | B2 | 7/2004 | Lee et al. |
| 6,768,496 | B2 | 7/2004 | Bieger et al. |
| 6,772,001 | B2 | 8/2004 | Maschke |
| 6,774,624 | B2 | 8/2004 | Anderson et al. |
| 6,783,536 | B2 | 8/2004 | Vilsmeier et al. |
| 6,784,660 | B2 | 8/2004 | Ashe |
| 6,785,571 | B2 | 8/2004 | Glossop |
| 6,786,219 | B2 | 9/2004 | Garibaldi et al. |
| 6,786,870 | B2 | 9/2004 | Miyaki et al. |
| 6,788,967 | B2 | 9/2004 | Ben-Haim et al. |
| 6,794,667 | B2 | 9/2004 | Noshi |
| 6,799,066 | B2 | 9/2004 | Steines et al. |
| 6,815,651 | B2 | 11/2004 | Odell |
| 6,816,266 | B2 | 11/2004 | Varshneya et al. |
| 6,817,364 | B2 | 11/2004 | Garibaldi et al. |
| 6,834,201 | B2 | 12/2004 | Gillies et al. |
| 6,844,713 | B2 | 1/2005 | Steber et al. |
| 6,845,142 | B2 | 1/2005 | Ohishi |
| 6,850,788 | B2 | 2/2005 | Al-Ali |
| 6,856,823 | B2 | 2/2005 | Ashe |
| 6,857,196 | B2 | 2/2005 | Dalrymple |
| 6,860,422 | B2 | 3/2005 | Hull et al. |
| 6,862,467 | B2 | 3/2005 | Moore et al. |
| 6,869,390 | B2 | 3/2005 | Elliott et al. |
| 6,875,179 | B2 | 4/2005 | Ferguson et al. |
| 6,879,160 | B2 | 4/2005 | Jakab |
| 6,887,206 | B2 | 5/2005 | Hoeksel et al. |
| 6,889,091 | B2 | 5/2005 | Hine et al. |
| 6,895,268 | B1 | 5/2005 | Rahn et al. |
| 6,902,528 | B1 | 6/2005 | Garibaldi et al. |
| 6,905,469 | B2 | 6/2005 | Hascoet et al. |
| 6,908,433 | B1 | 6/2005 | Pruter |
| 6,911,026 | B1 | 6/2005 | Hall et al. |
| 6,923,782 | B2 | 8/2005 | O'Mahony et al. |
| 6,926,673 | B2 | 8/2005 | Roberts et al. |
| 6,926,674 | B2 | 8/2005 | Tenerz et al. |
| 6,934,575 | B2 | 8/2005 | Ferre et al. |
| 6,936,010 | B2 | 8/2005 | Fang et al. |
| 6,939,313 | B2 | 9/2005 | Saadat et al. |
| 6,940,379 | B2 | 9/2005 | Creighton |
| 6,941,166 | B2 | 9/2005 | MacAdam et al. |
| 6,945,938 | B2 | 9/2005 | Grunwald |
| 6,947,788 | B2 | 9/2005 | Gilboa et al. |
| 6,950,689 | B1 | 9/2005 | Willis et al. |
| 6,953,754 | B2 | 10/2005 | Machida et al. |
| 6,958,677 | B1 | 10/2005 | Carter |
| 6,959,214 | B2 | 10/2005 | Pape et al. |
| 6,962,566 | B2 | 11/2005 | Quistgaard et al. |
| 6,968,846 | B2 | 11/2005 | Viswanathan |
| 6,975,197 | B2 | 12/2005 | Creighton, IV |
| 6,976,962 | B2 | 12/2005 | Bullis |
| 6,976,987 | B2 | 12/2005 | Flores |
| 6,979,294 | B1 | 12/2005 | Selzer et al. |
| 6,980,843 | B2 | 12/2005 | Eng et al. |
| 6,980,852 | B2 | 12/2005 | Jersey-Willuhn et al. |
| 6,980,921 | B2 | 12/2005 | Anderson et al. |
| 6,986,739 | B2 | 1/2006 | Warren et al. |
| 6,986,744 | B1 | 1/2006 | Krivitski |
| 6,999,821 | B2 | 2/2006 | Jenney et al. |
| 7,001,355 | B2 | 2/2006 | Nunomura et al. |
| 7,008,418 | B2 | 3/2006 | Hall et al. |
| 7,010,338 | B2 | 3/2006 | Ritter et al. |
| 7,015,393 | B2 | 3/2006 | Weiner et al. |
| 7,017,584 | B2 | 3/2006 | Garibaldi et al. |
| 7,019,610 | B2 | 3/2006 | Creighton, IV et al. |
| 7,020,512 | B2 | 3/2006 | Ritter et al. |
| D518,574 | S | 4/2006 | Chaggares |
| 7,022,075 | B2 | 4/2006 | Grunwald et al. |
| 7,022,082 | B2 | 4/2006 | Sonek |
| 7,026,927 | B2 | 4/2006 | Wright et al. |
| 7,027,634 | B2 | 4/2006 | Odell |
| 7,028,387 | B1 | 4/2006 | Huynh et al. |
| 7,029,446 | B2 | 4/2006 | Wendelken et al. |
| 7,033,603 | B2 | 4/2006 | Nelson et al. |
| D520,139 | S | 5/2006 | Chaggares |
| D520,140 | S | 5/2006 | Chaggares |
| 7,038,398 | B1 | 5/2006 | Lys et al. |
| 7,038,657 | B2 | 5/2006 | Rosenberg et al. |
| 7,043,293 | B1 | 5/2006 | Baura |
| 7,048,733 | B2 | 5/2006 | Hartley et al. |
| 7,054,228 | B1 | 5/2006 | Hickling |
| 7,059,878 | B1 | 6/2006 | Hendrixson |
| 7,065,403 | B1 | 6/2006 | Mouchawar et al. |
| 7,066,914 | B2 | 6/2006 | Andersen |
| 7,066,924 | B1 | 6/2006 | Garibaldi et al. |
| 7,069,072 | B2 | 6/2006 | Jansen et al. |
| D525,363 | S | 7/2006 | Chaggares |
| 7,070,565 | B2 | 7/2006 | Vaezy et al. |
| 7,072,704 | B2 | 7/2006 | Bucholz |
| 7,074,187 | B2 | 7/2006 | Selzer et al. |
| 7,082,325 | B2 | 7/2006 | Hashimshony et al. |
| 7,090,639 | B2 | 8/2006 | Govari |
| 7,096,059 | B2 | 8/2006 | Geddes et al. |
| 7,096,148 | B2 | 8/2006 | Anderson et al. |
| 7,096,870 | B2 | 8/2006 | Amprich et al. |
| 7,098,907 | B2 | 8/2006 | Houston et al. |
| 7,103,205 | B2 | 9/2006 | Wang et al. |
| 7,104,980 | B1 | 9/2006 | Aherty et al. |
| 7,106,043 | B1 | 9/2006 | Da Silva et al. |

(56) References Cited

U.S. PATENT DOCUMENTS 7,106,431 B2 9/2006 Odell
7,106,479 B2 9/2006 Roy et al.
7,107,105 B2 9/2006 Bjorklund et al.
7,112,197 B2 9/2006 Hartley et al.
7,128,734 B1 10/2006 Wilson et al.
7,132,804 B2 11/2006 Lys et al.
7,137,976 B2 11/2006 Ritter et al.
7,141,019 B2 11/2006 Pearlman
7,141,812 B2 11/2006 Appleby et al.
7,142,905 B2 11/2006 Slayton et al.
7,148,970 B2 12/2006 de Boer
7,153,291 B2 12/2006 Bierman
7,161,453 B2 1/2007 Creighton, IV
7,162,291 B1 1/2007 Nachaliel
7,167,738 B2 1/2007 Schweikard et al.
7,169,107 B2 1/2007 Jersey-Willuhn et al.
7,169,109 B2 1/2007 Jansen et al.
7,174,201 B2 2/2007 Govari et al.
7,175,646 B2 2/2007 Brenneman et al.
7,180,252 B2 2/2007 Lys et al.
7,184,820 B2 2/2007 Jersey-Willuhn et al.
7,189,198 B2 3/2007 Harburn et al.
7,189,205 B2 3/2007 McMorrow et al.
7,189,208 B1 3/2007 Beatty et al.
7,190,819 B2 3/2007 Viswanathan
7,194,295 B2 3/2007 Vilsmeier
7,204,798 B2 4/2007 Zdeblick et al.
7,206,064 B2 4/2007 Rogers et al.
7,207,941 B2 4/2007 Sharf
7,211,082 B2 5/2007 Hall et al.
7,214,191 B2 5/2007 Stringer et al.
7,215,326 B2 5/2007 Rosenberg
7,221,104 B2 5/2007 Lys et al.
7,223,256 B2 5/2007 Bierman
7,229,400 B2 6/2007 Elliott et al.
7,231,243 B2 6/2007 Tearney et al.
7,236,157 B2 6/2007 Schena et al.
7,236,816 B2 6/2007 Kumar et al.
7,236,820 B2 6/2007 Mabary et al.
7,237,313 B2 7/2007 Skujins et al.
7,238,169 B2 7/2007 Takagi et al.
7,241,267 B2 7/2007 Furia
7,244,234 B2 7/2007 Ridley et al.
7,248,032 B1 7/2007 Hular et al.
7,248,914 B2 7/2007 Hastings et al.
7,252,633 B2 8/2007 Obata et al.
7,260,428 B2 8/2007 Virtanen
7,261,691 B1 8/2007 Asomani
7,264,584 B2 9/2007 Ritter et al.
7,270,662 B2 9/2007 Visram et al.
7,276,044 B2 10/2007 Ferry et al.
7,286,034 B2 10/2007 Creighton
7,291,146 B2 11/2007 Steinke et al.
7,297,140 B2 11/2007 Orlu et al.
7,299,085 B2 11/2007 Bergelson et al.
7,300,430 B2 11/2007 Wilson et al.
7,302,288 B1 11/2007 Schellenberg
7,308,296 B2 12/2007 Lys et al.
7,310,150 B2 12/2007 Guillermo et al.
7,311,702 B2 12/2007 Tallarida et al.
7,321,228 B2 1/2008 Govari
7,326,241 B2 2/2008 Jang
7,327,872 B2 2/2008 Vaillant et al.
7,331,462 B2 2/2008 Steppe
7,342,058 B2 3/2008 Peppmoller et al.
7,344,554 B2 3/2008 Kuyava et al.
7,349,732 B1 3/2008 Kil et al.
7,355,716 B2 4/2008 de Boer et al.
7,359,554 B2 4/2008 Klingensmith et al.
7,360,427 B2 4/2008 Drinkwater et al.
7,366,376 B2 4/2008 Shishkov et al.
7,366,562 B2 4/2008 Dukesherer et al.
7,366,563 B2 4/2008 Kleen et al.
7,373,271 B1 5/2008 Schneider
7,381,204 B2 6/2008 Wilson et al.
7,382,949 B2 6/2008 Bouma et al.
7,384,407 B2 6/2008 Rodriguez et al.
7,413,562 B2 8/2008 Ferguson et al.
7,418,169 B2 8/2008 Tearney et al.
7,447,408 B2 11/2008 Bouma et al.
7,452,331 B1 11/2008 Pruter
7,452,358 B2 11/2008 Stern et al.
7,454,244 B2 11/2008 Kassab et al.
D585,556 S 1/2009 Kosaku
7,479,141 B2 1/2009 Kleen et al.
7,507,114 B2 3/2009 Kent et al.
7,519,424 B2 4/2009 Dennis et al.
7,529,584 B2 5/2009 Laske et al.
7,534,209 B2 5/2009 Abend et al.
7,534,223 B2 5/2009 Boutilette et al.
7,538,859 B2 5/2009 Tearney et al.
7,543,239 B2 6/2009 Viswanathan et al.
7,546,158 B2 6/2009 Allison et al.
7,547,282 B2 6/2009 Lo et al.
7,551,293 B2 6/2009 Yelin et al.
D603,050 S 10/2009 Chen
7,599,730 B2 10/2009 Hunter et al.
7,606,615 B2 10/2009 Makower et al.
7,613,478 B2 11/2009 Jabri et al.
7,616,992 B2 11/2009 Dennis et al.
7,627,376 B2 12/2009 Dennis et al.
7,635,336 B1 12/2009 Pruter
7,637,163 B2 12/2009 Fetzer et al.
7,637,870 B2 12/2009 Flaherty et al.
7,640,053 B2 12/2009 Verin
7,651,469 B2 1/2010 Osborne et al.
7,652,080 B2 1/2010 Peppmoller et al.
7,660,623 B2 2/2010 Hunter et al.
7,665,893 B2 2/2010 Buchalter
7,666,191 B2 2/2010 Orban et al.
7,668,583 B2 2/2010 Fegert et al.
7,681,579 B2 3/2010 Schwartz
7,691,061 B2 4/2010 Hirota
7,697,972 B2 4/2010 Verard et al.
7,699,779 B2 4/2010 Sasaki et al.
7,699,782 B2 4/2010 Angelsen et al.
7,699,829 B2 4/2010 Harris et al.
7,715,925 B2 5/2010 Hafer et al.
7,727,153 B2 6/2010 Fritz et al.
7,727,192 B2 6/2010 Tokumoto et al.
7,729,743 B2 6/2010 Sabczynski et al.
7,751,865 B2 7/2010 Jascob et al.
7,766,839 B2 8/2010 Rogers et al.
7,771,437 B2 8/2010 Hogg et al.
7,774,051 B2 8/2010 Voth
7,774,055 B1 8/2010 Min
7,794,407 B2 9/2010 Rothenberg
7,798,970 B2 9/2010 Lo et al.
7,819,810 B2 10/2010 Stringer et al.
7,822,464 B2 10/2010 Maschke et al.
7,828,528 B2 11/2010 Estes et al.
7,831,294 B2 11/2010 Viswanathan
7,831,449 B2 11/2010 Ying et al.
7,833,168 B2 11/2010 Taylor et al.
7,833,214 B2 11/2010 Wilson et al.
7,840,252 B2 11/2010 Strommer et al.
D629,526 S 12/2010 Adwig et al.
D629,527 S 12/2010 Crunkilton
7,846,157 B2 12/2010 Kozel
7,850,613 B2 12/2010 Stribling
D630,756 S 1/2011 Kitayama
D630,757 S 1/2011 Kitayama
7,869,854 B2 1/2011 Shachar et al.
7,869,865 B2 1/2011 Govari et al.
7,873,402 B2 1/2011 Shachar
7,887,516 B2 2/2011 Young
7,905,837 B2 3/2011 Suzuki
7,909,815 B2 3/2011 Whitmore et al.
7,925,327 B2 4/2011 Weese
7,927,278 B2 4/2011 Selzer et al.
7,931,596 B2 4/2011 Rachlin et al.
7,947,040 B2 5/2011 Davies et al.
7,969,142 B2 6/2011 Krueger et al.
7,976,469 B2 7/2011 Bonde et al.

(56) References Cited

U.S. PATENT DOCUMENTS 7,976,518 B2 7/2011 Shaughnessy et al.
7,981,038 B2 7/2011 Kanade et al.
7,988,633 B2 8/2011 Hossack et al.
8,016,814 B2 9/2011 Blakstvedt et al.
8,046,052 B2 10/2011 Verard et al.
8,055,327 B2 11/2011 Strommer et al.
8,057,394 B2 11/2011 Dala-Krishna
8,060,185 B2 11/2011 Hunter et al.
8,075,488 B2 12/2011 Burton
8,078,274 B2 12/2011 Kassab
8,078,279 B2 12/2011 Dennis et al.
8,082,025 B2 12/2011 Amitai et al.
8,082,032 B2 12/2011 Kassab et al.
8,088,072 B2 1/2012 Munrow et al.
8,090,427 B2 1/2012 Eck et al.
8,090,430 B2 1/2012 Makower et al.
8,099,161 B2 1/2012 Kassab
8,105,239 B2 1/2012 Specht
8,105,338 B2 1/2012 Anderson et al.
8,114,143 B2 2/2012 Kassab et al.
8,118,743 B2 2/2012 Park et al.
8,123,691 B2 2/2012 Mine et al.
8,133,698 B2 3/2012 Silver
8,142,417 B2 3/2012 Pajunk et al.
8,150,522 B2 4/2012 Echauz et al.
8,152,724 B2 4/2012 Ridley et al.
8,155,732 B2 4/2012 Scholz et al.
8,172,754 B2 5/2012 Watanabe et al.
8,175,368 B2 5/2012 Sathyanarayana
8,200,313 B1 6/2012 Rambod et al.
8,204,582 B2 6/2012 Zantos et al.
8,211,023 B2 7/2012 Swan et al.
8,214,018 B2 7/2012 Markowitz et al.
8,221,402 B2 7/2012 Francischelli et al.
8,226,540 B1 7/2012 Khi
8,228,347 B2 7/2012 Beasley et al.
8,240,211 B2 8/2012 Zeitner et al.
8,241,274 B2 8/2012 Keogh et al.
8,244,339 B2 8/2012 Shen et al.
8,255,035 B2 8/2012 Cao et al.
8,260,395 B2 9/2012 Markowitz et al.
8,262,577 B2 9/2012 Munrow et al.
8,298,147 B2 10/2012 Huennekens et al.
8,298,149 B2 10/2012 Hastings et al.
8,303,502 B2 11/2012 Washburn et al.
8,303,505 B2 11/2012 Webler et al.
8,323,202 B2 12/2012 Roschak et al.
8,326,419 B2 12/2012 Rosenberg et al.
8,326,651 B2 12/2012 McLaren et al.
8,328,727 B2 12/2012 Miele et al.
8,340,751 B2 12/2012 Markowitz et al.
8,346,343 B2 1/2013 Kimura et al.
8,369,922 B2 2/2013 Paul et al.
8,388,541 B2 3/2013 Messerly et al.
8,388,546 B2 3/2013 Rothenberg
8,391,956 B2 3/2013 Zellers et al.
8,400,164 B2 3/2013 Osadchy et al.
8,401,616 B2 3/2013 Verard et al.
8,409,103 B2 4/2013 Grunwald et al.
8,412,313 B2 4/2013 Amitai et al.
8,425,425 B2 4/2013 Hagy et al.
8,437,833 B2 5/2013 Silverstein
8,439,873 B1 5/2013 Donovan
8,442,621 B2 5/2013 Gorek et al.
8,447,384 B2 5/2013 Xu et al.
8,449,465 B2 5/2013 Nair et al.
D684,265 S 6/2013 Cadera
8,456,182 B2 6/2013 Bar-Tal et al.
8,478,382 B2 7/2013 Burnside et al.
8,478,388 B2 7/2013 Nguyen et al.
8,485,980 B2 7/2013 Sinderby et al.
8,494,608 B2 7/2013 Markowitz et al.
8,496,592 B2 7/2013 Ridley et al.
8,504,139 B2 8/2013 Jacobsen et al.
8,512,256 B2 8/2013 Rothenberg
8,521,122 B2 8/2013 Scott et al.
8,527,036 B2 9/2013 Jalde et al.
8,529,433 B2 9/2013 Kawano et al.
8,538,509 B2 9/2013 Harlev et al.
8,545,255 B2 10/2013 Itzler et al.
8,553,954 B2 10/2013 Saikia
8,556,815 B2 10/2013 Pelissier et al.
8,585,600 B2 11/2013 Liu et al.
8,597,193 B2 12/2013 Grunwald et al.
8,620,412 B2 12/2013 Griffiths et al.
8,622,913 B2 1/2014 Dentinger et al.
8,644,907 B2 2/2014 Hartmann et al.
8,663,116 B2 3/2014 Hamilton, Jr.
8,676,295 B2 3/2014 Cunningham et al.
8,684,737 B1 * 4/2014 Jordan .................... F41A 33/00
434/16
8,690,776 B2 4/2014 Razzaque et al.
8,700,137 B2 4/2014 Albert
8,706,457 B2 4/2014 Hart et al.
8,715,195 B2 5/2014 Ziv
8,721,655 B2 5/2014 Viswanathan et al.
8,727,988 B2 5/2014 Flaherty et al.
8,734,357 B2 5/2014 Taylor
8,734,440 B2 5/2014 Wu
8,744,211 B2 6/2014 Owen
8,754,865 B2 6/2014 Merritt et al.
8,761,862 B2 6/2014 Ridley et al.
8,764,663 B2 7/2014 Smok et al.
8,774,907 B2 7/2014 Rothenberg
8,781,555 B2 7/2014 Burnside et al.
8,784,336 B2 7/2014 Bown et al.
8,790,263 B2 7/2014 Randall et al.
8,801,693 B2 8/2014 He et al.
8,849,382 B2 9/2014 Cox et al.
8,858,455 B2 10/2014 Rothenberg
8,934,961 B2 1/2015 Akin et al.
8,939,908 B2 1/2015 Suzuki et al.
8,942,784 B2 1/2015 Neidert et al.
8,965,490 B2 2/2015 Lee et al.
8,971,994 B2 3/2015 Burnside et al.
9,014,794 B2 4/2015 Brodnick et al.
9,022,940 B2 5/2015 Meier
9,033,889 B2 5/2015 Hamilton, Jr.
9,125,578 B2 9/2015 Grunwald
9,138,290 B2 9/2015 Hadjicostis
9,179,860 B2 11/2015 Markowitz et al.
9,198,600 B2 12/2015 Grunwald et al.
9,204,858 B2 12/2015 Pelissier et al.
9,220,477 B2 12/2015 Jrabe et al.
9,295,447 B2 3/2016 Shah
9,320,493 B2 4/2016 Visveshwara
9,339,206 B2 5/2016 Grunwald
9,357,980 B2 6/2016 Toji et al.
9,364,171 B2 6/2016 Harris et al.
9,415,188 B2 8/2016 He et al.
9,427,207 B2 8/2016 Sheldon et al.
9,445,780 B2 9/2016 Hossack et al.
9,456,766 B2 10/2016 Cox et al.
9,456,804 B2 10/2016 Tamada
9,459,087 B2 10/2016 Dunbar et al.
9,468,413 B2 10/2016 Hall et al.
9,492,097 B2 11/2016 Wilkes et al.
9,521,961 B2 12/2016 Silverstein et al.
9,526,440 B2 12/2016 Burnside et al.
9,532,724 B2 1/2017 Grunwald
9,554,716 B2 1/2017 Burnside et al.
9,582,876 B2 2/2017 Specht
9,610,061 B2 4/2017 Ebbini et al.
9,636,031 B2 5/2017 Cox
9,642,986 B2 5/2017 Beasley
9,649,037 B2 5/2017 Lowe et al.
9,649,048 B2 5/2017 Cox et al.
9,681,823 B2 6/2017 Messerly et al.
9,702,969 B2 7/2017 Hope Simpson et al.
9,715,757 B2 7/2017 Ng et al.
9,717,415 B2 8/2017 Cohen et al.
9,731,066 B2 8/2017 Liu et al.
9,814,433 B2 11/2017 Benishti et al.
9,814,531 B2 11/2017 Yagi et al.

(56) References Cited

U.S. PATENT DOCUMENTS

| | | | |
|---|---|---|---|
| 9,833,169 | B2 | 12/2017 | Rothenberg |
| 9,839,372 | B2 | 12/2017 | Bukhman et al. |
| 9,861,337 | B2 | 1/2018 | Patwardhan et al. |
| 9,895,138 | B2 | 2/2018 | Sasaki |
| 9,901,714 | B2 | 2/2018 | Lemon et al. |
| 9,907,513 | B2 | 3/2018 | Silverstein |
| 9,913,605 | B2 | 3/2018 | Harris et al. |
| 9,949,720 | B2 | 4/2018 | Southard et al. |
| 9,950,139 | B2 | 4/2018 | Blanchard et al. |
| 9,999,371 | B2 | 6/2018 | Messerly et al. |
| 10,004,875 | B2 | 6/2018 | Bown et al. |
| 10,032,552 | B2 | 7/2018 | Ma et al. |
| 10,043,272 | B2 | 8/2018 | Forzoni et al. |
| 10,046,139 | B2 | 8/2018 | Powers et al. |
| 10,105,121 | B2 | 10/2018 | Burnside et al. |
| 10,165,962 | B2 | 1/2019 | Messerly et al. |
| 10,231,643 | B2 | 3/2019 | Grunwald |
| 10,231,753 | B2 | 3/2019 | Burnside et al. |
| 10,238,418 | B2 | 3/2019 | Cox et al. |
| 10,249,424 | B2 | 4/2019 | Ma et al. |
| 10,271,762 | B2 | 4/2019 | Grunwald |
| 10,342,575 | B2 | 7/2019 | Cox et al. |
| 10,349,857 | B2 | 7/2019 | Grunwald |
| 10,349,890 | B2 | 7/2019 | Misener et al. |
| 10,449,330 | B2 | 10/2019 | Newman et al. |
| 10,524,691 | B2 | 1/2020 | Newman et al. |
| 10,524,694 | B2 | 1/2020 | Hunter |
| 10,602,958 | B2 | 3/2020 | Silverstein et al. |
| 10,751,509 | B2 | 8/2020 | Misener |
| 10,849,695 | B2 | 12/2020 | Cox et al. |
| 10,966,630 | B2 | 4/2021 | Messerly et al. |
| 11,027,101 | B2 | 6/2021 | Lemon et al. |
| 11,103,213 | B2 | 8/2021 | Burnside et al. |
| 11,123,099 | B2 | 9/2021 | Cox et al. |
| 11,529,070 | B2 | 12/2022 | Silverstein et al. |
| 11,707,205 | B2 | 7/2023 | Messerly et al. |
| 11,779,240 | B2 | 10/2023 | Cox et al. |
| 12,295,714 | B2 | 5/2025 | Newman et al. |
| 2001/0014774 | A1 | 8/2001 | Grunwald |
| 2001/0027332 | A1 | 10/2001 | Grunwald et al. |
| 2002/0010392 | A1 | 1/2002 | Desai |
| 2002/0016549 | A1 | 2/2002 | Mejia |
| 2002/0019447 | A1 | 2/2002 | Renn et al. |
| 2002/0022777 | A1 | 2/2002 | Crieghton et al. |
| 2002/0032391 | A1 | 3/2002 | McFann et al. |
| 2002/0045810 | A1 | 4/2002 | Ben-Haim |
| 2002/0049488 | A1 | 4/2002 | Boneau |
| 2002/0055680 | A1 | 5/2002 | Miele et al. |
| 2002/0082559 | A1 | 6/2002 | Chang et al. |
| 2002/0113555 | A1 | 8/2002 | Fys et al. |
| 2002/0123679 | A1 | 9/2002 | Dominguez |
| 2002/0128554 | A1 | 9/2002 | Seward |
| 2002/0129952 | A1 | 9/2002 | Matsudate et al. |
| 2002/0133079 | A1 | 9/2002 | Sandhu |
| 2002/0138007 | A1 | 9/2002 | Nguyen-Dinh et al. |
| 2002/0156363 | A1 | 10/2002 | Hunter et al. |
| 2002/0156376 | A1 | 10/2002 | Wang et al. |
| 2002/0165448 | A1 | 11/2002 | Ben-Haim et al. |
| 2002/0165534 | A1 | 11/2002 | Hayzelden et al. |
| 2002/0165537 | A1 | 11/2002 | Kelley et al. |
| 2002/0173721 | A1 | 11/2002 | Grunwald et al. |
| 2002/0193756 | A1 | 12/2002 | Prindle |
| 2002/0198568 | A1 | 12/2002 | Hafer et al. |
| 2003/0009132 | A1 | 1/2003 | Schwartz et al. |
| 2003/0011359 | A1 | 1/2003 | Ashe |
| 2003/0013959 | A1 | 1/2003 | Grunwald et al. |
| 2003/0013966 | A1 | 1/2003 | Barnes et al. |
| 2003/0013986 | A1 | 1/2003 | Saadat |
| 2003/0018251 | A1 | 1/2003 | Solomon |
| 2003/0036696 | A1 | 2/2003 | Willis et al. |
| 2003/0040671 | A1 | 2/2003 | Somogyi et al. |
| 2003/0040743 | A1 | 2/2003 | Cosman et al. |
| 2003/0047126 | A1 | 3/2003 | Tomaschko |
| 2003/0072805 | A1 | 4/2003 | Miyazawa et al. |
| 2003/0073901 | A1 | 4/2003 | Simon et al. |
| 2003/0076281 | A1 | 4/2003 | Morgan et al. |
| 2003/0083698 | A1 | 5/2003 | Whitehurst et al. |
| 2003/0088195 | A1 | 5/2003 | Vardi et al. |
| 2003/0092993 | A1 | 5/2003 | Grunwald |
| 2003/0100849 | A1 | 5/2003 | Jang |
| 2003/0114742 | A1 | 6/2003 | Lewkowicz et al. |
| 2003/0114777 | A1 | 6/2003 | Griffin et al. |
| 2003/0120150 | A1 | 6/2003 | Govari |
| 2003/0120154 | A1 | 6/2003 | Sauer et al. |
| 2003/0139661 | A1 | 7/2003 | Kimchy et al. |
| 2003/0149328 | A1 | 8/2003 | Elliott et al. |
| 2003/0149368 | A1 | 8/2003 | Hennemann et al. |
| 2003/0152290 | A1 | 8/2003 | Odell |
| 2003/0160721 | A1 | 8/2003 | Gilboa et al. |
| 2003/0162414 | A1 | 8/2003 | Schulz et al. |
| 2003/0163037 | A1 | 8/2003 | Bladen et al. |
| 2003/0163142 | A1 | 8/2003 | Paltieli et al. |
| 2003/0171691 | A1 | 9/2003 | Casscells et al. |
| 2003/0173953 | A1 | 9/2003 | Ashe |
| 2003/0181892 | A1 | 9/2003 | Pajunk et al. |
| 2003/0184544 | A1 | 10/2003 | Prudent |
| 2003/0191392 | A1 | 10/2003 | Haldeman |
| 2003/0191460 | A1 | 10/2003 | Hobbs et al. |
| 2003/0195420 | A1 | 10/2003 | Mendlein et al. |
| 2003/0199746 | A1 | 10/2003 | Fuimaono et al. |
| 2003/0208142 | A1 | 11/2003 | Boudewijn et al. |
| 2003/0216639 | A1 | 11/2003 | Gilboa et al. |
| 2003/0216723 | A1 | 11/2003 | Shinmura et al. |
| 2003/0220557 | A1 | 11/2003 | Cleary et al. |
| 2003/0220578 | A1 | 11/2003 | Ho et al. |
| 2003/0229298 | A1 | 12/2003 | Iwami et al. |
| 2003/0233042 | A1 | 12/2003 | Ashe |
| 2003/0236445 | A1 | 12/2003 | Couvillon |
| 2004/0010189 | A1 | 1/2004 | van Sloun et al. |
| 2004/0015070 | A1 | 1/2004 | Liang et al. |
| 2004/0024301 | A1 | 2/2004 | Hockett et al. |
| 2004/0030319 | A1 | 2/2004 | Korkor et al. |
| 2004/0054278 | A1 | 3/2004 | Kimchy et al. |
| 2004/0059217 | A1 | 3/2004 | Kessman et al. |
| 2004/0059237 | A1 | 3/2004 | Narayan et al. |
| 2004/0082916 | A1 | 4/2004 | Jenkins |
| 2004/0087877 | A1 | 5/2004 | Besz et al. |
| 2004/0088136 | A1 | 5/2004 | Ashe |
| 2004/0092962 | A1 | 5/2004 | Thornton et al. |
| 2004/0097803 | A1 | 5/2004 | Panescu |
| 2004/0097804 | A1 | 5/2004 | Sobe |
| 2004/0097805 | A1 | 5/2004 | Verard et al. |
| 2004/0097806 | A1 | 5/2004 | Hunter et al. |
| 2004/0116809 | A1 | 6/2004 | Chow et al. |
| 2004/0127805 | A1 | 7/2004 | MacAdam et al. |
| 2004/0131998 | A1 | 7/2004 | Marom et al. |
| 2004/0133111 | A1 | 7/2004 | Szczech et al. |
| 2004/0133130 | A1 | 7/2004 | Ferry et al. |
| 2004/0135069 | A1 | 7/2004 | Odell |
| 2004/0138557 | A1 | 7/2004 | Le et al. |
| 2004/0138564 | A1 | 7/2004 | Hwang et al. |
| 2004/0138569 | A1 | 7/2004 | Grunwald et al. |
| 2004/0138570 | A1 | 7/2004 | Nita et al. |
| 2004/0143183 | A1 | 7/2004 | Toyoda et al. |
| 2004/0147837 | A1 | 7/2004 | Macaulay et al. |
| 2004/0150963 | A1 | 8/2004 | Holmberg et al. |
| 2004/0152972 | A1 | 8/2004 | Hunter |
| 2004/0155609 | A1 | 8/2004 | Lys et al. |
| 2004/0158140 | A1 | 8/2004 | Fuimaono et al. |
| 2004/0162487 | A1 | 8/2004 | Klingenbeck-Regn et al. |
| 2004/0171924 | A1 | 9/2004 | Mire et al. |
| 2004/0176688 | A1 | 9/2004 | Haldeman |
| 2004/0186461 | A1 | 9/2004 | DiMatteo |
| 2004/0199069 | A1 | 10/2004 | Connelly et al. |
| 2004/0210289 | A1 | 10/2004 | Wang et al. |
| 2004/0225233 | A1 | 11/2004 | Frankowski et al. |
| 2004/0230131 | A1 | 11/2004 | Kassab et al. |
| 2004/0230271 | A1 | 11/2004 | Wang et al. |
| 2004/0234453 | A1 | 11/2004 | Smith |
| 2004/0243018 | A1 | 12/2004 | Organ et al. |
| 2004/0243116 | A1 | 12/2004 | Joye et al. |
| 2004/0243118 | A1 | 12/2004 | Ayers et al. |
| 2004/0253365 | A1 | 12/2004 | Warren et al. |
| 2004/0254470 | A1 | 12/2004 | Drinkwater et al. |

(56) References Cited

U.S. PATENT DOCUMENTS

2004/0254495 A1 12/2004 Mabary et al.
2004/0260174 A1 12/2004 Keene
2004/0267086 A1 12/2004 Anstadt et al.
2005/0004450 A1 1/2005 Ben-Haim et al.
2005/0021019 A1 1/2005 Hashimshony et al.
2005/0033150 A1 2/2005 Takahashi et al.
2005/0033232 A1* 2/2005 Kriesel ............... A61M 5/1454 604/131
2005/0038355 A1 2/2005 Gellman et al.
2005/0043640 A1 2/2005 Chang
2005/0049486 A1 3/2005 Urquhart et al.
2005/0049504 A1 3/2005 Lo et al.
2005/0049510 A1 3/2005 Haldeman et al.
2005/0063194 A1 3/2005 Lys et al.
2005/0070788 A1 3/2005 Wilson et al.
2005/0075561 A1 4/2005 Golden
2005/0085715 A1 4/2005 Dukesherer et al.
2005/0085716 A1 4/2005 Hamm et al.
2005/0085718 A1 4/2005 Shahidi
2005/0085720 A1 4/2005 Jascob et al.
2005/0090746 A1 4/2005 Ohtake
2005/0096543 A1 5/2005 Jackson et al.
2005/0101868 A1 5/2005 Ridley et al.
2005/0101869 A1 5/2005 Burba et al.
2005/0105081 A1 5/2005 Odell
2005/0105101 A1 5/2005 Duling et al.
2005/0112135 A1 5/2005 Cormier et al.
2005/0113669 A1 5/2005 Helfer et al.
2005/0113676 A1 5/2005 Weiner et al.
2005/0113700 A1 5/2005 Yanagihara et al.
2005/0113873 A1 5/2005 Weiner et al.
2005/0113874 A1 5/2005 Connelly et al.
2005/0113876 A1 5/2005 Weiner et al.
2005/0143689 A1 6/2005 Ramsey
2005/0148836 A1 7/2005 Kleen et al.
2005/0148902 A1 7/2005 Minar et al.
2005/0149002 A1 7/2005 Wang et al.
2005/0151489 A1 7/2005 Lys et al.
2005/0154308 A1 7/2005 Quistgaard et al.
2005/0159644 A1 7/2005 Takano
2005/0159790 A1 7/2005 Shalev
2005/0165301 A1 7/2005 Smith et al.
2005/0165313 A1 7/2005 Byron et al.
2005/0175665 A1 8/2005 Hunter et al.
2005/0175703 A1 8/2005 Hunter et al.
2005/0178395 A1 8/2005 Hunter et al.
2005/0178396 A1 8/2005 Hunter et al.
2005/0182295 A1 8/2005 Soper et al.
2005/0182454 A1 8/2005 Gharib et al.
2005/0197674 A1 9/2005 McCabe et al.
2005/0203368 A1 9/2005 Verin
2005/0203396 A1 9/2005 Angelsen et al.
2005/0205081 A1 9/2005 Barker et al.
2005/0215901 A1 9/2005 Anderson et al.
2005/0215945 A1 9/2005 Harris et al.
2005/0222532 A1 10/2005 Bertolero et al.
2005/0240102 A1 10/2005 Rachlin et al.
2005/0245811 A1 11/2005 Scheffler
2005/0256398 A1 11/2005 Hastings et al.
2005/0256451 A1 11/2005 Adams et al.
2005/0256521 A1 11/2005 Kozel
2005/0256541 A1 11/2005 Stypulkowski
2005/0267365 A1 12/2005 Sokulin et al.
2005/0283210 A1 12/2005 Blischak et al.
2005/0283216 A1 12/2005 Pyles
2005/0288586 A1 12/2005 Ferek-Petric
2005/0288695 A1 12/2005 Jenson et al.
2006/0009759 A1 1/2006 Christian et al.
2006/0015003 A1 1/2006 Moaddes et al.
2006/0015039 A1 1/2006 Cassidy et al.
2006/0025677 A1 2/2006 Verard et al.
2006/0025697 A1 2/2006 Kurzweil et al.
2006/0058633 A1 3/2006 Hoshino et al.
2006/0058654 A1 3/2006 Di Marco et al.
2006/0065275 A1 3/2006 Amprich et al.
2006/0068074 A1 3/2006 Stefandl
2006/0079781 A1 4/2006 Germond-Rouet et al.
2006/0084867 A1 4/2006 Tremblay et al.
2006/0106306 A1 5/2006 Essner et al.
2006/0116571 A1 6/2006 Maschke et al.
2006/0116576 A1 6/2006 McGee et al.
2006/0116578 A1 6/2006 Grunwald et al.
2006/0122514 A1 6/2006 Byrd et al.
2006/0142656 A1 6/2006 Malackowski et al.
2006/0149134 A1 7/2006 Soper et al.
2006/0173251 A1 8/2006 Govari et al.
2006/0173329 A1 8/2006 Irioka et al.
2006/0173407 A1 8/2006 Shaughnessy et al.
2006/0176242 A1 8/2006 Jaramaz et al.
2006/0184029 A1 8/2006 Haim et al.
2006/0184074 A1 8/2006 Vaezy et al.
2006/0206037 A1 9/2006 Braxton
2006/0210130 A1 9/2006 Germond-Rouet et al.
2006/0211944 A1 9/2006 Mauge et al.
2006/0217655 A1 9/2006 Vitullo et al.
2006/0217755 A1 9/2006 Eversull et al.
2006/0224188 A1 10/2006 Libbus et al.
2006/0241397 A1 10/2006 Govari et al.
2006/0241432 A1 10/2006 Herline et al.
2006/0247746 A1 11/2006 Danek et al.
2006/0253029 A1 11/2006 Altmann et al.
2006/0253115 A1 11/2006 Avitall et al.
2006/0258895 A1 11/2006 Maschke
2006/0276867 A1 12/2006 Viswanathan
2006/0287595 A1 12/2006 Maschke
2007/0010753 A1 1/2007 MacAdam
2007/0013540 A1 1/2007 Altmann et al.
2007/0015960 A1 1/2007 Gornert et al.
2007/0016007 A1 1/2007 Govari et al.
2007/0016013 A1 1/2007 Camus
2007/0016068 A1 1/2007 Grunwald et al.
2007/0016069 A1 1/2007 Grunwald et al.
2007/0016070 A1 1/2007 Grunwald et al.
2007/0016072 A1 1/2007 Grunwald et al.
2007/0016131 A1 1/2007 Munger et al.
2007/0032746 A1 2/2007 Sell
2007/0038113 A1 2/2007 Donuki et al.
2007/0049817 A1 3/2007 Preiss et al.
2007/0049822 A1 3/2007 Bunce et al.
2007/0049846 A1 3/2007 Bown et al.
2007/0055141 A1 3/2007 Kruger et al.
2007/0055142 A1 3/2007 Webler
2007/0055294 A1 3/2007 Giap
2007/0060992 A1 3/2007 Pappone
2007/0062544 A1 3/2007 Rauk Bergstrom et al.
2007/0066888 A1 3/2007 Maschke
2007/0073155 A1 3/2007 Park et al.
2007/0078343 A1 4/2007 Kawashima et al.
2007/0087038 A1 4/2007 Richardson et al.
2007/0093710 A1 4/2007 Maschke
2007/0100236 A1 5/2007 McMorrow et al.
2007/0100285 A1 5/2007 Griffin et al.
2007/0112282 A1 5/2007 Skujins et al.
2007/0123805 A1 5/2007 Shireman et al.
2007/0129770 A1 6/2007 Younis
2007/0135803 A1 6/2007 Belson
2007/0135886 A1 6/2007 Maschke
2007/0156205 A1 7/2007 Larson et al.
2007/0161853 A1 7/2007 Yagi et al.
2007/0161914 A1 7/2007 Zdeblick et al.
2007/0161915 A1 7/2007 Desai
2007/0167738 A1 7/2007 Timinger et al.
2007/0167743 A1 7/2007 Honda et al.
2007/0167762 A1 7/2007 Kim et al.
2007/0167769 A1 7/2007 Ikuma et al.
2007/0167801 A1 7/2007 Webler et al.
2007/0167997 A1 7/2007 Forsberg et al.
2007/0197891 A1 8/2007 Shachar et al.
2007/0197905 A1 8/2007 Timinger et al.
2007/0197926 A1 8/2007 Danehorn et al.
2007/0199848 A1 8/2007 Ellswood et al.
2007/0208255 A1 9/2007 Ridley et al.
2007/0219453 A1 9/2007 Kremliovsky et al.
2007/0225589 A1 9/2007 Viswanathan

(56) References Cited

U.S. PATENT DOCUMENTS

| | | | |
|---|---|---|---|
| 2007/0225610 | A1 | 9/2007 | Mickley et al. |
| 2007/0232882 | A1 | 10/2007 | Glossop et al. |
| 2007/0232896 | A1 | 10/2007 | Gilboa et al. |
| 2007/0238984 | A1 | 10/2007 | Maschke et al. |
| 2007/0239004 | A1 | 10/2007 | Kakee et al. |
| 2007/0239018 | A1 | 10/2007 | Fetzer et al. |
| 2007/0244387 | A1 | 10/2007 | Rodriguez Ponce et al. |
| 2007/0244413 | A1 | 10/2007 | Biggins |
| 2007/0247454 | A1 | 10/2007 | Rahn et al. |
| 2007/0249911 | A1 | 10/2007 | Simon |
| 2007/0250150 | A1 | 10/2007 | Pal et al. |
| 2007/0255270 | A1 | 11/2007 | Carney |
| 2007/0265526 | A1 | 11/2007 | Govari et al. |
| 2007/0280974 | A1 | 12/2007 | Son et al. |
| 2007/0282196 | A1 | 12/2007 | Birk et al. |
| 2007/0282197 | A1 | 12/2007 | Bill et al. |
| 2007/0299352 | A1 | 12/2007 | Harlev et al. |
| 2007/0299353 | A1 | 12/2007 | Harlev et al. |
| 2008/0004652 | A1 | 1/2008 | Abboud et al. |
| 2008/0008745 | A1 | 1/2008 | Stinchcomb et al. |
| 2008/0009720 | A1 | 1/2008 | Schefelker et al. |
| 2008/0015442 | A1 | 1/2008 | Watson et al. |
| 2008/0021283 | A1 | 1/2008 | Kuranda |
| 2008/0021322 | A1 | 1/2008 | Stone et al. |
| 2008/0027320 | A1 | 1/2008 | Bolorforosh et al. |
| 2008/0033282 | A1 | 2/2008 | Bar-Tal et al. |
| 2008/0033283 | A1 | 2/2008 | Dellaca et al. |
| 2008/0033316 | A1 | 2/2008 | Kassab et al. |
| 2008/0033350 | A1 | 2/2008 | Wilson et al. |
| 2008/0033759 | A1 | 2/2008 | Finlay |
| 2008/0045908 | A1 | 2/2008 | Gould et al. |
| 2008/0051626 | A1 | 2/2008 | Sato et al. |
| 2008/0077158 | A1 | 3/2008 | Haider et al. |
| 2008/0081958 | A1 | 4/2008 | Denison et al. |
| 2008/0082136 | A1 | 4/2008 | Gaudiani |
| 2008/0097232 | A1 | 4/2008 | Rothenberg |
| 2008/0108949 | A1 | 5/2008 | Beasley et al. |
| 2008/0114095 | A1 | 5/2008 | Peppmoller et al. |
| 2008/0119697 | A1 | 5/2008 | Vadodaria et al. |
| 2008/0125772 | A1 | 5/2008 | Stone et al. |
| 2008/0137927 | A1 | 6/2008 | Altmann et al. |
| 2008/0139944 | A1 | 6/2008 | Weymer et al. |
| 2008/0146915 | A1 | 6/2008 | McMorrow |
| 2008/0146925 | A1 | 6/2008 | Byrd et al. |
| 2008/0146939 | A1 | 6/2008 | McMorrow et al. |
| 2008/0146940 | A1 | 6/2008 | Jenkins et al. |
| 2008/0146941 | A1 | 6/2008 | Dala-Krishna |
| 2008/0146942 | A1 | 6/2008 | Dala-Krishna |
| 2008/0154100 | A1 | 6/2008 | Thalmeier et al. |
| 2008/0166453 | A1 | 7/2008 | Steele et al. |
| 2008/0171934 | A1 | 7/2008 | Greenan et al. |
| 2008/0183075 | A1 | 7/2008 | Govari et al. |
| 2008/0188830 | A1 | 8/2008 | Rosenblatt et al. |
| 2008/0190438 | A1 | 8/2008 | Harlev et al. |
| 2008/0195169 | A1 | 8/2008 | Pinter et al. |
| 2008/0200754 | A1 | 8/2008 | Buchalter |
| 2008/0200801 | A1 | 8/2008 | Wildes et al. |
| 2008/0200913 | A1 | 8/2008 | Viswanathan |
| 2008/0228082 | A1 | 9/2008 | Scheirer et al. |
| 2008/0236598 | A1 | 10/2008 | Gobel |
| 2008/0255404 | A1 | 10/2008 | Nogawa et al. |
| 2008/0255446 | A1 | 10/2008 | Akins |
| 2008/0255475 | A1 | 10/2008 | Kondrosky et al. |
| 2008/0262338 | A1 | 10/2008 | Paitel et al. |
| 2008/0269581 | A1 | 10/2008 | Wood et al. |
| 2008/0269611 | A1 | 10/2008 | Pedrizzetti et al. |
| 2008/0275465 | A1 | 11/2008 | Paul et al. |
| 2008/0275765 | A1 | 11/2008 | Kuchar |
| 2008/0288038 | A1 | 11/2008 | Paul et al. |
| 2008/0294041 | A1 | 11/2008 | Kassab |
| 2008/0319350 | A1 | 12/2008 | Wallace et al. |
| 2009/0005674 | A1 | 1/2009 | Saadat et al. |
| 2009/0005675 | A1 | 1/2009 | Grunwald et al. |
| 2009/0005679 | A1 | 1/2009 | Dala-Krishna |
| 2009/0012399 | A1 | 1/2009 | Sunagawa et al. |
| 2009/0018497 | A1 | 1/2009 | Birchard et al. |
| 2009/0024018 | A1 | 1/2009 | Boyden et al. |
| 2009/0030380 | A1 | 1/2009 | Binmoeller |
| 2009/0043205 | A1 | 2/2009 | Pelissier et al. |
| 2009/0062646 | A1 | 3/2009 | Creighton, IV et al. |
| 2009/0062684 | A1 | 3/2009 | Gregersen et al. |
| 2009/0062772 | A1 | 3/2009 | Wakeford et al. |
| 2009/0080738 | A1 | 3/2009 | Zur et al. |
| 2009/0082661 | A1 | 3/2009 | Saladin et al. |
| 2009/0084382 | A1 | 4/2009 | Jalde et al. |
| 2009/0099468 | A1 | 4/2009 | Thiagalingam et al. |
| 2009/0101577 | A1 | 4/2009 | Fulkerson et al. |
| 2009/0115406 | A1 | 5/2009 | Anderson et al. |
| 2009/0118612 | A1 | 5/2009 | Grunwald et al. |
| 2009/0118637 | A1 | 5/2009 | Kassab et al. |
| 2009/0118706 | A1 | 5/2009 | Schweikert et al. |
| 2009/0124901 | A1 | 5/2009 | Fink et al. |
| 2009/0143672 | A1 | 6/2009 | Harms et al. |
| 2009/0143736 | A1 | 6/2009 | Mittermeyer et al. |
| 2009/0156926 | A1 | 6/2009 | Messerly et al. |
| 2009/0163810 | A1 | 6/2009 | Kanade et al. |
| 2009/0171217 | A1 | 7/2009 | Kim et al. |
| 2009/0177083 | A1 | 7/2009 | Matsumura |
| 2009/0177090 | A1 | 7/2009 | Grunwald et al. |
| 2009/0182224 | A1 | 7/2009 | Shmarak et al. |
| 2009/0203989 | A1 | 8/2009 | Burnside et al. |
| 2009/0204113 | A1 | 8/2009 | MacAdam et al. |
| 2009/0209872 | A1 | 8/2009 | Pop |
| 2009/0209950 | A1 | 8/2009 | Starksen |
| 2009/0221908 | A1 | 9/2009 | Glossop |
| 2009/0227952 | A1 | 9/2009 | Blakstvedt et al. |
| 2009/0234328 | A1 | 9/2009 | Cox et al. |
| 2009/0247835 | A1 | 10/2009 | Voipio |
| 2009/0253976 | A1 | 10/2009 | Harlev et al. |
| 2009/0258171 | A1 | 10/2009 | Uang |
| 2009/0259124 | A1 | 10/2009 | Rothenberg |
| 2009/0262982 | A1 | 10/2009 | Markowitz et al. |
| 2009/0269949 | A1* | 10/2009 | Schmidgall ............ H01R 12/88 29/854 |
| 2009/0270729 | A1 | 10/2009 | Corbucci et al. |
| 2009/0270746 | A1 | 10/2009 | Min |
| 2009/0275828 | A1 | 11/2009 | Shachar et al. |
| 2009/0281419 | A1 | 11/2009 | Troesken et al. |
| 2009/0297441 | A1 | 12/2009 | Canham et al. |
| 2009/0312629 | A1 | 12/2009 | Razzaque et al. |
| 2010/0004543 | A1 | 1/2010 | Ahlund et al. |
| 2010/0004547 | A1 | 1/2010 | Scholz et al. |
| 2010/0010355 | A1 | 1/2010 | Kassab |
| 2010/0010444 | A1 | 1/2010 | Bettuchi |
| 2010/0010612 | A1 | 1/2010 | Gelbart et al. |
| 2010/0016726 | A1 | 1/2010 | Meier |
| 2010/0036227 | A1 | 2/2010 | Cox et al. |
| 2010/0036238 | A1 | 2/2010 | Neidert et al. |
| 2010/0036284 | A1 | 2/2010 | Laynes et al. |
| 2010/0041973 | A1 | 2/2010 | Vu et al. |
| 2010/0041984 | A1 | 2/2010 | Shapland et al. |
| 2010/0049062 | A1 | 2/2010 | Ziv |
| 2010/0055153 | A1 | 3/2010 | Majmudar |
| 2010/0055184 | A1 | 3/2010 | Zeitels et al. |
| 2010/0057157 | A1 | 3/2010 | Govari et al. |
| 2010/0060472 | A1 | 3/2010 | Kimura et al. |
| 2010/0063401 | A1 | 3/2010 | Nishina et al. |
| 2010/0076305 | A1 | 3/2010 | Maier-Hein et al. |
| 2010/0076328 | A1 | 3/2010 | Matsumura et al. |
| 2010/0081934 | A1 | 4/2010 | Soltani et al. |
| 2010/0083719 | A1 | 4/2010 | Peppmoller et al. |
| 2010/0094116 | A1 | 4/2010 | Silverstein |
| 2010/0106011 | A1 | 4/2010 | Byrd et al. |
| 2010/0113917 | A1 | 5/2010 | Anderson |
| 2010/0114573 | A1 | 5/2010 | Huang et al. |
| 2010/0117659 | A1 | 5/2010 | Osadchy et al. |
| 2010/0130858 | A1 | 5/2010 | Arai et al. |
| 2010/0143119 | A1 | 6/2010 | Kooijman et al. |
| 2010/0152596 | A1 | 6/2010 | Griffiths et al. |
| 2010/0152604 | A1 | 6/2010 | Kaula et al. |
| 2010/0160772 | A1 | 6/2010 | Gardeski et al. |
| 2010/0168557 | A1 | 7/2010 | Deno et al. |
| 2010/0168767 | A1* | 7/2010 | Yassinzadeh ...... A61B 17/0057 606/139 |

(56) References Cited

U.S. PATENT DOCUMENTS

2010/0185097 A1 7/2010 Hall
2010/0198048 A1 8/2010 Togawa
2010/0198346 A1 8/2010 Keogh et al.
2010/0204569 A1 8/2010 Burnside et al.
2010/0204614 A1 8/2010 Lindquist et al.
2010/0210938 A1 8/2010 Verard et al.
2010/0210939 A1 8/2010 Hartmann et al.
2010/0210950 A1 8/2010 Dunbar et al.
2010/0217116 A1 8/2010 Eck et al.
2010/0222664 A1 9/2010 Lemon et al.
2010/0222786 A1 9/2010 Kassab
2010/0234724 A1 9/2010 Jacobsen et al.
2010/0234733 A1 9/2010 Wahlheim
2010/0249598 A1 9/2010 Smith et al.
2010/0258033 A1 10/2010 Yang et al.
2010/0268059 A1 10/2010 Ryu et al.
2010/0273895 A1 10/2010 Stinchcomb et al.
2010/0274150 A1 10/2010 Harlev et al.
2010/0291521 A1 11/2010 Simon
2010/0298702 A1 11/2010 Rogers et al.
2010/0298704 A1 11/2010 Pelissier et al.
2010/0298705 A1 11/2010 Pelissier et al.
2010/0298712 A1 11/2010 Pelissier et al.
2010/0312086 A9 12/2010 Beatty et al.
2010/0317981 A1 12/2010 Grunwald
2010/0318026 A1 12/2010 Grunwald
2010/0331712 A1 12/2010 Rothenberg
2011/0002518 A1 1/2011 Ziv-Ari et al.
2011/0015496 A1 1/2011 Sherman et al.
2011/0015527 A1 1/2011 Heasty et al.
2011/0015533 A1 1/2011 Cox et al.
2011/0034823 A1 2/2011 Gelbart et al.
2011/0034940 A1 2/2011 Payner
2011/0040212 A1 2/2011 Dietz et al.
2011/0052694 A1 3/2011 Stinchcomb et al.
2011/0087105 A1 4/2011 Ridley et al.
2011/0087106 A1 4/2011 Ridley et al.
2011/0087107 A1 4/2011 Lindekugel et al.
2011/0106101 A1 5/2011 Tortonese et al.
2011/0112396 A1 5/2011 Shachar et al.
2011/0136242 A1 6/2011 Marx et al.
2011/0137156 A1 6/2011 Razzaque et al.
2011/0196235 A1 8/2011 Dunbar et al.
2011/0196248 A1 8/2011 Grunwald
2011/0196255 A1 8/2011 Kassab
2011/0224564 A1 9/2011 Moon et al.
2011/0237935 A1 9/2011 Kalpin et al.
2011/0245659 A1 10/2011 Ma et al.
2011/0263164 A1* 10/2011 Lenhert .................. H01R 13/33
267/167
2011/0282187 A1 11/2011 Harlev et al.
2011/0282188 A1 11/2011 Burnside et al.
2011/0282285 A1 11/2011 Blanchard et al.
2011/0282686 A1 11/2011 Venon et al.
2011/0295108 A1 12/2011 Cox et al.
2011/0306859 A1 12/2011 Saldivar et al.
2011/0306867 A1 12/2011 Gopinathan et al.
2011/0313293 A1 12/2011 Lindekugel et al.
2012/0004564 A1 1/2012 Dobak, III
2012/0016316 A1 1/2012 Zhuang et al.
2012/0035460 A1 2/2012 Stangenes et al.
2012/0035539 A1 2/2012 Tegg
2012/0046562 A1 2/2012 Powers et al.
2012/0059249 A1 3/2012 Verard et al.
2012/0059270 A1 3/2012 Grunwald
2012/0059271 A1 3/2012 Amitai et al.
2012/0071751 A1 3/2012 Sra et al.
2012/0071759 A1 3/2012 Hagy et al.
2012/0071782 A1 3/2012 Patil et al.
2012/0078342 A1 3/2012 Vollkron et al.
2012/0095319 A1 4/2012 Kondrosky et al.
2012/0108950 A1 5/2012 He et al.
2012/0115007 A1 5/2012 Felder et al.
2012/0136242 A1 5/2012 Qi et al.
2012/0143029 A1 6/2012 Silverstein et al.
2012/0143078 A1 6/2012 Kassab et al.
2012/0172727 A1 7/2012 Hastings et al.
2012/0197132 A1 8/2012 O'Connor
2012/0220854 A1 8/2012 Messerly et al.
2012/0220874 A1 8/2012 Hancock et al.
2012/0265084 A1 10/2012 Stewart et al.
2012/0283582 A1 11/2012 Mahapatra et al.
2012/0296200 A1 11/2012 Shachar et al.
2012/0296213 A1 11/2012 Mauldin, Jr. et al.
2012/0310052 A1 12/2012 Mahapatra et al.
2012/0310066 A1 12/2012 Shachar et al.
2012/0310660 A1 12/2012 Liu et al.
2012/0316440 A1 12/2012 Munrow et al.
2013/0006100 A1 1/2013 Shachar et al.
2013/0006102 A1 1/2013 Wilkes et al.
2013/0018248 A1 1/2013 Hurezan
2013/0018602 A1 1/2013 Ong et al.
2013/0035590 A1 2/2013 Ma et al.
2013/0041250 A1 2/2013 Pelissier et al.
2013/0041254 A1 2/2013 Hagy et al.
2013/0041269 A1 2/2013 Stahmann et al.
2013/0060116 A1 3/2013 Messerly et al.
2013/0079628 A1 3/2013 Groszmann et al.
2013/0085416 A1 4/2013 Mest
2013/0090938 A1 4/2013 Fishman et al.
2013/0102889 A1 4/2013 Southard et al.
2013/0102890 A1 4/2013 Dib
2013/0102967 A1 4/2013 Hanlon et al.
2013/0123597 A1 5/2013 Rothenberg
2013/0131502 A1 5/2013 Blaivas et al.
2013/0131503 A1 5/2013 Schneider et al.
2013/0150724 A1 6/2013 Blaivas et al.
2013/0169272 A1 7/2013 Eichler et al.
2013/0213147 A1 8/2013 Rice et al.
2013/0217999 A1 8/2013 Burnside et al.
2013/0223702 A1 8/2013 Holsing et al.
2013/0245434 A1 9/2013 Messerly et al.
2013/0281787 A1 10/2013 Avneri et al.
2013/0281837 A1 10/2013 Ridley et al.
2013/0289417 A1 10/2013 Grunwald et al.
2013/0296691 A1 11/2013 Ashe
2013/0296693 A1 11/2013 Wenzel et al.
2013/0303878 A1 11/2013 Nevo et al.
2013/0303896 A1 11/2013 Kalpin et al.
2013/0303945 A1 11/2013 Blumenkranz et al.
2013/0317338 A1 11/2013 Silverstein
2013/0324841 A1 12/2013 Kamen et al.
2013/0338503 A1 12/2013 Cohen et al.
2013/0338517 A1 12/2013 Rothenberg
2013/0345555 A1 12/2013 Kanade et al.
2014/0005530 A1 1/2014 Liu et al.
2014/0031674 A1 1/2014 Newman et al.
2014/0046261 A1 2/2014 Newman et al.
2014/0066798 A1 3/2014 Albert
2014/0073976 A1 3/2014 Fonte et al.
2014/0089836 A1 3/2014 Damani et al.
2014/0094694 A1 4/2014 Moctezuma de la Barrera
2014/0094768 A1 4/2014 Stangenes et al.
2014/0107475 A1 4/2014 Cox et al.
2014/0128712 A1 5/2014 Banet et al.
2014/0163356 A2 6/2014 Burnside et al.
2014/0163382 A1 6/2014 Gubbini et al.
2014/0180074 A1 6/2014 Green et al.
2014/0180098 A1 6/2014 Flaherty et al.
2014/0187917 A1 7/2014 Clark et al.
2014/0187990 A1 7/2014 Banet et al.
2014/0188133 A1 7/2014 Misener
2014/0221862 A1 8/2014 Tambe
2014/0228689 A1 8/2014 Ishikawa et al.
2014/0243659 A1 8/2014 Rothenberg
2014/0249428 A1 9/2014 Ingold, Jr. et al.
2014/0249505 A1 9/2014 Bukhman
2014/0253270 A1 9/2014 Nicholls et al.
2014/0257080 A1 9/2014 Dunbar et al.
2014/0275957 A1 9/2014 Lupotti
2014/0275990 A1 9/2014 Hagy et al.
2014/0276010 A1 9/2014 Anderson
2014/0276059 A1 9/2014 Sheehan
2014/0276081 A1 9/2014 Tegels

(56) References Cited

U.S. PATENT DOCUMENTS

| | | | |
|---|---|---|---|
| 2014/0303492 A1 | 10/2014 | Burnside et al. | |
| 2014/0309624 A1 | 10/2014 | Bown et al. | |
| 2014/0343398 A1 | 11/2014 | He et al. | |
| 2014/0343431 A1 | 11/2014 | Vajinepalli et al. | |
| 2015/0005621 A1 | 1/2015 | Liu | |
| 2015/0011887 A1 | 1/2015 | Ahn et al. | |
| 2015/0018701 A1 | 1/2015 | Cox et al. | |
| 2015/0025365 A1 | 1/2015 | Esguerra Wilczynski et al. | |
| 2015/0025402 A1 | 1/2015 | Rothenberg | |
| 2015/0051489 A1 | 2/2015 | Caluser et al. | |
| 2015/0065916 A1 | 3/2015 | Maguire et al. | |
| 2015/0073279 A1 | 3/2015 | Cai et al. | |
| 2015/0073285 A1 | 3/2015 | Albert et al. | |
| 2015/0080716 A1 | 3/2015 | Powers et al. | |
| 2015/0173723 A1 | 6/2015 | Bates et al. | |
| 2015/0209008 A1 | 7/2015 | Ridley et al. | |
| 2015/0209113 A1 | 7/2015 | Burkholz et al. | |
| 2015/0209526 A1 | 7/2015 | Matsubara et al. | |
| 2015/0216445 A1 | 8/2015 | Carmeli et al. | |
| 2015/0216446 A1 | 8/2015 | Bukhman et al. | |
| 2015/0223775 A1 | 8/2015 | Hamilton, Jr. | |
| 2015/0245809 A1 | 9/2015 | Hagy et al. | |
| 2015/0245872 A1 | 9/2015 | Hagy et al. | |
| 2015/0246247 A1 | 9/2015 | Binnekamp et al. | |
| 2015/0282734 A1 | 10/2015 | Schweikert et al. | |
| 2015/0289781 A1 | 10/2015 | Grunwald et al. | |
| 2015/0297097 A1 | 10/2015 | Matsubara et al. | |
| 2015/0297114 A1 | 10/2015 | Cox et al. | |
| 2015/0317810 A1 | 11/2015 | Grunwald et al. | |
| 2015/0335310 A1 | 11/2015 | Bernstein et al. | |
| 2015/0335383 A9 | 11/2015 | Cohen | |
| 2016/0000399 A1 | 1/2016 | Halmann et al. | |
| 2016/0067449 A1 | 3/2016 | Misener et al. | |
| 2016/0120607 A1 | 5/2016 | Sorotzkin et al. | |
| 2016/0166232 A1 | 6/2016 | Merritt | |
| 2016/0202053 A1 | 7/2016 | Walker et al. | |
| 2016/0278869 A1 | 9/2016 | Grunwald | |
| 2016/0296208 A1 | 10/2016 | Sethuraman et al. | |
| 2016/0331344 A1 | 11/2016 | Hadzic | |
| 2016/0374589 A1 | 12/2016 | Misener et al. | |
| 2016/0374644 A1 | 12/2016 | Mauldin, Jr. et al. | |
| 2017/0000367 A1 | 1/2017 | Grunwald | |
| 2017/0020561 A1 | 1/2017 | Cox et al. | |
| 2017/0079548 A1 | 3/2017 | Silverstein et al. | |
| 2017/0079552 A1 | 3/2017 | Grunwald | |
| 2017/0079615 A1 | 3/2017 | Burnside et al. | |
| 2017/0079681 A1 | 3/2017 | Burnside et al. | |
| 2017/0086782 A1 | 3/2017 | Hagy et al. | |
| 2017/0151022 A1 | 6/2017 | Jascob et al. | |
| 2017/0151027 A1 | 6/2017 | Walker et al. | |
| 2017/0215762 A1 | 8/2017 | Burnside et al. | |
| 2017/0231700 A1 | 8/2017 | Cox et al. | |
| 2017/0238996 A1* | 8/2017 | Frame | A61B 34/20 |
| 2017/0281029 A1 | 10/2017 | Messerly et al. | |
| 2017/0347914 A1* | 12/2017 | Isaacson | A61B 8/0841 |
| 2017/0348510 A1 | 12/2017 | Shevgoor et al. | |
| 2017/0348511 A1 | 12/2017 | Burkholz et al. | |
| 2017/0367678 A1 | 12/2017 | Sirtori et al. | |
| 2018/0042577 A1 | 2/2018 | Perrey et al. | |
| 2018/0070856 A1 | 3/2018 | Grunwald | |
| 2018/0103869 A1 | 4/2018 | Bukhman et al. | |
| 2018/0116551 A1 | 5/2018 | Newman et al. | |
| 2018/0116723 A1 | 5/2018 | Hettrick et al. | |
| 2018/0116744 A1* | 5/2018 | Taya | A61B 34/32 |
| 2018/0125450 A1 | 5/2018 | Blackbourne et al. | |
| 2018/0145443 A1 | 5/2018 | Andreason et al. | |
| 2018/0161012 A1 | 6/2018 | Bang et al. | |
| 2018/0161502 A1 | 6/2018 | Nanan et al. | |
| 2018/0169389 A1 | 6/2018 | Lemon et al. | |
| 2018/0199914 A1 | 7/2018 | Ramachandran et al. | |
| 2018/0214119 A1 | 8/2018 | Mehrmohammadi et al. | |
| 2018/0220995 A1 | 8/2018 | Pelissier et al. | |
| 2018/0296122 A1 | 10/2018 | Messerly et al. | |
| 2018/0304043 A1 | 10/2018 | Bown et al. | |
| 2018/0310955 A1 | 11/2018 | Lindekugel et al. | |
| 2018/0325604 A1 | 11/2018 | Atarot et al. | |
| 2018/0333559 A1 | 11/2018 | Makey | |
| 2019/0069877 A1 | 3/2019 | Burnside et al. | |
| 2019/0099108 A1 | 4/2019 | Messerly et al. | |
| 2019/0216423 A1 | 7/2019 | Ko et al. | |
| 2019/0246945 A1 | 8/2019 | Grunwald | |
| 2019/0261886 A1 | 8/2019 | King et al. | |
| 2019/0290208 A1 | 9/2019 | Toth et al. | |
| 2019/0320982 A1 | 10/2019 | Misener et al. | |
| 2020/0054858 A1 | 2/2020 | Newman et al. | |
| 2020/0119488 A1 | 4/2020 | Stats et al. | |
| 2020/0138332 A1 | 5/2020 | Newman et al. | |
| 2020/0237255 A1 | 7/2020 | Silverstein et al. | |
| 2020/0237403 A1 | 7/2020 | Southard et al. | |
| 2020/0246588 A1 | 8/2020 | Akins et al. | |
| 2020/0345983 A1 | 11/2020 | Misener | |
| 2021/0077061 A1 | 3/2021 | Pinkovich et al. | |
| 2021/0077201 A1 | 3/2021 | Cox et al. | |
| 2021/0082860 A1* | 3/2021 | Audette | H01L 24/11 |
| 2021/0259575 A1 | 8/2021 | Burnside et al. | |
| 2021/0307838 A1 | 10/2021 | Xia et al. | |
| 2021/0353173 A1 | 11/2021 | Newman et al. | |
| 2021/0401456 A1 | 12/2021 | Cox et al. | |
| 2022/0347433 A1 | 11/2022 | Davis et al. | |
| 2023/0233262 A9 | 7/2023 | Cox et al. | |

FOREIGN PATENT DOCUMENTS

| | | | |
|---|---|---|---|
| AU | 1860597 | B2 | 6/1999 |
| AU | 20009592 | | 9/2000 |
| AU | 20015250 | | 6/2001 |
| AU | 768362 | B2 | 12/2003 |
| AU | 2001229024 | B2 | 9/2005 |
| AU | 2001283703 | B2 | 5/2006 |
| AU | 2006904933 | | 9/2006 |
| AU | 2006202149 | B2 | 3/2009 |
| AU | 2006283022 | B2 | 2/2012 |
| CA | 1197745 | A | 12/1985 |
| CA | 2420676 | C | 7/2010 |
| CA | 2619909 | C | 1/2014 |
| CN | 2031655 | U | 2/1989 |
| CN | 1672649 | A | 9/2005 |
| CN | 1913833 | A | 2/2007 |
| CN | 102209490 | A | 10/2011 |
| CN | 102802514 | A | 11/2012 |
| CN | 102821679 | A | 12/2012 |
| CN | 103037761 | A | 4/2013 |
| CN | 103037762 | A | 4/2013 |
| CN | 103118591 | A | 5/2013 |
| CN | 103189009 | A | 7/2013 |
| CN | 104013425 | A | 9/2014 |
| DE | 4319033 | C1 | 6/1994 |
| EP | 0153021 | A1 | 8/1985 |
| EP | 0362821 | A1 | 4/1990 |
| EP | 0399536 | A1 | 11/1990 |
| EP | 0359697 | B1 | 11/1994 |
| EP | 0823261 | A2 | 2/1998 |
| EP | 0928976 | A2 | 7/1999 |
| EP | 1025805 | A1 | 8/2000 |
| EP | 1015967 | B1 | 4/2002 |
| EP | 1311226 | A1 | 5/2003 |
| EP | 1504713 | A1 | 2/2005 |
| EP | 1117331 | B1 | 5/2005 |
| EP | 1117332 | B1 | 8/2005 |
| EP | 1118019 | B1 | 5/2006 |
| EP | 1717601 | A2 | 11/2006 |
| EP | 1887940 | A2 | 2/2008 |
| EP | 1932477 | A1 | 6/2008 |
| EP | 2337491 | A1 | 6/2011 |
| EP | 2440122 | A1 | 4/2012 |
| EP | 2464407 | A2 | 6/2012 |
| EP | 2482719 | A1 | 8/2012 |
| EP | 2531098 | A1 | 12/2012 |
| EP | 2575610 | A1 | 4/2013 |
| EP | 2575611 | A1 | 4/2013 |
| EP | 2603145 | A2 | 6/2013 |
| EP | 2605699 | A2 | 6/2013 |
| EP | 2474268 | B1 | 7/2013 |
| EP | 2618727 | A1 | 7/2013 |

(56) References Cited

FOREIGN PATENT DOCUMENTS

| | | | |
|---|---|---|---|
| EP | 2632360 | A1 | 9/2013 |
| EP | 2219526 | B1 | 3/2014 |
| EP | 2712547 | A1 | 4/2014 |
| EP | 2313143 | B1 | 9/2014 |
| EP | 2913000 | A2 | 9/2015 |
| EP | 2992825 | B1 | 5/2017 |
| EP | 2170162 | B1 | 8/2017 |
| EP | 2265175 | B1 | 8/2017 |
| FR | 2545349 | B1 | 9/1986 |
| IN | 101854853 | A | 10/2010 |
| JP | 01097440 | | 4/1989 |
| JP | 03173542 | A | 7/1991 |
| JP | 9-503054 | | 3/1997 |
| JP | 09-094298 | A | 4/1997 |
| JP | 10043310 | | 2/1998 |
| JP | 10290839 | A | 11/1998 |
| JP | H114829 | A | 1/1999 |
| JP | 11128237 | A | 5/1999 |
| JP | 2001-145630 | A | 5/2001 |
| JP | 2001161683 | A | 6/2001 |
| JP | 2001-514533 | A | 9/2001 |
| JP | 2001-524339 | A | 12/2001 |
| JP | 2001340334 | A | 12/2001 |
| JP | 2002520893 | A | 7/2002 |
| JP | 2002-224069 | A | 8/2002 |
| JP | 2002-529133 | A | 9/2002 |
| JP | 2002-541947 | A | 12/2002 |
| JP | 2003-010138 | A | 1/2003 |
| JP | 2003501127 | A | 1/2003 |
| JP | 2003061752 | A | 3/2003 |
| JP | 2003299654 | A | 10/2003 |
| JP | 2003334191 | A | 11/2003 |
| JP | 2004505748 | T | 2/2004 |
| JP | 2004515298 | A | 5/2004 |
| JP | 2006508744 | A | 3/2006 |
| JP | 2006-338526 | A | 12/2006 |
| JP | 2007-000226 | A | 1/2007 |
| JP | 2007-068989 | A | 3/2007 |
| JP | 2007-105450 | A | 4/2007 |
| JP | 2007-313122 | A | 12/2007 |
| JP | 4090741 | B2 | 5/2008 |
| JP | 2008196593 | A | 8/2008 |
| JP | 2009/271123 | A | 11/2009 |
| JP | 5010604 | B2 | 8/2012 |
| JP | 2012-529929 | A | 11/2012 |
| JP | 2013-518676 | A | 5/2013 |
| JP | 2013-526959 | A | 6/2013 |
| JP | 2013-526961 | A | 6/2013 |
| KR | 20100047436 | A | 5/2010 |
| RU | 2009101949 | A | 7/2010 |
| WO | 1980002376 | A1 | 11/1980 |
| WO | 1991012836 | A1 | 9/1991 |
| WO | 1992003090 | A1 | 3/1992 |
| WO | 1994003159 | A1 | 2/1994 |
| WO | 1994004938 | A1 | 3/1994 |
| WO | 1996005768 | A1 | 2/1996 |
| WO | 1996007352 | A1 | 3/1996 |
| WO | 1996041119 | A1 | 12/1996 |
| WO | 1997/22395 | A1 | 6/1997 |
| WO | 1997029683 | A1 | 8/1997 |
| WO | 1997043989 | A1 | 11/1997 |
| WO | 97/48438 | A2 | 12/1997 |
| WO | 1998025159 | A1 | 6/1998 |
| WO | 98/29032 | A1 | 7/1998 |
| WO | 1998035611 | A1 | 8/1998 |
| WO | 1999016495 | A1 | 4/1999 |
| WO | 1999027837 | A2 | 6/1999 |
| WO | 1999049407 | A1 | 9/1999 |
| WO | 2000019906 | A1 | 4/2000 |
| WO | 2000027281 | A1 | 5/2000 |
| WO | 2000040155 | A1 | 7/2000 |
| WO | 2000063658 | A2 | 10/2000 |
| WO | 2000074775 | A1 | 12/2000 |
| WO | 2001013792 | A1 | 3/2001 |
| WO | 2001039683 | A1 | 6/2001 |
| WO | 2001076479 | A1 | 10/2001 |
| WO | 02/07794 | A2 | 1/2002 |
| WO | 2002015973 | A1 | 2/2002 |
| WO | 2002019905 | A1 | 3/2002 |
| WO | 2002025277 | A1 | 3/2002 |
| WO | 2002085442 | A1 | 10/2002 |
| WO | 2003061752 | A1 | 7/2003 |
| WO | 2003077759 | A1 | 9/2003 |
| WO | 03/088833 | A1 | 10/2003 |
| WO | 2003091495 | A1 | 11/2003 |
| WO | 2004002303 | A1 | 1/2004 |
| WO | 2004049970 | A2 | 6/2004 |
| WO | 2005033524 | A1 | 4/2005 |
| WO | 2005033574 | A1 | 4/2005 |
| WO | 2005/089851 | A1 | 9/2005 |
| WO | 2005117690 | A1 | 12/2005 |
| WO | 2005117733 | A2 | 12/2005 |
| WO | 2006074509 | A1 | 7/2006 |
| WO | 2006074510 | A1 | 7/2006 |
| WO | 2006078677 | A2 | 7/2006 |
| WO | 2006103661 | A2 | 10/2006 |
| WO | 2006111056 | A1 | 10/2006 |
| WO | 2006122001 | A2 | 11/2006 |
| WO | 2007002541 | A2 | 1/2007 |
| WO | 2007005976 | A1 | 1/2007 |
| WO | 2007014447 | A1 | 2/2007 |
| WO | 2007034196 | A2 | 3/2007 |
| WO | 2007067324 | A1 | 6/2007 |
| WO | 2007069168 | A2 | 6/2007 |
| WO | 2007109123 | A2 | 9/2007 |
| WO | 2007126536 | A2 | 11/2007 |
| WO | 2007144894 | A1 | 12/2007 |
| WO | 2008005480 | A1 | 1/2008 |
| WO | 2008024596 | A2 | 2/2008 |
| WO | 2008028253 | A1 | 3/2008 |
| WO | 2008083111 | A1 | 7/2008 |
| WO | 2008097767 | A2 | 8/2008 |
| WO | 2008118992 | A1 | 10/2008 |
| WO | 2008126074 | A2 | 10/2008 |
| WO | 2008129326 | A1 | 10/2008 |
| WO | 2008131017 | A2 | 10/2008 |
| WO | 2008136008 | A2 | 11/2008 |
| WO | 2009000439 | A1 | 12/2008 |
| WO | 2009002514 | A2 | 12/2008 |
| WO | 2009003138 | A1 | 12/2008 |
| WO | 2009009064 | A1 | 1/2009 |
| WO | 2009057774 | A1 | 5/2009 |
| WO | 2009063166 | A1 | 5/2009 |
| WO | 2009067654 | A1 | 5/2009 |
| WO | 2009070616 | A2 | 6/2009 |
| WO | 2009100158 | A1 | 8/2009 |
| WO | 2009123819 | A2 | 10/2009 |
| WO | 2009126340 | A1 | 10/2009 |
| WO | 2009129475 | A1 | 10/2009 |
| WO | 2009129477 | A1 | 10/2009 |
| WO | 2009134605 | A2 | 11/2009 |
| WO | 2009137262 | A2 | 11/2009 |
| WO | 2010002313 | A1 | 1/2010 |
| WO | 2010/022370 | A1 | 2/2010 |
| WO | 2010018500 | A1 | 2/2010 |
| WO | 2010027349 | A1 | 3/2010 |
| WO | 2010027471 | A2 | 3/2010 |
| WO | 2010029906 | A1 | 3/2010 |
| WO | 2010030820 | A1 | 3/2010 |
| WO | 2010132857 | A1 | 11/2010 |
| WO | 2010132985 | A1 | 11/2010 |
| WO | 2010/144922 | A1 | 12/2010 |
| WO | 2010143196 | A1 | 12/2010 |
| WO | 2011019760 | A2 | 2/2011 |
| WO | 2011041450 | A1 | 4/2011 |
| WO | 2011044421 | A1 | 4/2011 |
| WO | 2011057289 | A2 | 5/2011 |
| WO | 2011064209 | A1 | 6/2011 |
| WO | 2011084593 | A2 | 7/2011 |
| WO | 2011097312 | A1 | 8/2011 |
| WO | 2011128052 | A2 | 10/2011 |
| WO | 2011150358 | A1 | 12/2011 |
| WO | 2011150376 | A1 | 12/2011 |
| WO | 2012021542 | A2 | 2/2012 |

(56) References Cited

FOREIGN PATENT DOCUMENTS

| | | | |
|---|---|---|---|
| WO | 2012024577 | A2 | 2/2012 |
| WO | 2012039866 | A1 | 3/2012 |
| WO | 2012040487 | A1 | 3/2012 |
| WO | 2012058461 | A1 | 5/2012 |
| WO | 2012083245 | A1 | 6/2012 |
| WO | 2012088535 | A1 | 6/2012 |
| WO | 2012110955 | A1 | 8/2012 |
| WO | 2012173697 | A1 | 12/2012 |
| WO | 2013006713 | A2 | 1/2013 |
| WO | 2013006817 | A1 | 1/2013 |
| WO | 2013034175 | A1 | 3/2013 |
| WO | 2014042329 | A1 | 3/2014 |
| WO | 2014/062728 | A1 | 4/2014 |
| WO | 2014052894 | A2 | 4/2014 |
| WO | 2014072238 | A1 | 5/2014 |
| WO | 2014137977 | A1 | 9/2014 |
| WO | 2014138652 | A1 | 9/2014 |
| WO | 2014138918 | A1 | 9/2014 |
| WO | 2015/055797 | A1 | 4/2015 |
| WO | 2015048514 | A1 | 4/2015 |
| WO | 2015073962 | A1 | 5/2015 |
| WO | 2015/120256 | A2 | 8/2015 |
| WO | 2016/210325 | A1 | 12/2016 |
| WO | 2017079732 | A1 | 5/2017 |
| WO | 2017096487 | A1 | 6/2017 |
| WO | 2017214428 | A1 | 12/2017 |
| WO | 2018/112252 | A1 | 6/2018 |
| WO | 2018134726 | A1 | 7/2018 |
| WO | 2020/160315 | A1 | 8/2020 |
| WO | 2022232325 | A1 | 11/2022 |

OTHER PUBLICATIONS

EP 10821193.9 filed Mar. 27, 2012 Partial European Search Report dated Oct. 9, 2015.
EP 11 818 828.3 filed Mar. 18, 2013 Extended European Search Report dated Dec. 10, 2014.
EP 11740309.7 filed Aug. 23, 2012 Extended European Search Report dated Aug. 3, 2015.
EP 11787515.3 filed Dec. 12, 2012 partial European search report dated Jun. 23, 2015.
EP 11787515.3 filed Dec. 12, 2012 partial European search report dated Oct. 27, 2015.
EP 11787527.8 filed Dec. 19, 2012 Extended European Search Report dated Oct. 9, 2015.
EP 11787527.8 filed Dec. 19, 2012 partial European search report dated May 26, 2015.
EP 11827551.0 filed Feb. 7, 2013 Extended European Search Report dated Sep. 19, 2017.
EP 11827551.0 filed Feb. 7, 2013 Office Action dated Mar. 13, 2020.
EP 11837113.7 filed May 28, 2013 Extended European Search Report dated Apr. 24, 2014.
EP 11850625.2 filed Jul. 22, 2013 Extended European Search Report dated Jun. 21, 2017.
EP 11850625.2 filed Jul. 22, 2013 Office Action dated Feb. 25, 2019.
EP 11850625.2 filed Jul. 22, 2013 Office Action dated Sep. 24, 2018.
EP 12177438.4 filed Jul. 23, 2012 Communication dated Jan. 13, 2014.
EP 12177438.4 filed Jul. 23, 2012 European Search Report dated Dec. 4, 2012.
EP 12177438.4 filed Jul. 23, 2012 European Search Report dated Jun. 7, 2015.
EP 12177438.4 filed Jul. 23, 2012 Examination Report dated Dec. 5, 2014.
EP 12177438.4 filed Jul. 23, 2012 extended European Search Report dated Mar. 25, 2013.
EP 12807886.2 filed Jan. 15, 2014 Extended European Search Report dated Februry 6, 2015.
EP 13194818.4 filed Nov. 28, 2013 extended European search report dated Feb. 28, 2014.
EP 13840356.3 filed Apr. 27, 2015 Extended European Search Report dated Mar. 22, 2017.
EP 13840356.3 filed Apr. 27, 2015 Partial European Search Report dated Oct. 19, 2016.
EP 13846380.7 filed May 15, 2015 Extended European Search Report dated Sep. 30, 2016.
EP 13846380.7 filed May 15, 2015 Partial European Search Report dated Sep. 30, 2016.
EP 14151268.1 filed Jan. 15, 2014 European Search Report dated Feb. 21, 2014.
EP 14197137.4 filed Dec. 10, 2014 Extended European Search Report dated Nov. 4, 2015.
EP 14197137.4 filed Dec. 10, 2014 Office Action dated Apr. 5, 2018.
EP 14197137.4 filed Dec. 10, 2014 Office Action dated, Sep. 20, 2017.
EP 14197137.4 filed Dec. 10, 2014, Office Action dated Nov. 21, 2018.
EP 14197137.4 filed Dec. 10, 2014, Partial European Search Report dated May 29, 2015.
EP 14761249.3 Filed Sep. 3, 2015 Extended European Search Report dated Sep. 19, 2016.
EP 14761249.3 Filed Sep. 3, 2015 Office Action dated Sep. 28, 2017.
EP 15179061.5 filed Jul. 30, 2015 Extended European Search Report dated Jan. 14, 2016.
EP 15179061.5 filed Jul. 30, 2015 Partial European Search Report dated Jan. 17, 2018.
EP 15746326.6 filed Jul. 1, 2016 Extended European Search Report dated Jun. 9, 2017.
EP 15746326.6 filed Jul. 1, 2016 Office Action dated Jan. 29, 2019.
EP 17157118.5 filed Feb. 21, 2017 Extended European Search Report Jun. 8, 2017.
EP 17186624.7 filed Aug. 17, 2017 Extended European Search Report dated Jan. 17, 2018.
EP 17186624.7 filed Aug. 17, 2017 Partial European Search Report dated Jan. 17, 2018.
EP 20154593.6 filed Jan. 30, 2020 Extended European Search Report dated Jun. 2, 2020.
EP14197136.6 filed Dec. 10, 2014 Extended European Search Report dated May 26, 2015.
EP14197136.6 filed Dec. 10, 2014 Office Action dated Nov. 21, 2018.
Fearon, William F et al, Evaluating Intermediate Coronary Lesions in the Cardiac Catheterization Laboratory, vol. 4, No. 1, 7 pages, Reviews in Cardiovascular Medicine, 2003.
Felleiter P et al, Use of Electrocardiogramacement Control of Central Venous Catheters in Austria, Acta Med Austriaca, pp. 109-113, vol. 26 No 3, 1999 (Abstract only).
Forauer, AR et al, Change in Peripherally Inserted Central Catheter Tip Location with Abduction and Adduction of the Upper Extremity, J Vasc Interv Radiol, pp. 1315-1318, vol. 11 No. 10, Nov.-Dec. 2000.
Frassinelli, P et al, Utility of Chest Radiographs after Guidewire Exchanges of Central Venous Catheters, Crit Care Med, pp. 611-615, vol. 26 No 3, Mar. 1998.
Frazin L et al, A Doppler Guided Retrograde Catheterization System, Cathet. Cardiovasc Diagn, pp. 41-50, May 1992.
French, PJ et al, Sensors for Catheter Applications, Sensors Update, vol. 13 Issue 1 pp. 107-153, Dec. 2003.
GB Application 0800474.9 filed Aug. 24, 2006 Office Action dated Aug. 9, 2010.
U.S. Appl. No. 13/469,932, filed May 11, 2012 Non-Final Office Action dated Jan. 3, 2014.
U.S. Appl. No. 13/469,932, filed May 11, 2012 Non-Final Office Action dated Jul. 31, 2014.
U.S. Appl. No. 13/469,932, filed May 11, 2012 Non-Final Office Action dated Sep. 4, 2015.
U.S. Appl. No. 13/469,932, filed May 11, 2012 Notice of Allowance dated Jan. 31, 2017.
U.S. Appl. No. 13/469,932, filed May 11, 2012 Final Office Action dated Apr. 7, 2016.
U.S. Appl. No. 13/665,420, filed Oct. 31, 2012 Final Office Action dated Apr. 8, 2016.

(56) References Cited

OTHER PUBLICATIONS

U.S. Appl. No. 13/665,420, filed Oct. 31, 2012 Non-Final Office Action dated Jan. 6, 2014.
U.S. Appl. No. 13/665,420, filed Oct. 31, 2012 Non-Final Office Action dated Jul. 9, 2015.
U.S. Appl. No. 13/665,420, filed Oct. 31, 2012 Non-Final Office Action dated Mar. 15, 2017.
U.S. Appl. No. 13/665,420, filed Oct. 31, 2012 Non-Final Office Action dated Oct. 9, 2014.
U.S. Appl. No. 13/665,420, filed Oct. 31, 2012 Notice of Allowance dated Feb. 7, 2018.
U.S. Appl. No. 13/737,806, filed Jan. 9, 2013 Notice of Allowance dated Oct. 31, 2013.
U.S. Appl. No. 13/858,782, filed Apr. 8, 2013 Notice of Allowance dated Oct. 9, 2014.
U.S. Appl. No. 13/887,166, filed May 3, 2013 Advisory Action dated Aug. 27, 2014.
U.S. Appl. No. 13/887,166, filed May 3, 2013 Appeal Decision dated Aug. 17, 2017.
U.S. Appl. No. 13/887,166, filed May 3, 2013 Examiner's Answer dated Jul. 16, 2015.
U.S. Appl. No. 13/887,166, filed May 3, 2013 Final Office Action dated Jun. 23, 2014.
U.S. Appl. No. 13/887,166, filed May 3, 2013 Non-Final Office Action dated Jan. 7, 2014.
U.S. Appl. No. 13/887,166, filed May 3, 2013 Notice of Allowance dated Nov. 6, 2017.
U.S. Appl. No. 13/890,158, filed May 8, 2013 Advisory Action dated Feb. 13, 2018.
U.S. Appl. No. 13/890,158, filed May 8, 2013 Advisory Action dated Jul. 26, 2016.
U.S. Appl. No. 13/890,158, filed May 8, 2013 Final Office Action dated Nov. 21, 2017.
U.S. Appl. No. 13/890,158, filed May 8, 2013 Non-Final Office Action dated Apr. 7, 2017.
U.S. Appl. No. 13/890,158, filed May 8, 2013 Non-Final Office Action dated Aug. 15, 2014.
U.S. Appl. No. 13/890,158, filed May 8, 2013 Non-Final Office Action dated Jul. 9, 2015.
U.S. Appl. No. 13/890,158, filed May 8, 2013 Notice of Allowance dated May 30, 2018.
U.S. Appl. No. 13/969,265, filed Aug. 16, 2013 Non-Final Office Action dated Dec. 19, 2013.
U.S. Appl. No. 13/969,265, filed Aug. 16, 2013 Notice of Allowance dated Jun. 23, 2014.
U.S. Appl. No. 14/040,205, filed Sep. 27, 2013 Advisory Action dated Dec. 15, 2016.
U.S. Appl. No. 14/040,205, filed Sep. 27, 2013 Board Decision dated May 1, 2019.
U.S. Appl. No. 14/040,205, filed Sep. 27, 2013 Examiner's Answer dated Jul. 20, 2017.
U.S. Appl. No. 14/040,205, filed Sep. 27, 2013 Final Office Action dated Oct. 19, 2016.
U.S. Appl. No. 14/040,205, filed Sep. 27, 2013 Non-Final Office Action dated Mar. 10, 2016.
U.S. Appl. No. 14/040,205, filed Sep. 27, 2013 Notice of Allowance dated Aug. 21, 2019.
U.S. Appl. No. 14/054,700, filed Oct. 15, 2013 Advisory Action dated Dec. 15, 2016.
U.S. Appl. No. 14/054,700, filed Oct. 15, 2013 Board Decision dated May 1, 2019.
U.S. Appl. No. 14/054,700, filed Oct. 15, 2013 Examiner's Answer dated Jul. 3, 2017.
U.S. Appl. No. 14/054,700, filed Oct. 15, 2013 Final Office Action dated Oct. 19, 2016.
U.S. Appl. No. 14/054,700, filed Oct. 15, 2013 Notice of Allowance dated Jun. 6, 2019.
U.S. Appl. No. 14/141,046, filed Dec. 26, 2013 Advisory Action dated Aug. 4, 2016.
U.S. Appl. No. 14/141,046, filed Dec. 26, 2013 Board Decision dated Nov. 26, 2019.
U.S. Appl. No. 14/141,046, filed Dec. 26, 2013 Examiner's Answer dated Oct. 15, 2018.
U.S. Appl. No. 14/141,046, filed Dec. 26, 2013 Final Office Action dated Dec. 11, 2017.
U.S. Appl. No. 14/141,046, filed Dec. 26, 2013 Final Office Action dated May 11, 2016.
U.S. Appl. No. 14/141,046, filed Dec. 26, 2013 Non-Final Office Action dated Apr. 7, 2017.
U.S. Appl. No. 14/141,046, filed Dec. 26, 2013 Non-Final Office Action dated Feb. 11, 2015.
U.S. Appl. No. 14/141,046, filed Dec. 26, 2013 Non-Final Office Action dated Jun. 20, 2014.
U.S. Appl. No. 14/141,046, filed Dec. 26, 2013 Non-Final Office Action dated Nov. 5, 2015.
U.S. Appl. No. 14/141,046, filed Dec. 26, 2013 Notice of Allowance dated May 12, 2021.
U.S. Appl. No. 14/201,300, filed Mar. 7, 2014 Advisory Action dated Jul. 18, 2016.
PCT/US2009/033116 filed Feb. 4, 2009 Written Opinion dated Mar. 13, 2009.
PCT/US2009/041051 filed Apr. 17, 2009 International Preliminary Report on Patentability dated Apr. 8, 2014.
PCT/US2009/041051 filed Apr. 17, 2009 Search Report dated Jul. 28, 2009.
PCT/US2009/041051 filed Apr. 17, 2009 Written Opinion dated Jul. 28, 2009.
PCT/US2009/054687 filed Aug. 21, 2009 International Preliminary Report on Patentability dated Feb. 22, 2011.
PCT/US2009/054687 filed Aug. 21, 2009 Search Report dated Oct. 6, 2009.
PCT/US2009/054687 filed Aug. 21, 2009 Written Opinion dated Oct. 6, 2009.
PCT/US2009/056567 filed Sep. 10, 2009 International Preliminary Report on Patentability dated Mar. 15, 2011.
PCT/US2009/056567 filed Sep. 10, 2009 Search Report dated Nov. 6, 2009.
PCT/US2009/056567 filed Sep. 10, 2009 Written Opinion dated Nov. 6, 2009.
PCT/US2010/038555 filed Jun. 14, 2010 Search Report dated Oct. 5, 2010.
PCT/US2010/038555 filed Jun. 14, 2010 Written Opinion dated Oct. 5, 2010.
PCT/US2010/045084 filed Aug. 10, 2010 International Preliminary Report on Patentability dated Feb. 23, 2012.
PCT/US2010/045084 filed Aug. 10, 2010 Search Report dated Apr. 14, 2011.
PCT/US2010/045084 filed Aug. 10, 2010 Written Opinion dated Apr. 14, 2011.
PCT/US2010/050773 filed Sep. 29, 2010 Search Report dated Jan. 24, 2011.
PCT/US2010/050773 filed Sep. 29, 2010 Written Opinion dated Jan. 24, 2011.
PCT/US2010/051917 filed Oct. 8, 2010 Search Report dated Nov. 29, 2010.
PCT/US2010/051917 filed Oct. 8, 2010 Written Opinion dated Nov. 29, 2010.
PCT/US2011/023497 filed Feb. 2, 2011 Search Report dated Jun. 6, 2011.
PCT/US2011/023497 filed Feb. 2, 2011 Written Opinion dated Jun. 6, 2011.
PCT/US2011/038391 filed May 27, 2011 International Preliminary Report on Patentability and Written Opinion dated Dec. 4, 2012.
PCT/US2011/038391 filed May 27, 2011 International Search Report dated Sep. 21, 2011.
PCT/US2011/038415 filed May 27, 2011 International Preliminary Report on Patentability dated Dec. 13, 2012.
PCT/US2011/038415 filed May 27, 2011 International Search Report dated Sep. 28, 2011.
PCT/US2011/038415 filed May 27, 2011 Written Opinion dated Sep. 28, 2011.

(56) References Cited

OTHER PUBLICATIONS

PCT/US2011/047127 filed Aug. 9, 2011 International Preliminary Report on Patentability dated Apr. 18, 2013.
PCT/US2011/047127 filed Aug. 9, 2011 International Search Report dated Feb. 29, 2012.
PCT/US2011/047127 filed Aug. 9, 2011 Written Opinion dated Feb. 29, 2012.
PCT/US2011/048403 filed Aug. 19, 2011 International Preliminary Report on Patentability dated Jul. 30, 2013.
PCT/US2011/048403 filed Aug. 19, 2011 International Search Report dated Dec. 15, 2011.
PCT/US2011/048403 filed Aug. 19, 2011 Written Opinion dated Dec. 15, 2011.
PCT/US2011/052793 filed Sep. 22, 2011 International Preliminary Report on Patentability dated Apr. 4, 2013.
PCT/US2011/052793 filed Sep. 22, 2011 International Search Report dated Jan. 6, 2012.
PCT/US2011/052793 filed Sep. 22, 2011 Written Opinion dated Jan. 6, 2012.
PCT/US2011/058138 filed Oct. 27, 2011 International Preliminary Report on Patentability dated May 10, 2013.
PCT/US2011/058138 filed Oct. 27, 2011 International Search Report dated Feb. 7, 2012.
PCT/US2011/058138 filed Oct. 27, 2011 Written Opinion dated Feb. 7, 2012.
PCT/US2011/067268 filed Dec. 23, 2011 International Preliminary Report on Patentability dated Jul. 4, 2013.
PCT/US2011/067268 filed Dec. 23, 2011 International Search Report and Written Opinion dated Apr. 27, 2012.
PCT/US2012/045814 filed Jul. 6, 2012 International Search Report and Written Opinion dated Oct. 1, 2012.
PCT/US2013/065121 filed Oct. 15, 2013 International Search Report and Written Opinion dated Jan. 16, 2014.
PCT/US2014/022019 filed Mar. 7, 2014 International Search Report and Written Opinion dated Jun. 11, 2014.
PCT/US2015/014795 filed Feb. 6, 2015 International Search Report and Written Opinion dated May 14, 2015.
PCT/US2016/039356 filed Jun. 24, 2016 International Search Report and Written Opinion dated Sep. 16, 2016.
PCT/US2017/066503 filed Dec. 14, 2017 International Search Report and Written Opinion dated Feb. 20, 2018.
PCT/US2019/055716 filed Oct. 10, 2019 International Search Report and Written Opinion dated Feb. 4, 2020.
PCT/US2020/066186 filed Dec. 18, 2020 International Search Report dated Mar. 23, 2021.
Pennington, C.R., Right Atrial Thrombus: a Complication of Total Parenteral Nutrition, British Medical Journal, pp. 446-447, vol. 295, Aug. 15, 1987.
Petersen, J et al, Silicone Venous Access Devices Positioned with their Tip High in the Superior Vena Cava are More Likely to Malfunction, Am J Surg, pp. 38-41, vol. 178 No. 1, Jul. 1999.
U.S. Appl. No. 12/878,915, filed Sep. 9, 2010 Final Office Action dated Sep. 26, 2012.
U.S. Appl. No. 12/878,915, filed Sep. 9, 2010 Non-Final Office Action dated Mar. 15, 2012.
U.S. Appl. No. 12/878,915, filed Sep. 9, 2010 Notice of Allowance dated Jan. 8, 2013.
U.S. Appl. No. 12/893,916, filed Sep. 29, 2010 Advisory Action dated Aug. 15, 2014.
U.S. Appl. No. 12/893,916, filed Sep. 29, 2010 Advisory Action dated Jun. 2, 2016.
U.S. Appl. No. 12/893,916, filed Sep. 29, 2010 Final Office Action dated Jan. 15, 2015.
U.S. Appl. No. 12/893,916, filed Sep. 29, 2010 Final Office Action dated Jun. 18, 2014.
U.S. Appl. No. 12/893,916, filed Sep. 29, 2010 Final Office Action dated Mar. 25, 2016.
U.S. Appl. No. 12/893,916, filed Sep. 29, 2010 Non-Final Office Action dated Aug. 31, 2016.
U.S. Appl. No. 12/893,916, filed Sep. 29, 2010 Non-Final Office Action dated Dec. 24, 2013.
U.S. Appl. No. 12/893,916, filed Sep. 29, 2010 Non-Final Office Action dated Sep. 10, 2015.
U.S. Appl. No. 12/893,916, filed Sep. 29, 2010 Non-Final Office Action dated Sep. 25, 2014.
U.S. Appl. No. 12/900,750, filed Oct. 8, 2010 Non-Final Office Action dated Jun. 3, 2013.
U.S. Appl. No. 13/019,939, filed Feb. 2, 2011 Final Office Action dated Apr. 2, 2014.
U.S. Appl. No. 13/019,939, filed Feb. 2, 2011 Non-Final Office Action dated Feb. 9, 2015.
U.S. Appl. No. 13/019,939, filed Feb. 2, 2011 Non-Final Office Action dated Oct. 11, 2013.
U.S. Appl. No. 13/118,033, filed May 27, 2011 Final Office Action dated Apr. 1, 2016.
U.S. Appl. No. 13/118,033, filed May 27, 2011 Non-Final Office Action dated Aug. 1, 2013.
U.S. Appl. No. 13/118,033, filed May 27, 2011 Non-Final Office Action dated Feb. 3, 2015.
U.S. Appl. No. 13/118,033, filed May 27, 2011 Non-Final Office Action dated Jul. 8, 2015.
U.S. Appl. No. 13/118,033, filed May 27, 2011 Non-Final Office Action dated May 22, 2014.
U.S. Appl. No. 13/118,033, filed May 27, 2011 Notice of Allowance dated Sep. 2, 2016.
U.S. Appl. No. 13/118,138, filed May 27, 2011 Final Office Action dated Apr. 1, 2016.
U.S. Appl. No. 13/118,138, filed May 27, 2011 Final Office Action dated Apr. 3, 2013.
U.S. Appl. No. 13/118,138, filed May 27, 2011 Non-Final Office Action dated Jul. 15, 2015.
U.S. Appl. No. 13/118,138, filed May 27, 2011 Non-Final Office Action dated Oct. 3, 2012.
U.S. Appl. No. 13/118,138, filed May 27, 2011 Non-Final Office Action dated Oct. 9, 2014.
U.S. Appl. No. 13/213,622, filed Aug. 19, 2011 Final Office Action dated Feb. 19, 2013.
U.S. Appl. No. 13/213,622, filed Aug. 19, 2011 Non-Final Office Action dated Jul. 31, 2012.
U.S. Appl. No. 13/213,622, filed Aug. 19, 2011 Non-Final Office Action dated May 22, 2014.
U.S. Appl. No. 13/240,171, filed Sep. 22, 2011 Advisory Action dated Aug. 18, 2015.
U.S. Appl. No. 13/240,171, filed Sep. 22, 2011 Advisory Action dated Jul. 22, 2016.
U.S. Appl. No. 13/240,171, filed Sep. 22, 2011 Final Office Action dated Jun. 10, 2015.
U.S. Appl. No. 13/240,171, filed Sep. 22, 2011 Final Office Action dated May 6, 2016.
U.S. Appl. No. 13/240,171, filed Sep. 22, 2011 Non-Final Office Action dated Dec. 1, 2015.
U.S. Appl. No. 13/240,171, filed Sep. 22, 2011 Non-Final Office Action dated Dec. 26, 2014.
U.S. Appl. No. 13/283,395, filed Oct. 27, 2011 Advisory Action dated Jan. 28, 2014.
U.S. Appl. No. 13/283,395, filed Oct. 27, 2011 Final Office Action dated Nov. 14, 2013.
U.S. Appl. No. 13/283,395, filed Oct. 27, 2011 Non-Final Office Action dated Apr. 23, 2013.
U.S. Appl. No. 13/336,919, filed Dec. 23, 2011 Advisory Action dated May 23, 2013.
U.S. Appl. No. 13/336,919, filed Dec. 23, 2011 Final Office Action dated Dec. 19, 2014.
U.S. Appl. No. 13/336,919, filed Dec. 23, 2011 Final Office Action dated Mar. 1, 2013.
U.S. Appl. No. 13/336,919, filed Dec. 23, 2011 Non-Final Office Action dated Dec. 27, 2013.
U.S. Appl. No. 13/336,919, filed Dec. 23, 2011 Non-Final Office Action dated Jul. 9, 2015.
U.S. Appl. No. 13/336,919, filed Dec. 23, 2011 Non-Final Office Action dated Oct. 16, 2012.

(56) References Cited

OTHER PUBLICATIONS

U.S. Appl. No. 13/336,919, filed Dec. 23, 2011 Notice of Allowance dated Jul. 26, 2016.
U.S. Appl. No. 13/337,987, filed Dec. 27, 2011 Examiner's Answer dated Jul. 2, 2014.
U.S. Appl. No. 13/337,987, filed Dec. 27, 2011 Final Office Action dated Sep. 19, 2013.
U.S. Appl. No. 13/337,987, filed Dec. 27, 2011 Non-Final Office Action dated Mar. 15, 2013.
U.S. Appl. No. 13/469,932, filed May 11, 2012 Advisory Action dated Jun. 27, 2016.
EP 211857735 filed Jul. 16, 2021 Extended European Search Report dated Nov. 5, 2021.
U.S. Appl. No. 16/394,861, filed Apr. 25, 2019 Notice of Allowance dated Apr. 11, 2022.
U.S. Appl. No. 16/830,040, filed Mar. 25, 2020 Non-Final Office Action dated May 5, 2022.
U.S. Appl. No. 17/127,587, filed Dec. 18, 2020 Non-Final Office Action dated May 11, 2022.
GB Application 0800474.9 filed Aug. 24, 2006 Office Action dated Mar. 17, 2010.
Gebauer, B et al, Ultrasound and Fluoroscopy-guided Implantation of Peripherally Inserted Central Venous Catheters (PICCs), ROFO, pp. 386-391, vol. 176 No 3, Mar. 2004 (Abstract only).
Gebhard, et al., "The accuracy of Electrocardiogram-Controlled Central Line Placement." The International Anesthesia Research Society, vol. 104, No. 1 Jan. 2007.
Gjendemsjo, Anders, et al., Energy and Power, The Connexions Project, Version 1.2, Feb. 20, 2004.
Gladwin, MT et al, Cannulation of the Internal Jugular Vein: is postpocedural chest radiography always necessary?, Crit Care Med, 33 pages, Oct. 2000.
Gonzales, et al. "Peripherally Inserted Central Catheter Placement in Swine Using Magnet Detection." Journal of Intravenous Nursing, vol. 22, No. 3, May/Jun. 1999.
Greenall, M.J. et al, Cardiac Tamponade and Central Venous Catheters, British Medical Journal, pp. 595-597, Jun. 14, 1975.
Guillory, "Basic Principles of Technologies for Catheter Localization." C.R. Bard internal paper, Oct. 20, 2004.
Guth, AA, Routine Chest X-rays after Insertion of Implantable Long-Term Venous Catheters: Necessary or Not?, Am Surg, pp. 26-29, vol. 67 No 1, Jan. 2001 (Abstract only).
Hamza, N. et al. "Interference reduction in ECG signal acquisition: Ground electrode removal." 2013 International Conference on Computer Medical Applications (ICCMA), Jan. 2013.
Hill, Bradley et al, Abstract of article discussing VasaNova VPS as guide for placement of PICCs. 2009.
Hill, Bradley, Identifying the Caval-Atrial Junction Using Smart-Catheter Technology presentation, 22nd Annual Scientific Meeting of the AVA in Savannah, Georgia, Sep. 13, 2008.
Hoffman, Thomas et al, Simultaneous Measurement of Pulmonary Venous Flow by Intravascular Catheter Doppler Velocimetry and Transesophageal Doppler Echocardiography: Relation to Left Atrial Pressure and Left Atrial and Left Ventricular Function, pp. 239-249, J Am Coll Cardiol, Jul. 1995.
Hoffmann, et al. "New Procedure in Transesophageal Echocardiography: Multiplane Transesophageal Echocardiography and Transesophageal Stress Echocardiography." Herz, vol. 18, No. 5, pp. 269-277, Oct. 1993.
Honeywell, "1, 2 and 3 Axis Magnetic Sensors HMC1051/HMC1052L/HMC1053" dated Jan. 2010.
Iacopino, Domenico Gerardo et al, Intraoperative Microvascular Doppler Monitoring of Blood Flow within a Spinal Dural Arteriovenous Fistula: A Precious Surgical Tool, vol. 10, 5 pages, Neurosurg. Focus, Feb. 2001.
Jeon, Yunseok et al., "Transesophageal Echocardiographic Evaluation of ECG-guided Central Venous Catheter Placement," Canadian Journal of Anesthesia, vol. 53, No. 10, Oct. 1, 2006, pp. 978-983.
Joosting, Jean-Pierre, "Dual-interface RFID-compatible EEPROM enables remote access to electronic device parameters," EE Times, Mar. 8, 2010.
JP 2008-528151 filed Aug. 24, 2006 Notice of Grant dated May 6, 2012.
JP 2010-504220 filed Sep. 3, 2009 Final Office Action dated Apr. 18, 2013.
JP 2010-504220 filed Sep. 3, 2009 Office Action dated Apr. 1, 2014.
JP 2010-504220 filed Sep. 3, 2009 Office Action dated Apr. 18, 2013.
JP 2010-504220 filed Sep. 3, 2009 Office Action dated May 21, 2012.
JP 2010-535117 filed May 26, 2011 First Office Action dated Aug. 5, 2013.
JP 2012-515222 filed Dec. 9, 2011 Office Action dated Feb. 23, 2015.
JP 2012-515222 filed Dec. 9, 2011 Office Action dated Mar. 24, 2014.
JP 2012-552060 filed Aug. 1, 2012 Office Action dated Nov. 12, 2014.
JP 2012-552060 filed Aug. 1, 2012 Second Office Action dated Nov. 6, 2015.
JP 2013-512046 filed Nov. 26, 2012 First Office Action dated Mar. 23, 2015.
JP 2013-512046 filed Nov. 26, 2012 Office Action dated Dec. 8, 2015.
JP 2013-512046 filed Nov. 26, 2012 Office Action dated May 16, 2016.
JP 2013-512051 filed Nov. 26, 2012 First Office Action dated Mar. 23, 2015.
JP 2013-524999 filed Jan. 22, 2013 First Office Action dated Jun. 1, 2015.
JP 2013-530322 filed Mar. 18, 2013, Office Action dated Jul. 6, 2018.
JP 2013-530322 filed Mar. 18, 2013, Office Action dated Mar. 2, 2017.
JP 2013-530322 filed Mar. 18, 2013, Office Action dated Nov. 6, 2017.
JP 2014-519081 filed Dec. 27, 2013 First Office Action dated Apr. 26, 2016.
JP 2015-534770 filed Mar. 26, 2015 Office Action dated Feb. 21, 2018.
JP 2015-534770 filed Mar. 26, 2015 Office Action dated Jun. 12, 2017.
JP2013-530322 filed Mar. 18, 2013, Office Action dated May 2, 2016.
JP2013-530322 filed Mar. 18, 2013, First Office Action dated Jul. 31, 2015.
Kim, Ko et al, Positioning Internal Jugular Venous Catheters using the Right Third Intercostal Space in Children, Acta Anaesthesiol Scand, pp. 1284-1286, vol. 47 No 10, Nov. 2003.
Kjelstrup T et al, Positioning of Central Venous Catheters using ECG, Tidssk Nor Laegeforen, pp. 599-601, vol. 111 No 5, Feb. 1999 (Abstract only).
Kofler, Julia, et al., Epinephrine application via an endotracheal airway and via the Combitube in esophageal position, Critical Care Medicine: May 2000, vol. 28: Issue 5, pp. 1445-1449.
Konings, MK, et al., Development of an intravascular impedance catheter for detection of fatty lesions in arteries, IEEE Trans Med Imaging Aug. 1997; 16(4):439-46.
Kowalski, CM et al, Migration of Central Venous Catheters: Implications for Initial Catheter Tip Positioning, J Vasc Interv Radiol, pp. 443-447, vol. 8 No. 3, May-Jun. 1997.
KR 10-2012-7000866 filed Jan. 11, 2012 First Office Action dated Jun. 16, 2016.
KR 10-2012-7000866 filed Jan. 11, 2012 Second Office Action dated Nov. 3, 2016.
KR 10-2013-7006933 filed Mar. 19, 2013 Office Action dated Aug. 7, 2017.
KR 10-2014-7002789 filed Feb. 3, 2014 Office Action dated Feb. 22, 2019.
PCT/US2022/026606 filed Apr. 27, 2022, International Search Report and Written Opinion dated Jul. 21, 2022.

(56) References Cited

OTHER PUBLICATIONS

U.S. Appl. No. 16/011,380, filed Jun. 18, 2018 Final Office Action dated Jul. 21, 2022.

U.S. Appl. No. 16/734,011, filed Jan. 3, 2020, Restriction Requirement dated Jul. 20, 2022.

U.S. Appl. No. 16/777,685, filed Jan. 30, 2020 Final Office Action dated Jul. 12, 2022.

U.S. Appl. No. 17/127,587, filed Dec. 18, 2020 Final Office Action dated Sep. 21, 2022.

PCT/US2021/052066 filed Sep. 24, 2021 International Search Report and Written Opinion dated Jan. 10, 2022.

U.S. Appl. No. 16/011,380, filed Jun. 18, 2018 Non-Final Office Action dated Dec. 24, 2021.

U.S. Appl. No. 16/394,861, filed Apr. 25, 2019 Final Office Action dated Jan. 31, 2022.

U.S. Appl. No. 16/777,685, filed Jan. 30, 2020 Non-Final Office Action dated Jan. 18, 2022.

"ASCENSION to Launch New 3D Guidance™ Tracker at TCT 2006." Press Releases from Ascension website: www.ascension-tech.com/news/press_101106.php, last accessed Dec. 1, 2006.

Acuson—The Value of Vision, AcuNav Diagnostic Ultrasound Catheter, 2000.

Advertising flyer for GAVECELT—The Italian Group for Long Term Venous Access Devices, for program on International Meeting on PICC's, Midline Catheters and Long Term Venous Access Devices in Catholic University, Rome, Italy on Dec. 3, 4, 5, 2008.

Alexander, GD et al, The Role of Nitrous Oxide in Postoperative Nausea and Vomiting, Collection of Abstracts Presented at the International Anesthesia Research Society by various speakers, 58th Congress, Mar. 12-14, 1984, Anesthesia and Analgesia, pp. 175-284, vol. 63, 1984.

Allan, P.L. et al, Role of Ultrsound in the Assessment of Chronic Venous Insufficiency, Ultrasound Quarterly, vol. 17, No. 1, pp. 3-10, 2001.

Andropoulos, et al. "A Controlled Study of the Transesophageal Echocardiography to Guide Central Venous Catheter Placement in Congetital Heart Surgery Patients." The International Anesthesia Research Society, vol. 89, pp. 65-70, 1999.

Anonymous author, Correct Catheter Placement with a low-impact, reliable and economical method, <http://www.cvc-partner.com/index.cfm?103A955CC6844BF58ACFE3C9C1471959>, last accessed Dec. 22, 2011.

Arai, J et al, Detection of Peripherally Inserted Central Catheter Occlusion by in-line Pressure Monitoring, Paediatr Anaesth, pp. 621-624, vol. 12 No 7, Sep. 2002.

Arrow International, Inc., The Arrow-Johans RAECG Adapter-Making Proper Central Venous Catheter Placement More Reliable (Modle No. EG-04900), Technical Report 1987, USA.

Aslamy, et al. "MRI of Central Venous Anatomy: Implications for Central Venous Catheter Insertion." American College of Chest Physicians, Jun. 8, 2009.

AU 2006283022 filed Aug. 24, 2006 Office Action dated Dec. 22, 2010.

AU 2008329807 exam requested Aug. 13, 2012 Examination Report No. 1 dated Feb. 15, 2013.

AU 2008329807 exam requested Aug. 13, 2012 Notice of Acceptance dated Feb. 14, 2014.

AU 2010300677 filed Mar. 12, 2012 First Examination Report dated Mar. 9, 2014.

AU 2011289513 filed Jan. 21, 2013 Examiner's Report dated Jul. 5, 2013.

AU 2012202293 filed Apr. 19, 2012 Examination Report No. 1 dated Apr. 24, 2013.

AU 2012278809 filed Nov. 12, 2013 Notice of Acceptance dated Sep. 13, 2016.

AU 2013201648 filed Mar. 19, 2013 Examiner's Report dated Mar. 5, 2014.

AU 2013201648 filed Mar. 19, 2013 Examiner's Report dated Oct. 14, 2013.

AU 2013202824 filed Apr. 6, 2013 First Examiner's Report dated Mar. 10, 2014.

AU 2013204243 filed Apr. 12, 2013 Examiner's Report dated Jun. 5, 2013.

AURORA® System Technical Specifications, Oct. 2003.

AZoMaterials. Nickel-Based Super Alloy Inconel 625—Properties and Applications by United Performance Alloys. Oct. 27, 2015. Last accessed Mar. 23, 2018. <URL:https://web.archive.org/web/20151027202821/https://www.azom.com/article.aspx?ArticleID=4461>.

B. Braun Website, "The Optimal Position of the Central Venous Catheter." http://www.cvcpartner.com/index.cfm18F1BDEA1310466194960A39F4E90968 (2009).

B. Braun, Certofix Central Venous Catheter for Placement Using the Seldinger Technique with Simultaneous ECG Lead Option, Feb. 2010.

Bailey, SH et al, Is Immediate Chest Radiograph Necessary after Central Venous Catheter Placement in a Surgical Intensive Care Unit?, Am J Surg, pp. 517-522, vol. 180 No 6, Dec. 2000.

Bankier, Alexander A., Azygos Arch Cannulation by Central Venous Catheters: Radiographic Detection of Malposition and Subsequent Complications, Journal of Thoracic Imaging 12:64-69 (1997).

Barber, JM et al, A Nurse led Peripherally Inserted Central Catheter Line Insertion Service is Effective with Radiological Support, Clin Radiol, pp. 352-354, vol. 57 No 5, May 2002.

Bard Access Systems, Sherlock Tip Location System, 5 pages, 2006.

Bard Access Systems, Site Rite Vascular Acess Ultrasound System, 4 pages, 2005.

Benchimol, Alberto at al, Right Atrium and Superior Vena Cava Flow Velocity in Man Measured with the Doppler-Catheter Flowmeter-Telemetry System, The Amer Journal of Medicine, pp. 303-309, vol. 48, Mar. 1970.

Benzadon, M. N. et al: "Comparison of the Amplitude of the P-Wave from Intracardiac Electrocardiogram Obtained by Means of a Central Venous Catheter Filled With Saline Solution to That Obtained via Esophageal Electrocardiogram", American Journal of Cardiology, Cahners Publishing Co., Newton, MA, US, vol. 98, No. 7, Oct. 1, 2006 (Oct. 1, 2006), pp. 978-981.

BioAdvance Lumen Vu, Greenhouse Fund Feb. 2004 Recipient, www.bioadvance.com <http://www.bioadvance.com>, 2005.

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.

Buehrle, Douglas, PICC Placement in Humans using Electromagnetic Detection, <http://www.corpakmedsystems.com/supplement_material/supplementpages/navigator/navarticle.html>, 2008.

C.R. Bard, CathTrack™ Catheter Location System at www.bardaccess.com <http://www.bardaccess.com>, last accessed Apr. 28, 2011.

C.R. Bard, Inc., Bard Electrophysiology Product Catalogue, Bard Catheters, pp. 74-75 (2002), USA.

CA 2,619,909 filed Aug. 24, 2006 Examiner's Report dated Oct. 26, 2012.

CA 2,721,715 filed Apr. 17, 2009 Examiner's Report dated Aug. 18, 2015.

CA 2,721,715 filed Apr. 17, 2009 Examiner's Report dated Oct. 25, 2016.

CA 2800810 filed Nov. 26, 2012 Office Action dated Mar. 13, 2018.

CA 2800810 filed Nov. 26, 2012 Office Action dated Mar. 30, 2017.

CA 2800813 filed Nov. 26, 2012 Office Action dated Mar. 5, 2018.

Cadman, A et al, To Clot or Not to Clot? That is the question in Central Venous Catheters, Clinical Radiology, pp. 349-355, vol. 59 No 4, Apr. 2004.

Calvert, N et al, The Effectiveness and Cost-effectiveness of Ultrasound Locating Devices for Central Venous Access: A Systematic Review and Economic Evaluation, Health Technology Assessment, vol. 7, No. 12, 2003.

Cardella, John F. et al., Interventinal Radiologic Placement of Peripherally Inserted Central Catheters, Journal of Vascular and Interventional Radiology 1993; 4:653-660.

(56) References Cited

OTHER PUBLICATIONS

Carlon, R et al, Secondary Migration of a Central Venous Catheter—A Case Report, Minerva Anestesiol, pp. 927-931, vol. 69 No 12, Dec. 2003.
Caruso, LJ et al, A Better Landmark for Positioning a Central Venous Catheter, J Clinical Monitoring and Computing, pp. 331-334, vol. 17 No 6, Aug. 2002.
Cavatorta, et al., "Central Venous Catheter Placement in Hemodialysis: Evaluation of Electrocardiogramaing a Guidewire." The Journal of Vascular Access, vol. 2, pp. 45-50, 2001.
Chalkiadis, GA et al, Depth of Central Venous Catheter Insertion in Adults: An Audit and Assessment of a Technique to Improve Tip Position, Anaesth Intensive Care, pp. 61-66, vol. 26 No 1, Feb. 1998.
CN 201180052587.5 filed Apr. 28, 2013 Office Action dated Feb. 24, 2016.
CN 201180052587.5 filed Apr. 28, 2013 Second Office Action dated Aug. 19, 2015.
CN 201180068309.9 filed Aug. 22, 2013 First Office Action dated Oct. 16, 2014.
CN 201180068309.9 filed Aug. 22, 2013 Second Office Action dated May 6, 2015.
CN 201180068309.9 filed Aug. 22, 2013 Third Office Action dated Sep. 2, 2015.
CN 201280033189.3 filed Jan. 3, 2014 First Office Action dated Apr. 3, 2014.
CN 201280033189.3 filed Jan. 3, 2014 Second Office Action dated Sep. 14, 2015.
CN 201380051172.5 filed Mar. 30, 2015 Office Action dated Jan. 16, 2018.
CN 201380051172.5 filed Mar. 30, 2015 Office Action dated Jul. 30, 2018.
CN 201380051172.5 filed Mar. 30, 2015 Office Action dated May 2, 2017.
CN 201380065663.5 filed Jun. 15, 2015 Office Action dated Mar. 15, 2017.
CN 201380065663.5 filed Jun. 15, 2015 Office Action dated Oct. 10, 2017.
CN 201410009216.4 filed Jan. 8, 2014 Office Action dated Jun. 15, 2016.
CN 201410009216.4 filed Jan. 8, 2014 Second Office Action dated Sep. 25, 2015.
CN 201480010988.8 filed Aug. 27, 2015 Office Action dated Aug. 17, 2018.
CN 201480010988.8 filed Aug. 27, 2015 Office Action dated Dec. 13, 2017.
CN 201510144728.6 filed Apr. 17, 2015 Office Action dated Aug. 29, 2017.
CN 201510144728.6 filed Apr. 17, 2015 Office Action dated Jan. 23, 2017.
CN 201580007645.0 filed Aug. 8, 2016 Office Action dated Sep. 12, 2018.
CN 201610127217.8 filed Mar. 7, 2016 Office Action dated Dec. 28, 2017.
CN 201610127217.8 filed Mar. 7, 2016 Office Action dated Jun. 11, 2018.
CN 201610127217.8 filed Mar. 7, 2016 Office Action dated Nov. 19, 2018.
CN 201610166569.4 filed Dec. 23, 2010, Office Action dated Nov. 1, 2017.
CO 15110530 filed May 14, 2015 Office Action dated May 8, 2017.
CO 15110530 filed May 14, 2015 Office Action dated Nov. 25, 2016.
Colley, Peter S et al, ECG-Guided Placement of Sorenson CVP Catheters via Arm Veins, Anesthesia and Analgesia, pp. 953-956, vol. 63, 1984.
Collier, PE et al, Cardiac Tamponade from Central Venous Catheters, Am J Surg, pp. 212-214, vol. 176 No 2, Aug. 1998.
ComboWire® Pressure/Flow Guide Wire Ref 9500 Series, Instructions for Use, Apr. 2011.
Corsten, et al., "Central Placement Catheter Placement Using the ECG-Guided Cavafix-Certodyn SD Catheter." Journal of Clinical Anesthesiology, vol. 6, Nov./Dec. 1994.
Cucchiara, Roy et al, Time Required and Success Rate of Percantaneous Right Atrial Catherization: Description of a Technique, Canad. Anaesth. Soc. J., pp. 572-573, vol. 27, No. 6, Nov. 1980.
Cullinane, DC et al, The Futility of Chest Roentgenograms Following Routine Central Venous Line Changes, Am J Surg, pp. 283-285, vol. 176 No 3, Sep. 1998.
Curet, Myriam J. et al., University and Practice-based Physicians' Input on the Content of a Surgical Curriculum, The American Journal of Surgery® vol. 178 Jul. 1999, 78-84.
David, et al., "Is ECG-Guidance a Helpful Method to Correctly Position a Central Venous Catheter During Prehospital Emergency Care?" ACTA Anaesthesiologica Scandinavica, vol. 49, pp. 1010-1014, 2005.
DELTEC Cath-Finder® Tracking System Operation Manual, 1994.
Egelhof, Petra, Effects of Somatostatin on Portal Blood Flow and Portal Vein Pressure in Patients with Portal Hypertension due to Liver Cirrhosis Invasive Monitoring during TIPSS Procedures, Dissertation submitted to: Technical University of Munich, Faculty of Medicine, May 13, 2002; Date of examination: Feb. 26, 2003.
Engelhardt, W et al, ECG-Controlled Placement of Central Venous Catheters in Patients with Atrial Fibrallation, Anaesthesist, pp. 476-479, vol. 38 No. 9, Sep. 1989 (Abstract only).
Enrique Company-Bosch, "ECG Front-End Design is Simplified with MicroConverter." Analog Dialogue 37-11, (dated Nov. 2003).
EP 08855396.1 filed Jun. 15, 2010 European Search Report dated Jul. 31, 2012.
EP 08855396.1 filed Jun. 15, 2010 Intent to Grant dated Jul. 5, 2013.
EP 09707467.8 supplemental European search report dated Jun. 18, 2013.
EP 09743249.6 filed Oct. 18, 2010 Extended European Search Report dated Jan. 13, 2016.
EP 09743249.6 filed Oct. 18, 2010 Intention to Grant dated Mar. 2, 2017.
EP 09808901.4 filed Aug. 21, 2009 European Search Report dated May 23, 2012.
EP 09808901.4 filed Aug. 21, 2009 Examination Report dated May 10, 2013.
EP 09813632.8 filed Apr. 5, 2011 European Search Report dated Jul. 4, 2012.
EP 09813632.8 filed Apr. 5, 2011 Office Action dated Apr. 30, 2013.
EP 09813632.8 filed Apr. 5, 2011 Summons to Attend Oral Proceedings dated Apr. 16, 2014.
EP 10 808 660.4 filed Feb. 15, 2012 Extended European Search Report dated Mar. 4, 2014.
EP 10786978.6 filed Dec. 19, 2011 Extended European Search Report dated Mar. 7, 2014.
EP 10786978.6 filed Dec. 19, 2011 Office Action dated Aug. 11, 2017.
Pittiruti, et al, "The intracavitary ECG method for positioning the tip of central venous catheters: results of an Italian multicenter study," J Vasc Access, pp. 1-9, Nov. 21, 2011.
Pittiruti, et al, Intracavitary EKG Monitoring: A reliable method for controlling tip position during and after PICC Insertion presentation in Catholic University, Rome, Italy in 2008.
Pittiruti, et al. "The EKG Method for Positioning the Tip of PICCs: Results from Two Preliminary Studies." JAVA, vol. 13, No. 4, pp. 179-185, 2008.
Pittiruti, et al. "The electrocardiogramethod for positioning the tip of central venous catheters" JAVA, pp. 1-12, Feb. 12, 2011.
Polos, PG et al, Tips for Monitoring the Position of a Central Venous Catheter—How Placement can go awry—even when the anatomy is normal, J Crit Illn, pp. 660-674, vol. 8 No 6, Jun. 1993 (Abstract only).
Pop, Gheorghe A. et al., Catheter-based impedance measurements in the right atrium for continuously monitoring hematocrit and estimating blood viscosity changes; an in vivo feasibility study in swine, Biosensors and Bioelectronics 19 (2004) 1685-1693.
Popp, M. B. et al., Accuracy of implanted port placement with the use of the electromagnetic CathTrack® catheter locator system, The Journal of Vascular Access 2005; 6: 9-12.

(56) References Cited

OTHER PUBLICATIONS

Randolph AG et al, Ultrasound guidance for placement of central venous catheters: a meta-analysis of the literature! Critcal Care Medicine, pp. 2053-2058, vol. 24, Dec. 1996.
Reece, A et al, Posititioning Long Lines: Contrast Versus Plain Radiography, Arch Dis Child Fetal Neonatal Ed, pp. 129-130, vol. 84 No. 2, Mar. 2001.
Reynolds, N et al, Assessment of Distal Tip Position of Long Term Central Venous Feeding Catheters using Transesophageal Echocardiology, Jpen J Parenter Enteral Nutr, pp. 39-41, vol. 25 No. 1, Jan.-Feb. 2001.
RU 2011150917 filed Dec. 15, 2011 First Office Action dated Apr. 24, 2014.
RU 2011150917 filed Dec. 15, 2011 Second Office Action dated Aug. 28, 2014.
RU 2013158008 filed Dec. 26, 2013 First Office Action dated May 27, 2016.
RU 2015110633 filed Mar. 26, 2015 Office Action dated Oct. 25, 2018.
RU 2015111669 filed Apr. 1, 2015 Office Action dated Jan. 25, 2018.
RU 2015111669 filed Apr. 1, 2015 Office Action dated May 18, 2018.
RU 2015111669 filed Apr. 1, 2015 Office Action dated Sep. 5, 2017.
Ruschulte, Heiner et al, Prevention of Central Venous Catheter related infections with chlorhex idine gluconate Impregnated wound dressings: A randomized controlled trial, presented as an abstract at the Annual meeting of the European Society of Anesthesiologists (ESA) in Madrid, Spain in Jun. 2006, 12 pages, Annals of Hematology, Jul. 14, 2008.
Rutherford, J. S. et al., Depth of Central Venous Catheterization: An Audit of Practice in a Cardiac Surgical Unit, Anaesth Intens Care 1994; 22: 267-271.
Sacolick, et al. "Electromagnetically Tracked Placement of a Peripherally Inserted Central Catheter." SPIE Medical Imaging, 2004 Proceedings.
Salem, et al. "A New Peripherally Implanted Subcutaneous Permanent Central Venous Access Device for Patients Requiring Chemotherapy." Journal of Clinical Oncology, vol. 11, No. 11, pp. 2181-2185, Nov. 1993.
Savary, D et al, Intra-atrial Monitoring to Add Insertion of a Central Venous Line in Pre-Hospital Emergency Care Journal Europeen des Urgences, pp. 75-78, vol. 17 No. 2, 2004.
Schafer et al. "Incorrect placement of a vena cava catheter and its prevention by intra-atrial ECG." Anaesthesist. Jan. 1988;37(1):49-51.
Schummer, et al. "Central Venous Catheters—The inability of 'intra-atrial ECG' to prove adequate positioning." British Journal of Anaesthesia, vol. 93, No. 2, pp. 193-198, 2004.
Schummer, W et al, ECG-guided Central Venous Catheter Positioning: Does it detect the Pericardial Reflection rather than the Right Atrium?, Eur J Anaesthesiol, pp. 600-605, vol. 21 No. 8, Aug. 2004 (Abstract only).
Schummer, W et al, Intra-Atrial ECG is not a Reliable Method for Positioning Left Internal Jugular Vein Catheters, Br J Anaesth, pp. 481-486, vol. 91 No. 4, Oct. 2003.
Schummer, W, Central Venous Catheter—the Inability of "Intra-Atrial ECG" to prove Adequate Positioning, Br J Anaesth, pp. 193-198, vol. 93 No. 2, Aug. 2004.
Schuster, M. et al., The carina as a landmark in central venous catheter placement, British Journal of Anaesthesia 85 (2): 192-4 (2000).
Siela, Debra, Using Chest Radiography in the Intensive Care Unit, Crit Care Nurse Aug. 1, 2002 vol. 22 No. 4, pp. 18-27.
Simon, et al., "Central Venous Catheter Placement in Children: Evaluation of Electrocardiogramaing J-Wire." Paediatric Anaesthesia vol. 9, pp. 501-504, 1999.
Smith, Brigham, et al., Intravenous electrocardiogramce for placement of peripherally inserted central catheters, Journal of Electrocardiology 43 (2010) 274-278.
Stark, DD et al, Radiographic Assessment of Venous Catheter Position in Children: Value of the Lateral View, Pediatric Radiology, pp. 76-80, vol. 14 No. 2, 1984.
Starkhammar et al. "Cath-Finder Catheter Tracking System: A New Device for Positioning of Central Venous Catheters. Early Experience from Implantation of Brachial portal Systems." Acta Anaesthesiol Scandinavia, vol. 34, No. 4 pp. 296-300, May 1990.
Starkhammer, H et al, Central Venous Catheter Placement using Electromagnetic Position Sensing: A Clinical Evaluation, Biomed. Instrum Technol, vol. 30 No 2, pp. 164-170; Mar.-Apr. 1996.
Starr, David S et al, EKG Guided Placement of Subclavian CVP Catheters Using J-Wire, pp. 673-676, Ann. Surg, Dec. 1986.
Stas, M et al, Peroperative Intravasal Electrographic Control of Catheter Tip Position in Access Ports Placed by Venous Cut-Down Technique, EJSO, pp. 316-320, vol. 27, 2001.
STEREOTAXIS Magetic Navigation System with Navigant™ User Interface, 2005 Brochure.
STEREOTAXIS, Expanding the Possibilites of Interventional Medicine: Remote Navigation and Automation, pp. 1-8, Apr. 2011.
Tepa® Health Innovation PC based ECG System Introduction and Technical Specifications, EKG Master USB, 2 pages, Nov. 2003.
Thakor, N. V., et al. "Ground-Free ECG Recording with Two Electrodes." IEEE Transactions on Biomedical Engineering, vol. BME-27, No. 12, Dec. 1980.
The FloWire Doppler Guide Wire located <http://www.volcanocorp.com/products/flowire-doppler-guide-wire.php>, 2011.
TRAXAL Technologies, Tracking Technology website overview: www.traxal.com/rd/rd_classroom_trackingtechnology.htm, last accessed Dec. 1, 2006.
UAB Health Systems, Arrhythmias, retrieved from http://www.health,uab.edu/14564/ on Nov. 15, 2007, 12 pages.
U.S. Appl. No. 11/466,602, filed Aug. 23, 2006 Advisory Action dated Jun. 22, 2009.
U.S. Appl. No. 11/466,602, filed Aug. 23, 2006 Appeal Board Decision dated Sep. 17, 2012.
U.S. Appl. No. 11/466,602, filed Aug. 23, 2006 Final Office Action dated Apr. 8, 2010.
U.S. Appl. No. 11/466,602, filed Aug. 23, 2006 Final Office Action dated Jan. 30, 2009.
U.S. Appl. No. 11/466,602, filed Aug. 23, 2006 Final Office Action dated Oct. 28, 2013.
U.S. Appl. No. 11/466,602, filed Aug. 23, 2006 Non-Final Office Action dated Mar. 28, 2013.
U.S. Appl. No. 11/466,602, filed Aug. 23, 2006 Non-Final Office Action dated Sep. 25, 2009.
Chamsi-Pasha, Hassan et al, Cardiac Complications of Total Parenteral Nutrition: The Role of Two-Dimensional Echocardiography in Diagnosis, Annals of the Royal College of Surgeons of England, pp. 120-123, vol. 71, 1989.
Chang, Thomas C. et al., Are Routine Ch Ladiographs Necessary After Image-Guided Placement of Internal Jugular Central Venous Access Devices?, AJR Feb. 1998;170:335-337.
Chaturvedi et al., "Catheter Malplacement During Central Venous Cannulation Through Arm Veins in Pediatric Patients." Journal of Neurosurgical Anesthesiology, vol. 15, No. 3 pp. 170-175, Jan. 2003.
Chen, Zhongping et al, Optical Doppler Tomography: Imaging in vivo Blood Flow Dynamics Following Pharmacological Intervention and Photodynamic Therapy, 7 pages, vol. 67, Photochemistry and Photobiology, 1998.
Cheng, Ki et al, A Novel Approach of Intravenous Electrocardiogramique in Correct Position the Long-Term Central Venous Catheter, Kaohsiung J Med Sci, pp. 241-247, vol. 16 No 5, May 2000 (Abstract only).
Cheung, P., et al., The Effect of a Disposable Probe Cover on Pulse Oximetry, Anaesth Intensive Care 2002; 30: 211-214.
Chu, et al., "Accurate Central Venous Port-A Catheter Placement: Intravenous Electrocardiogramand Surface Landmark Techniques Compared by Using Transesophageal Echocardiography." The International Anesthesia Research Society, vol. 98, pp. 910-914, 2004.
Claasz, Antonia et al, A Study of the Relationship of the Superior Vena Cava to the Bony Landmarks of the Sternum in the Supine Adult: Implications for Magnetic Guidance Systems, Journal, vol. 12 No.3, JAVA, Jul. 24, 2007.

(56) References Cited

OTHER PUBLICATIONS

Clifford, et al. "Assessment of Hepatic Motion Secondary to Respiration for Computer Assisted Interventions." Computer Aided Surgery, vol. 7, pp. 291-299, 2002.
CN 200880012117.4 filed Apr. 16, 2008 First Office Action dated Dec. 23, 2011.
CN 200880012117.4 filed Apr. 16, 2008 Fourth Office Action dated Sep. 4, 2013.
CN 200880012117.4 filed Apr. 16, 2008 Second Office Action dated Oct. 8, 2012.
CN 200880012117.4 filed Apr. 16, 2008 Third Office Action dated Apr. 27, 2013.
CN 200880125528.4 filed Nov. 25, 2008 First Office Action dated Jun. 5, 2012.
CN 200880125528.4 filed Nov. 25, 2008 Second Office Action dated Mar. 6, 2013.
CN 200880125528.4 filed Nov. 25, 2008 Third Office Action dated Jul. 1, 2013.
CN 200980123021 X filed Dec. 17, 2010 First Office Action dated Nov. 19, 2012.
CN 200980123021.X filed Dec. 17, 2010 Second Office Action dated Aug. 13, 2013.
CN 200980123021.X filed Dec. 17, 2010 Third Office Action dated Apr. 22, 2014.
CN 200980144663.8 filed May 9, 2011 Decision of Re-Examination dated Feb. 21, 2017.
CN 200980144663.8 filed May 9, 2011 Fifth Office Action dated May 26, 2015.
CN 200980144663.8 filed May 9, 2011 First Office Action dated Dec. 5, 2012.
CN 200980144663.8 filed May 9, 2011 Fourth Office Action dated Nov. 15, 2014.
CN 200980144663.8 filed May 9, 2011 Notice of Reexamination dated Aug. 5, 2016.
CN 200980144663.8 filed May 9, 2011 Second Office Action dated Aug. 22, 2013.
CN 200980144663.8 filed May 9, 2011 Third Office Action dated May 4, 2014.
CN 201080035659.0 filed Feb. 10, 2012 First Office Action dated Jan. 26, 2014.
CN 201080035659.0 filed Feb. 10, 2012 Second Office Action dated Oct. 9, 2014.
CN 201080035659.0 filed Feb. 10, 2012 Third Office Action dated Mar. 19, 2015.
CN 201080053838.7 filed May 28, 2012 First Office Action dated Jan. 6, 2014.
CN 201080053838.7 filed May 28, 2012 Fourth Office Action dated Jun. 2, 2015.
CN 201080053838.7 filed May 28, 2012 Second Office Action dated Jun. 17, 2014.
CN 201080053838.7 filed May 28, 2012 Third Office Action dated Dec. 4, 2014.
CN 201180016462.7 filed Sep. 27, 2012 First Office Action dated Mar. 21, 2014.
CN 201180016462.7 filed Sep. 27, 2012 Second Office Action dated Dec. 9, 2014.
CN 201180016462.7 filed Sep. 27, 2012 Third Office Action dated Jun. 10, 2015.
CN 201180037065.8 filed Jan. 28, 2013 First Office Action dated Sep. 28, 2014.
CN 201180037065.8 filed Jan. 28, 2013 Fourth Office Action dated May 5, 2016.
CN 201180037065.8 filed Jan. 28, 2013 Notice of Grant dated Aug. 30, 2016.
CN 201180037065.8 filed Jan. 28, 2013 Second Office Action dated Jun. 2, 2015.
CN 201180037065.8 filed Jan. 28, 2013 Third Office Action dated Nov. 24, 2015.
CN 201180037068.1 filed Jan. 28, 2013 First Office Action dated Apr. 20, 2015.
CN 201180037068.1 filed Jan. 28, 2013 First Office Action dated Sep. 9, 2014.
CN 201180037068.1 filed Jan. 28, 2013 Third Office Action dated Oct. 19, 2015.
CN 201180040151.4 filed Feb. 19, 2013 First Office Action dated Oct. 28, 2014.
CN 201180040151.4 filed Feb. 19, 2013 Office Action dated Dec. 10, 2015.
CN 201180040151.4 filed Feb. 19, 2013 Second Office Action dated Jun. 19, 2015.
CN 201180043512.0 filed Mar. 8, 2013 First Office Action dated Jul. 31, 2014.
CN 201180043512.0 filed Mar. 8, 2013 Second Office Action dated Apr. 14, 2015.
CN 201180052587.5 filed Apr. 28, 2013 First Office Action dated Jan. 26, 2015.
KR 10-2014-7002789 filed Feb. 3, 2014 Office Action dated Jun. 21, 2018.
Leowenthal, MR et al, The Peripherally Inserted Central Catheter (PICC): A Prospective Study of its Natural History after Fossa Insertion, Anaesth Intensive Care, pp. 21-24; vol. 30 No 1, Feb. 2002.
Lepage Ronan et al. ECG Segmentation and P-wave Feature Extraction: Application to Patients Prone to Atrial Fibrillation, IEEE/EMBS Proceedings, 23rd Annual Conference, Istanbul, Turkey, Oct. 25-28, 2001.
Liu , Ji-Bin et al, Catheter-Based Intralumincal Sonography, J Ultrasound Med, pp. 145-160, vol. 23, 2004.
Lucey, B et al, Routine Chest Radiographs after Central Line Insertion: Mandatory Postprocedural Evaluation or Unnecessary Waste of Resources?, Cardiovasc Intervent Radiol, pp. 381-384, vol. 22 No 5, Sep.-Oct. 1999.
Lum, Phillip, A New Formula-Based Measurement Guide for Optimal Positioning of Central Venous Catheters, JAVA, vol. 9, No. 2, pp. 80-85, 2004.
Lynch, RE et al, A Procedure for Placing Pediatric Femoral Venous Catheter Tips near the Right Atrium, Pediatr Emerg Care, pp. 130-132, vol. 18 No 2, Apr. 2002.
Madan, et al. "Right Atrial Electrocardiograma Technique for the Placement of Central Venous Catheters for Chemotherapy or Intravenous Nutrition." British Journal of Surgery, vol. B1, pp. 1604-1605, 1994.
Madias, John E, Intracardiac (Superior Vena Cava/Right Atrial) ECGs using Saline Solution as the Conductive Medium for the Proper Positioning of the Shiley Hemodialysis Catheter: Is it Not Time to Forego the Postinsertion Chest Radiograph?, pp. 2363-2367, CHEST, 2003.
Markovich, Mary B., Central Venous Catheter Tip Placement: Determination of Posterior Malposition—A Case Study, JAVA, vol. 11, No. 2, pp. 85-89, 2006.
Martin, Roy W, An Ultrasoundic Catheter for Intravascular Measurement of Blood Flow: Technical Details, IEEE Transactions on Sonics and Ultrasonics, vol. SU-27, No. 6, pp. 277-286, Nov. 1980.
Mcdonnall, "Intra-Atrial Electrocardiogram Catheter Placement." Literature review prepared for Bard Access Systems, Oct. 2007.
Mcgee et al., "Accurate Placement of Central Venous Catheters: A Prospective, Randomize, Multicenter Trail." Critical Care Medicine, vol. 21 No. 8, Aug. 1993.
MedGraphics, CardioPerfect® Resting/Stress ECG System, 3 pages, 2001.
Michenfelder, John et al, Air Embolism During Neurosurgery—An Evaluation of Right-Atrial Catheters for Diagnosis and Treatment, JAMA, pp. 1353-1358, vol. 208, No. 8, May 26, 1969.
Michenfelder, John et al, Air Embolism During Neurosurgery. A New Method of Treatment, Anesthesia and Analgesia. Current Researches, pp. 390-395, vol. 45, No. 4, Jul.-Aug. 1966.
MICROBIRD™ Miniaturized DC Magnetic Sensors for Intra-body Navigation and Localization, Specifications, 2005.
Micronix CathRite™ Cardiac Access Device Brochure. Jun. 2004.
Micronix Pty Ltd "CathRite" Guiding Styled Core Manufacturing, Jun. 15, 2006.
Moureau, Nancy L. et al., "Electrocardiogram (EKG) Guided Peripherally Inserted Central Catheter Placement and Tip Position:

(56) References Cited

OTHER PUBLICATIONS

Results of a Trial to Replace Radiological Confirmation," Journal of the Association for Vascular Access, op. 8-14, vol. 15, No. 1, 2010.
Murthy, Vrudhula et al, Analysis of Power Spectral Densities of Electrocardiograms, Mathematical Biosciences, pp. 41-51, vol. 12 No 1-2, Oct. 1971.
MX/a/2012/013672 filed Nov. 23, 2012 First Office Action dated Aug. 10, 2015.
MX/a/2012/013858 filed Nov. 28, 2012 First Office Action dated Sep. 26, 2014.
MX/a/2012/013858 filed Nov. 28, 2012 Second Office Action dated Jun. 10, 2015.
MX/a/2013/001317 filed Jan. 31, 2013 First Office Action dated Nov. 26, 2015.
MX/a/2015/004864 filed Apr. 16, 2015 Office Action dated Apr. 24, 2018.
MX/a/2015/004864 filed Apr. 16, 2015 Office Action dated Dec. 18, 2017.
Nadroo, AM et al, Changes in Upper Extremity Position Cause Migration of Peripherally Inserted Central Catheters in Neonates, Pediatrics, pp. 131-136, vol. 110, Jul. 2002.
Nakatani, K et al, Accurate Placement of Central Venous Catheters—ECG-guided method vs Patient Height Method, Masui, pp. 34-38, vol. 51 No 1, Jan. 2002.
Nazarian, GK et al, Changes in Tunneled Catheter Tip Position when a patient is Upright, J Vasc Interv Radiol, pp. 437-441, vol. 8 No 3, May-Jun. 1997.
NEUROMETER® CPT, Clinical Applications. Neurotron , Inc. website: www.neurotron.com/CLINAPS.html, last accessed Oct. 23, 2006.
NEUROMETER® CPT, Frequently Asked Questions. Neurotron , Inc. website: www.neurotron.com/CPTFAQ/html, last accessed Oct. 23, 2006.
NEUROMETER® CPT, Products Page. Neurotron , Inc. website: www.neurotron.com/products.html, last accessed Oct. 23, 2006.
NEUROMETER® Electrodiagnostic Neuroselective Sensory Nerve Evaluation: Charts, Tables, Documents & Downloads. Neurotron , Inc. website: www.neurotron.com/downloads.html, last accessed Oct. 23, 2006.
NOT Resource Center. Magnetic Permeability. Oct. 18, 2014. Last accessed Mar. 23, 2018. <URL:https://web.archive.org/web/20141018213902/https://www.nde-ed.org/EducationResources/CommunityCollege/Materials/Physical_Chemical/Permeability.htm>.
Odd, De et al, Does Radio-opaque Contrast Improve Radiographic localisation of Percutaneous Central Venous Lines?, Arch Dis Child Fetal Neonatal Ed, pp. 41-43, vol. 89 No 1, Jan. 2004.
Palesty, JA et al, Routine Chest Radiographs Following Central Venous Recatherization over a Wire are not Justified, Am J Surg, pp. 618-621, vol. 176 No 6, Dec. 1998.
Paliotti, Roberta P. et al, Intravascular Doppler Technique for Monitoring Renal Venous Blood Flow in Man, J Nephrol, pp. 57-62, 2003.
Parker, K.H. et al, Cardiovascular Fluid Dynamics, Department of Bioengineering, National Heart and Lung Institute, Imperial College of Science, Technology and Medicine, Cardiovascular Haemodynamics, pp. 1-28, Sep. 26, 2005.
Pawlik, et al., "Central Venous Catheter Placement: Comparison of the Intravascular Guidewire and the Fluid Column Electrocardiograms." European Journal of Anesthesiology, vol. 41, pp. 594-599, 2004.
PCT/US13/62409 filed Sep. 27, 2013 International Search Report and Written Opinion dated Feb. 24, 2014.
PCT/US2006/033079 filed Aug. 24, 2006 International Preliminary Report on Patentability dated Feb. 26, 2008.
PCT/US2006/033079 filed Aug. 24, 2006 Search Report dated Dec. 19, 2006.
PCT/US2006/033079 filed Aug. 24, 2006 Written Opinion dated Dec. 19, 2006.
PCT/US2008/060502 filed Apr. 16, 2008 International Search Report and Written Opinion dated Oct. 16, 2008.
PCT/US2008/084751 filed Nov. 25, 2008 International Preliminary Report on Patentability dated Jun. 1, 2010.
PCT/US2008/084751 filed Nov. 25, 2008 Search Report dated May 20, 2009.
PCT/US2008/084751 filed Nov. 25, 2008 Written Opinion dated May 20, 2009.
PCT/US2009/033116 filed Feb. 4, 2009 International Preliminary Report on Patentability dated Aug. 10, 2010.
PCT/US2009/033116 filed Feb. 4, 2009 Search Report dated Mar. 13, 2009.
PCT/US2020/015947 filed Jan. 30, 2020 International Search Report and Written Opinion dated Jun. 11, 2020.
U.S. Appl. No. 16/011,380, filed Jun. 18, 2018 Notice of Allowance dated Apr. 3, 2023.
U.S. Appl. No. 16/653,594, filed Oct. s15, 2019 Non-Final Office Action dated Feb. 1, 2023.
U.S. Appl. No. 16/734,011, filed Jan. 3, 2020, Non-Final Office Action dated Oct. 28, 2022.
U.S. Appl. No. 16/777,685, filed Jan. 30, 2020 Examiner's Answer dated Apr. 11, 2023.
U.S. Appl. No. 16/830,040, filed Mar. 25, 2020 Notice of Allowance dated Sep. 29, 2022.
U.S. Appl. No. 17/105,221, filed Nov. 25, 2020 Non-Final Office Action dated Oct. 6, 2022.
U.S. Appl. No. 17/127,587, filed Dec. 18, 2020 Non-Final Office Action dated Apr. 7, 2023.
U.S. Appl. No. 17/240,894, filed Apr. 26, 2021 Notice of Allowance dated Dec. 13, 2022.
U.S. Appl. No. 17/317,591, filed May 11, 2021, Restriction Requirement dated Feb. 24, 2023.
U.S. Appl. No. 16/011,380, filed Jun. 18, 2018 Notice of Allowance dated May 17, 2023.
U.S. Appl. No. 16/734,011, filed Jan. 3, 2020, Advisory Action dated Aug. 10, 2023.
U.S. Appl. No. 16/734,011, filed Jan. 3, 2020, Final Office Action dated May 18, 2023.
U.S. Appl. No. 17/105,221, filed Nov. 25, 2020 Notice of Allowance dated Jun. 2, 2023.
U.S. Appl. No. 17/317,591, filed May 11, 2021 Non-Final Office Action dated Jun. 20, 2023.
U.S. Appl. No. 16/653,594, filed Oct. 15, 2019 Final Office Action dated Dec. 13, 2023.
U.S. Appl. No. 17/317,591, filed May 11, 2021 Final Office Action dated Nov. 28, 2023.
U.S. Appl. No. 16/653,594, filed Oct. 15, 2019 Non-Final Office Action dated Aug. 16, 2023.
U.S. Appl. No. 17/127,587, filed Dec. 18, 2020 Final Office Action dated Aug. 31, 2023.
U.S. Appl. No. 16/206,890, filed Nov. 30, 2018 Restriction Requirement dated Jan. 14, 2025.
U.S. Appl. No. 16/734,011, filed Jan. 3, 2020 Notice of Allowance dated Jan. 16, 2025.
U.S. Appl. No. 16/777,685, filed Jan. 30, 2020 Non-Final Office Action dated Mar. 3, 2025.
U.S. Appl. No. 17/389,191, filed Jul. 29, 2021 Restriction Requirement dated Feb. 6, 2025.
U.S. Appl. No. 17/471,034, filed Sep. 9, 2021 Restriction Requirement dated Feb. 6, 2025.
U.S. Appl. No. 17/127,587, filed Dec. 18, 2020 Non-Final Office Action dated Nov. 5, 2025.
U.S. Appl. No. 17/731,169, filed Apr. 27, 2022 Advisory Action dated Jan. 30, 2026.
U.S. Appl. No. 17/731,169, filed Apr. 27, 2022 Final Office Action dated Nov. 21, 2025.
U.S. Appl. No. 16/206,890, filed Nov. 30, 2018 Non-Final Office Action dated May 20, 2025.
U.S. Appl. No. 17/389,191, filed Jul. 29, 2021 Non-Final Office Action dated May 22, 2025.
U.S. Appl. No. 17/471,034, filed Sep. 9, 2021 Notice of Allowance dated Jun. 4, 2025.

(56) References Cited

OTHER PUBLICATIONS

U.S. Appl. No. 17/731,169, filed Apr. 27, 2022 Non-Final Office Action dated Jul. 3, 2025.
U.S. Appl. No. 17/731,169, filed Apr. 27, 2022 Restriction Requirement dated Apr. 15, 2025.
U.S. Appl. No. 16/206,890, filed Nov. 30, 2018 Notice of Allowance dated Oct. 7, 2025.
U.S. Appl. No. 16/653,594, filed Oct. 15, 2019 Board Decision dated Jul. 30, 2025.
U.S. Appl. No. 16/653,594, filed Oct. 15, 2019 Non-Final Office Action dated Oct. 7, 2025.
U.S. Appl. No. 16/777,685, filed Jan. 30, 2020 Notice of Allowance dated Sep. 10, 2025.
U.S. Appl. No. 16/930,209, filed Jul. 15, 2020 Non-Final Office Action dated Sep. 2, 2025.
U.S. Appl. No. 17/127,587, filed Dec. 18, 2020 Board Decision dated Sep. 9, 2025.

* cited by examiner

MAGNETIC TRAJECTORY PREDICTION AND POSITION IDENTIFICATION

PRIORITY

This application claims the benefit of priority to U.S. Provisional Application No. 63/083,624, filed Sep. 25, 2020, which is incorporated by reference in its entirety into this application.

SUMMARY

Briefly summarized, embodiments disclosed herein are directed to trackable medical devices with improved magnetic location or orientation identification, and improved trajectory prediction.

Magnetic based tracking systems, such as those used to track medical devices, needles, catheters, or the like, rely on detecting magnetic field of a magnetizable component associated with the trackable medical device. In an embodiment, the trackable medical device can include a catheter placement system having a needle that can be magnetized to provide a magnetic field. The magnetic tracking system can be configured to detect a strength or signature of the magnetic field to determine a location, orientation, or trajectory of a needle of the catheter placement system.

However, additional components of the catheter placement system that are also formed of a magnetizable materials can provide additional magnetic fields. The strength or signature of these secondary magnetic fields can obscure or interfere with the strength or signature of the first magnetic field, inhibiting the performance of the tracking system to accurately determine the location, orientation, or trajectory of the needle. Disclosed herein are medical devices including a needle formed of a magnetizable material, and additional components formed of a non-magnetizable material to inhibit obstruction or interference of the first magnetic field from the needle.

However, replacing components formed of magnetizable materials, with the same components formed of non-magnetizable materials presents additional problems. Non-magnetizable materials present different mechanical properties, and as such, the performance of these components can vary greatly leading to reduced function or failure of the medical device overall. Also disclosed herein are components formed of non-magnetizable materials and configured to provide the same mechanical performance as components formed of the magnetizable materials.

Disclosed herein is a trackable catheter placement system including, a needle formed of a magnetizable material and magnetized to produce a magnetic field having one or both of a magnetic field strength and a magnetic field signature detectable by a sensor of a tracking system, and a spring formed of a non-magnetizable material and configured to display the same mechanical performance properties as a spring formed of the magnetizable material.

In some embodiments, the non-magnetizable material includes copper, beryllium, an alloy including copper and beryllium, or a silver coated copper beryllium alloy. In some embodiments, the magnetizable material includes 17-7 precipitation hardened stainless steel. In some embodiments, the spring includes a wire core diameter of 0.0113±0.001 inches. In some embodiments, the spring includes between 30 and 37 active coils. In some embodiments, the spring includes a solid length of between 0.45 inches and 0.49 inches. In some embodiments, the spring includes a coil pitch angle of between 12 degrees and 16 degrees.

In some embodiments, the spring includes a spring diameter of 0.205±0.005 inches. In some embodiments, the spring includes 3 dead coils at a distal end and 2 dead coils at a proximal end. In some embodiments, the spring includes a distal flared diameter of 0.215 inches. In some embodiments, the tracking system includes a passive magnetic tracking system configured to detect a magnetic field strength of the needle. In some embodiments, the tracking system includes an electro-magnetic tracking system configured to detect a magnetic field signature of the needle.

Also disclosed is a method of tracking a catheter placement system including, providing a catheter placement system having a needle formed of a magnetizable material, and a spring formed of a non-magnetizable material and configured to display the same mechanical properties as a spring formed of the magnetizable material, magnetizing the catheter placement system, producing a magnetic field from the needle, having a magnetic field strength or a magnetic field signature, and detecting the magnetic field by a sensor of a tracking system.

In some embodiments, the non-magnetizable material includes copper, beryllium, an alloy including copper and beryllium, or a silver coated copper beryllium alloy. In some embodiments, the magnetizable material includes a ferrous material, steel, stainless steel, 304-stainless steel, or 17-7 precipitation hardened stainless steel. In some embodiments, the spring includes a wire core diameter of 0.0113±0.001 inches. In some embodiments, the spring includes between 30 and 37 active coils. In some embodiments, the spring includes a solid length of between 0.45 inches and 0.49 inches. In some embodiments, the spring includes a coil pitch angle of between 12 degrees and 16 degrees.

In some embodiments, the spring includes a spring diameter of 0.205±0.005 inches. In some embodiments, the spring includes 3 dead coils at a distal end and 2 dead coils at a proximal end. In some embodiments, the spring includes a distal flared diameter of 0.215 inches. In some embodiments, the method further includes determining one of a location, orientation, or trajectory of the needle. In some embodiments, the tracking system includes a passive magnetic tracking system configured to detect a magnetic field strength of the needle. In some embodiments, the tracking system includes an electro-magnetic tracking system configured to detect a magnetic field signature of the needle.

Also disclosed is a method of manufacturing a trackable medical device including, providing a medical device including a needle extending from a distal end of a body and a spring disposed within the body, the needle configured to access a vasculature of a patient and formed of one of 304-stainless steel or 17-7 precipitation hardened stainless steel, the spring including copper and beryllium, placing a portion of the medical device within a magnetizer that includes a magnetic element, magnetizing the needle and the spring, and providing a first magnetic signal from the needle.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Figure 1A:
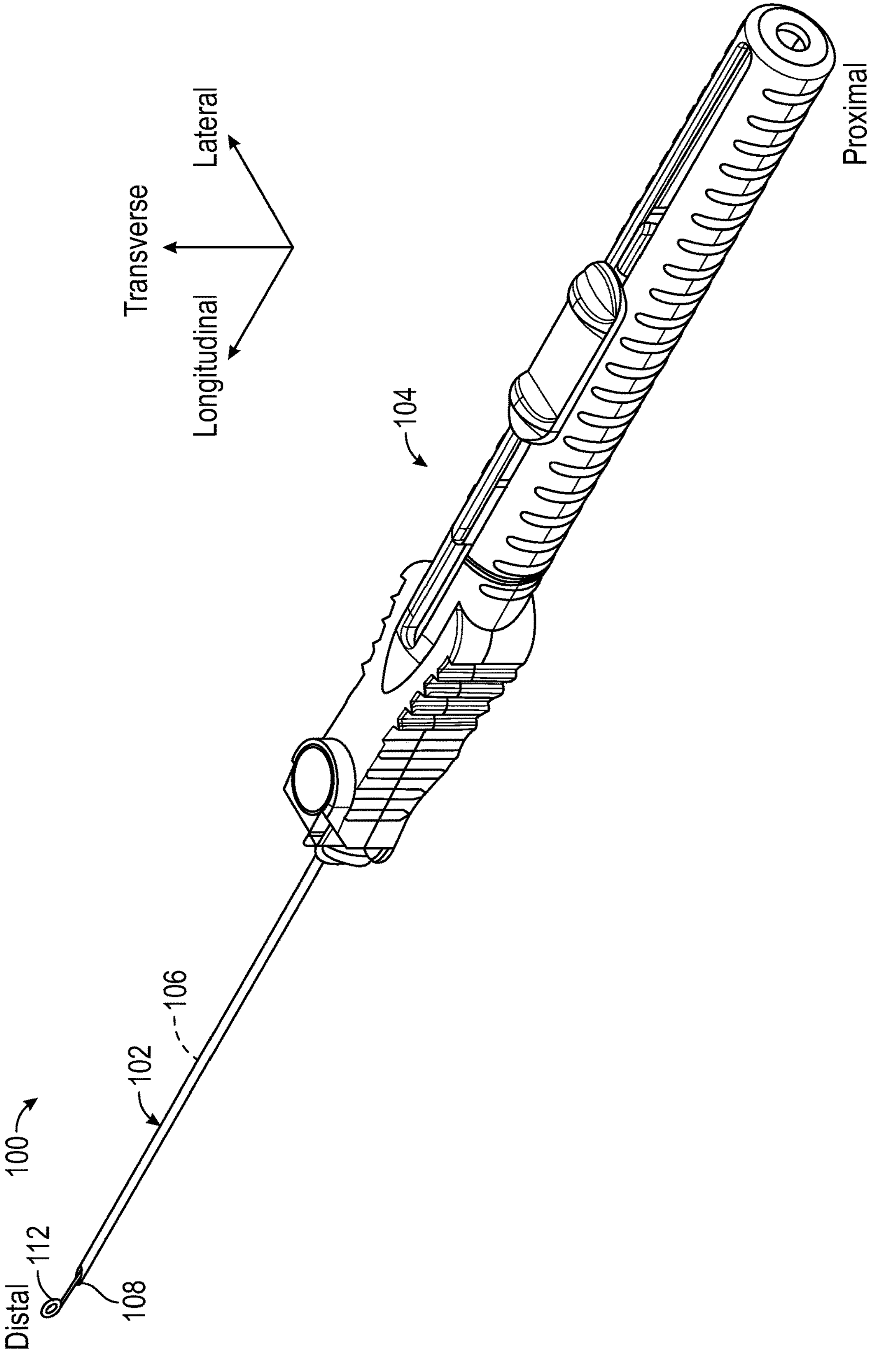
FIG. 1A shows a perspective view of an exemplary medical device, in accordance with embodiments disclosed herein.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a needle disclosed herein includes a portion of the needle intended to be near a clinician when the needle is used on a patient. Likewise, a "proximal length" of, for example, the needle includes a length of the needle intended to be near the clinician when the needle is used on the patient. A "proximal end" of, for example, the needle includes an end of the needle intended to be near the clinician when the needle is used on the patient. The proximal portion, the proximal end portion, or the proximal length of the needle can include the proximal end of the needle; however, the proximal portion, the proximal end portion, or the proximal length of the needle need not include the proximal end of the needle. That is, unless context suggests otherwise, the proximal portion, the proximal end portion, or the proximal length of the needle is not a terminal portion or terminal length of the needle.

With respect to "distal," a "distal portion" or a "distal end portion" of, for example, a needle disclosed herein includes a portion of the needle intended to be near or in a patient when the needle is used on the patient. Likewise, a "distal length" of, for example, the needle includes a length of the needle intended to be near or in the patient when the needle is used on the patient. A "distal end" of, for example, the needle includes an end of the needle intended to be near or in the patient when the needle is used on the patient. The distal portion, the distal end portion, or the distal length of the needle can include the distal end of the needle; however, the distal portion, the distal end portion, or the distal length of the needle need not include the distal end of the needle. That is, unless context suggests otherwise, the distal portion, the distal end portion, or the distal length of the needle is not a terminal portion or terminal length of the needle.

To assist in the description of embodiments described herein, and as shown in FIG. 1A, a longitudinal axis extends substantially parallel to an axial length of a needle 102. A lateral axis extends normal to the longitudinal axis, and a transverse axis extends normal to both the longitudinal and lateral axes.

As used herein, a "magnetic strength" is defined as an absolute measurement of a magnetic field strength. As used herein, a "magnetic signature" is defined as a difference in one or more parameters that define an electro-magnetic field. For example a wave length, wave frequency, wave amplitude, combinations thereof, or the like.

Unless defined otherwise, all technical and scientific terms used herein have the same meaning as commonly understood by those of ordinary skill in the art.

Figure 1B:
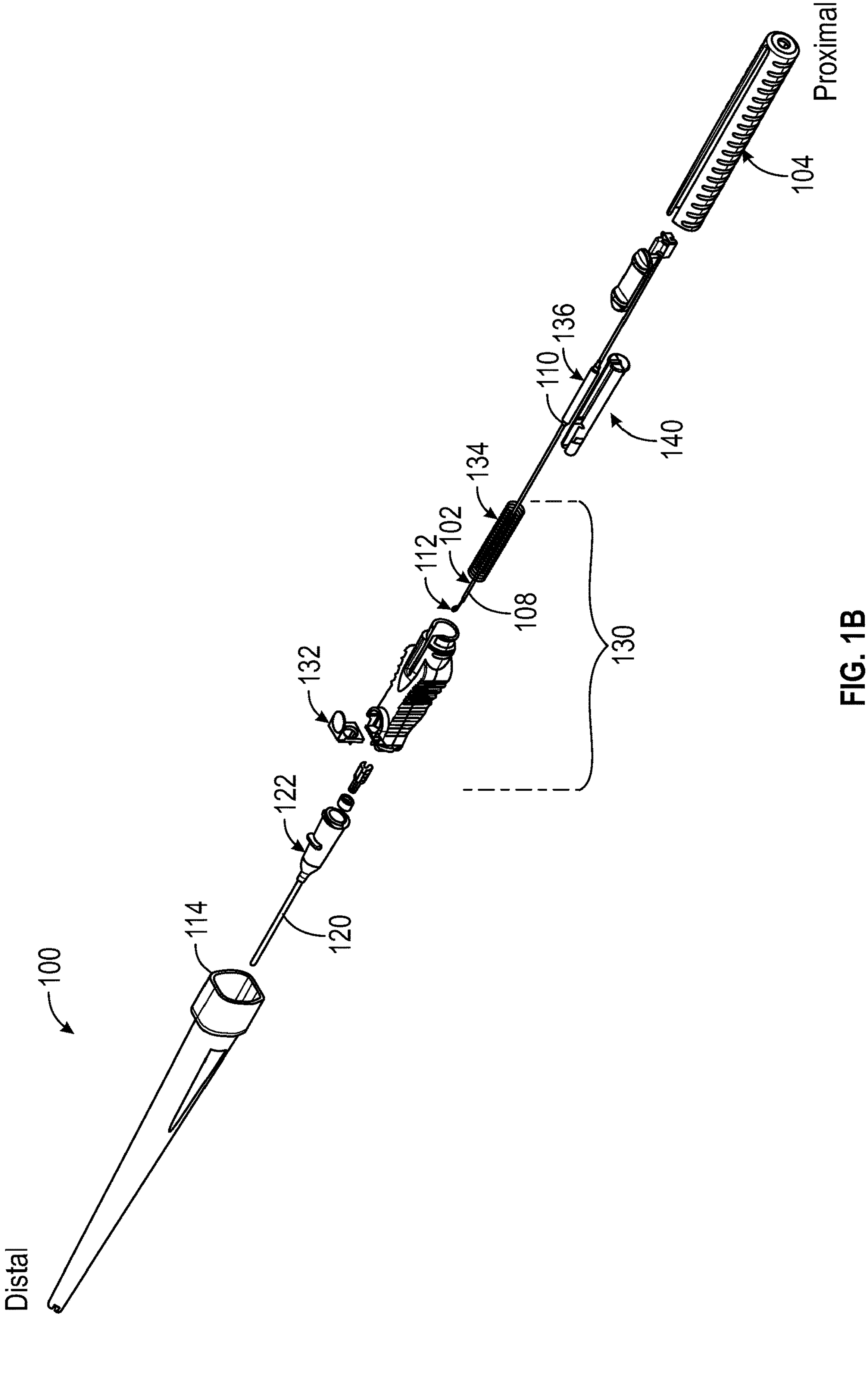
FIG. 1B shows an exploded view of an exemplary medical device, in accordance with embodiments disclosed herein.

FIGS. 1A-1B show details of an exemplary medical device 100 generally including an elongate cannula or needle 102 extending along a longitudinal axis and supported at a proximal end by a hub, housing, or elongate body 104. In an embodiment, the medical device 100 can include a catheter placement system, needle, cannula, trocar, stylet, guidewire, or similar elongate medical device including a portion configured to be inserted subcutaneously into a patient. In an embodiment, the catheter placement system can be an ACCUCATH™ catheter placement system, or the like. As used herein, an exemplary medical device 100 may also be referred to as a catheter placement system 100, however this is not intended to be limiting. Similarly, the body 104 is also not intended to be limiting and can also include various handles, housings, connectors, extension legs, or similar support or connecting structures. It will be appreciated that, as used herein, the term "medical device" is exemplary and not intended to be limiting, and embodiments described herein can be used for any device that can be tracked by a magnetic tracking system. For example, trackable devices used within the construction industry, surveying, or the like.

In an embodiment, the needle 102 can define a lumen 106 extending along the longitudinal axis and providing fluid communication between a distal tip 108 of the needle 102 and a proximal end 110 of the needle 102. In an embodiment, the needle 102 or cannula can define a sharpened distal tip 108. In an embodiment, the medical device 100 can include a catheter 120, sheath, or similar tubular device disposed on an outer surface of the needle 102. The catheter 120 can be supported by a catheter hub 122. The catheter 120 can be selectively detachable from the needle 102. In an embodiment, the medical device 100 can include a second elongate medical device, e.g. a guidewire 112, or the like, extending through the needle lumen 106. In an embodiment, the second elongate medical device can be formed of a non-magnetizable material, as described herein.

In an embodiment, the needle 102 can be slidably engaged with the body 104 along the longitudinal axis. In an embodiment, the medical device 100 can include a needle retraction system 130. The needle retraction system 130 can be configured to withdraw the needle 102 proximally into the body 104 after the catheter 120 has been placed successfully. Advantageously, the needle 102 can be withdrawn into the body 104 to mitigate accidental needle stick injuries and/or mitigate contamination of fluids, e.g. blood, disposed thereon.

The needle retraction system 130 can include an actuator 132 and a biasing member 134, e.g. compression spring or the like, disposed within a portion of the body 104. The biasing member 134 can be coupled to the needle 102 and can bias the needle 102 towards a retracted position, disposed within the body 104. The actuator 132 can be configured to retain the needle 102 in an extended position, where a portion of the needle 102 is disposed distally of a distal end of the housing 104, e.g. as shown in FIG. 1. Actuating the actuator 132 can allow the biasing member 134 to urge the needle towards the retracted position within the body 104. Further details of catheter placement systems including needle retraction systems can be found in U.S. Pat. Nos. 5,865,806; 5,911,705; 8,728,035; 9,162,037; and 10,220,191, each of which are incorporated by reference in their entirety into this application.

In an embodiment, the medical device 100 can include a blood flash indicator 136 in fluid communication with the needle. The blood flash indicator 136 can be configured to indicate when a distal tip of the needle 108 has accessed a vasculature of a patient. In an embodiment, the medical device 100 can include a guidewire advancement assembly 140 slidably engaged with the body 104 and configured to selectively advance a guidewire 112 through a needle lumen 106 and into a vasculature of the patient. In an embodiment, the medical device 100 can include a cap 114 disposed over the needle 102 extending from the distal end of the body 104, and selectively removable therefrom and configured to protect the needle 102 during storage or transport.

In an embodiment, a portion of the medical device 100 can be magnetized, e.g. needle 102, and used with various tracking systems that employ one or more tracking modalities. Exemplary modalities can include ultrasound, passive ("permanent") magnetic tracking, electro-magnetic tracking, combinations thereof, or the like.

Figure 2A:
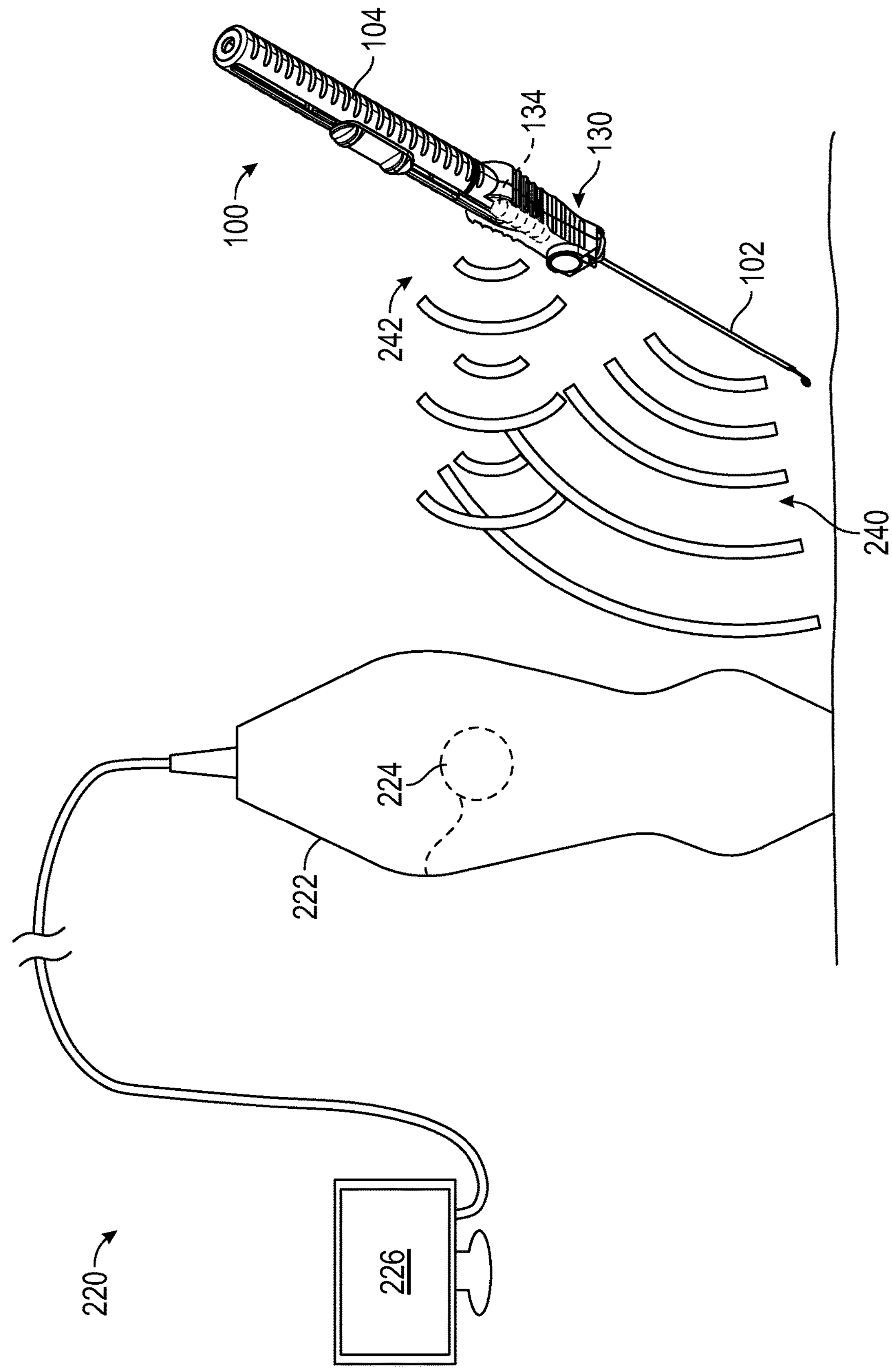
FIG. 2A shows an exemplary tracking system used to track a medical device including magnetizable components, in accordance with embodiments disclosed herein.
Figure 2B:
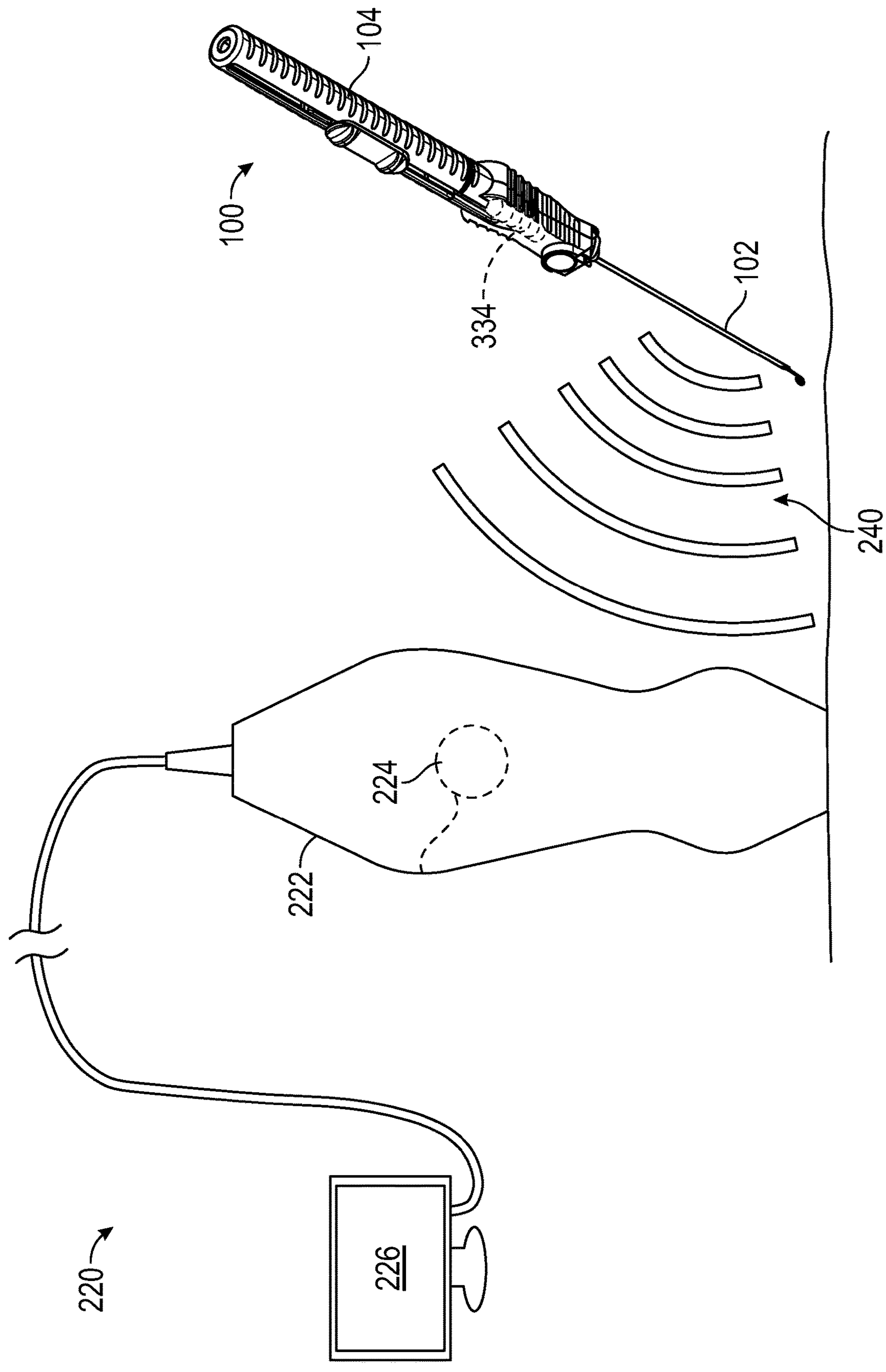
FIG. 2B shows an exemplary tracking system used to track a medical device including non-magnetizable components, in accordance with embodiments disclosed herein.

FIGS. 2A-2B show details of an exemplary tracking system 220. The tracking system 220 can generally include a probe 222 communicatively coupled to a console 226. The probe 222 can include an ultrasound transducer and one or more sensors 224. The ultrasound transducer can be configured to emit and receive acoustic signals to provide an image of a subcutaneous target location, e.g. a target vessel or the like. The one or more sensors 224 can be configured to detect one or more modalities, e.g. magnetic field, electromagnetic field, or the like. In an embodiment, the tracking system 220 can utilize an ultrasound modality to image a subcutaneous target area, and also use a magnetic modality to track a position of the medical device 100 relative to the probe 222. The tracking system 220 can further include a console 226 having a display configured to show both the imaged subcutaneous target area, as well as the position of the medical device 100 relative to the target area.

In an embodiment the medical device 100, or a portion thereof, can include a magnetizable material for example a metal, alloy, composite, steel, stainless steel, 304-stainless steel, 17-7 Precipitation Hardened Stainless Steel ("17-7 PH SS"), or similar magnetizable material. In an embodiment, the needle 102 of the medical device 100 can be formed of a magnetizable material and can be magnetized to provide a passive ("permanent") magnetic field. In an embodiment, the medical device 100 can include one more components configured to produce an electro-magnetic field from the needle 102. As such, the magnetized medical device 100 creates a magnetic field that can be detected by the probe 222 of the tracking system 220. The tracking system 200 can detect and analyze the strength and/or signature of the magnetic field and determine a position, orientation, or trajectory of the medical device 100 relative to the tracking system 220.

Further details of such multi-modal tracking systems can be found, for example, in the following: U.S. Pat. Nos. 8,388,541, 8,971,994, 9,492,097, 9,636,031, 10,238,418, 10,966,630, 11,027,101, U.S. 2018/0116551, U.S. 2018/0304043, U.S. 2019/0069877, U.S. 2019/0099108, U.S. 2020/0054858, U.S. 2020/0237255, and U.S. 2020/0345983, each of which are incorporated by reference in their entirety into this application.

With continued reference to FIG. 2A, an exemplary medical device can include one or more components, e.g. spring 134, which are separate from the magnetized needle 102, and also formed of a magnetizable material, e.g. steel. The one or more components can include springs, clips, needle safety clips, guidewire advancement assemblies, blood flash indicators, portions thereof, or similar structures that rely on steel or similar ferrous material to provide preferred mechanical properties and provide a desired performance of mechanical functions. These components, although may not be intentionally magnetized, may still provide a second magnetic signal 242 that is different in strength and/or magnetic signature from the first magnetic signal 240 of the needle 102.

The second magnetic signal 242 of the components can obscure or interfere with the first magnetic signal 240 of the needle 102, making the first magnetic signal 240 harder to distinguish and reducing the accuracy of the tracking system 220 to predict a location, orientation, or trajectory of the needle 102.

In an embodiment, the second magnetic signal 242 can obscure the strength of the first magnetic signal 240 by providing a second magnetic signal 242 having a second magnetic field strength. This second magnetic field strength, or "background noise," can reduce the signal to noise ratio between the first magnetic signal 240 relative to the background noise making the first magnetic signal 240 harder to distinguish, or obscuring the first magnetic signal 240 altogether.

In an embodiment, the second magnetic signal 242 of the components can interfere with the signature of the first magnetic signal 240. For example, where the first magnetic signal 240 is provided as an electro-magnetic wave, having a distinct magnetic signature, the second magnetic signal 242 can interfere with the first magnetic signal 240 through constructive or destructive waves, or the like. The obstruction or interference of the first magnetic signal 240 by the second magnetic signal 242 can be termed as providing a "dirty" signal that can reduce the accuracy of the tracking system 220 in determining a location, orientation, or trajectory of the medical device 100.

As shown, in FIG. 2B, in an embodiment, the medical device 100 can include components formed of a non-magnetizable material, e.g. non-magnetizable spring 334. Exemplary non-magnetizable materials can include non-ferrous metals, alloys, plastics, polymers, copper, beryllium, copper beryllium alloys, silver coated copper beryllium, or the like. The non-magnetizable components 334 provide little or no magnetic signal and, as such, the medical device 100 provides only the first, "clean" magnetic signal 240, e.g. from the needle 102. The first magnetic signal 240 is unobstructed and/or un-interfered by any secondary magnetic signals. The signal strength is discernable above a reduced background noise, i.e. a larger signal to noise ratio, and the signature of the signal is not interfered with. This increases the accuracy of tracking system 220 to track and predict the location, orientation or trajectory of the medical device 100.

It is important to note, however, that non-magnetizable metals, alloys, plastics, polymers, copper, beryllium, copper beryllium alloys, silver coated copper beryllium, or the like display different mechanical properties from that of magnetizable materials, e.g. steel, stainless steel, 304-stainless steel, 17-7 PH SS, or the like. Exemplary mechanical properties can include, density, minimum tensile strength, modulus of elasticity (stretch), modulus of torsion (compression), sheer strength, malleability, combinations thereof, or the like. As such the mechanical performance of the non-magnetizable components can differ substantially from non-magnetizable components leading to reduced performance or failure of the medical device.

Figure 3:
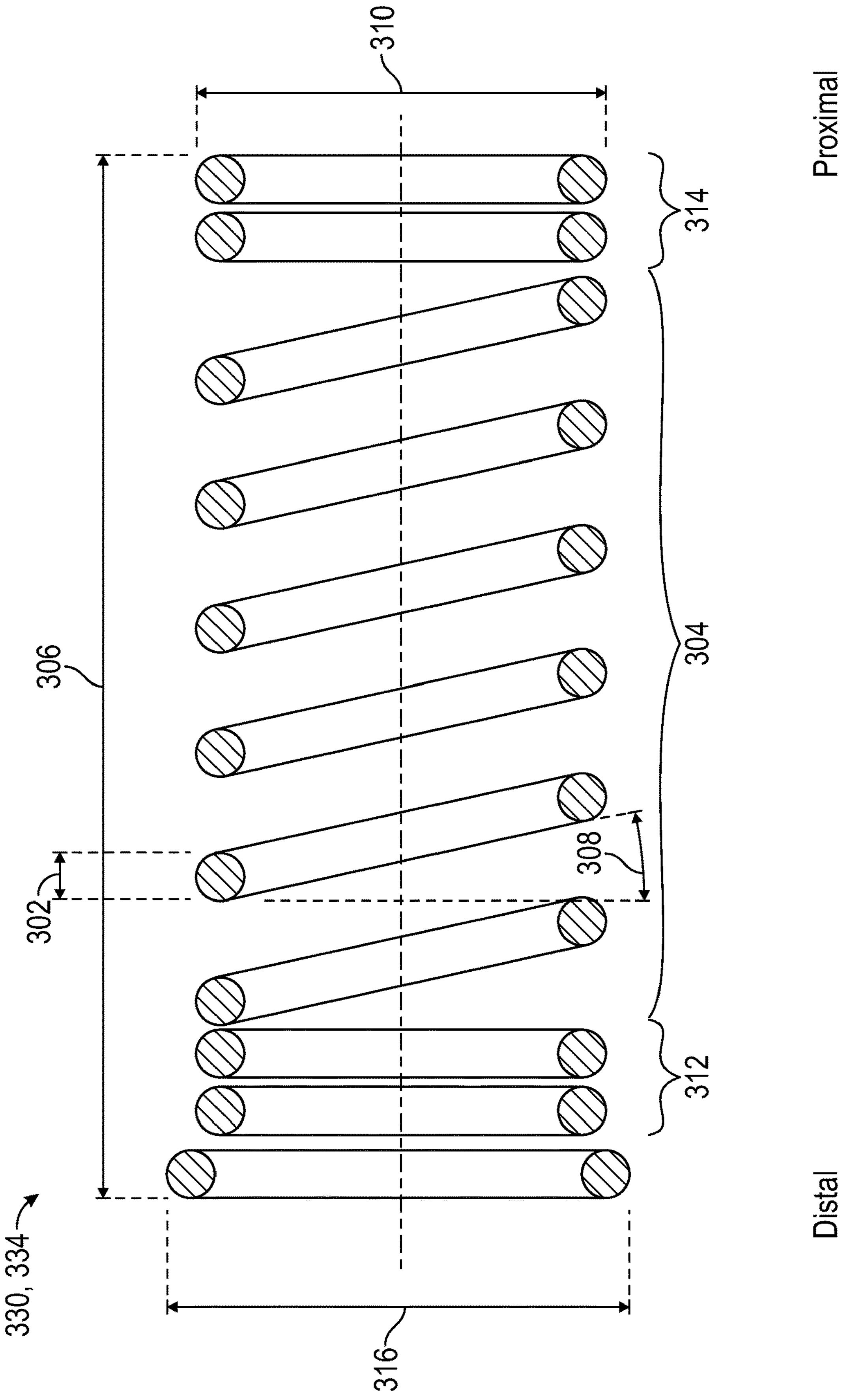
FIG. 3 shows configuration details of an exemplary spring, in accordance with embodiments disclosed herein.

FIG. 3 and Table 1 below show configuration details of a spring 330 formed of a magnetizable material, e.g. 304-stainless steel, and configuration details of a spring 334 formed of a non-magnetizable material, e.g. silver coated copper beryllium. For example, Table 1 below shows configuration details for an exemplary magnetizable spring 330 and an exemplary non-magnetizable spring 334. The non-magnetizable spring 334 can be formed of silver coated copper beryllium and provide the same mechanical performance as the magnetizable spring 330 formed of 304-stainless steel. Table 1 below compares the differences in spring design between a magnetizable spring 330 and a non-magnetizable spring 334.

TABLE 1

Example Difference in Spring Configuration
Example Difference in Spring Design

| | Spring Material | Magnetizable Spring 330 | Non-magnetizable Spring 334 |
|---|---|---|---|
| 302 | Wire Core-Diameter [in] | 0.010 ± 0.001 | 0.0113 ± 0.001 |
| 304 | Active Coils [#] | 44 | 33.5 |
| 306 | Solid Length [in] | 0.510 | 0.472 |
| 308 | Pitch Angle [deg] | 11.35 | 14.2 |
| 310 | Spring Diameter [in] | 0.195 ± 0.003 | 0.205 ± 0.005 |
| 312 | Dead Coils at Distal end [#] | 4 | 3 |
| 314 | Dead Coils at Proximal end [#] | 2 | 2 |
| 316 | Distal Flared Diameter [in] | 0.212 | 0.215 |

FIG. 3 shows an exemplary spring indicating the configuration measurements listed in Table 1. The wire core diameter parameter (in.) 302 is the diameter of the wire that forms the spring 330, 334. The active coils parameter (#) 304, is the number of active coils within spring 330, 334. As shown, these active coils 304 are disposed between dead coils 312, 314 disposed at either end of the spring 330, 334. However, it will be appreciated that the spring 330, 334 can include one or more active coils 304 at one of the proximal end or distal end, or can include one or more dead coils 312, 314 disposed at a mid-point of the spring 330, 334. A solid length parameter (in.) 306, is the longitudinal length of the spring from a proximal end to a distal end. A pitch angle parameter (deg) 308, is the angle of the coil 304, 312, 314 relative to an axis that extends perpendicular to the longitudinal axis of the spring 330, 334. A spring diameter parameter (in.) 310 is the outer diameter of the spring extending along an axis that extends perpendicular to the longitudinal axis. The dead coils (#) at the distal end 312, and the dead coils (#) at the proximal end 314 parameters are the number of coils that extend substantially perpendicular to the longitudinal axis, and disposed at the distal end and proximal end, respectively. The distal flared diameter parameter (in.) 316 is the widest diameter of the spring extending along an axis that extends perpendicular to the longitudinal axis at one or both of the proximal end and the distal end.

Advantageously, the difference in configuration of the non-magnetizable spring 334 from that of the magnetizable spring 330 provides a spring that has the same mechanical performance with little or no change in the overall dimensions of the spring. For example, a difference in one of the number of active coils, a pitch angle of the coils, or the diameter of the wire-core, of the spring can modify a mechanical performance of the non-magnetizable spring 334 to be equal to that of a magnetizable spring 330 while maintaining a diameter or length of the spring as substantially the same. Advantageously, the non-magnetizable spring 334, configured as such can be used in existing designs of medical device 100 to provide the same mechanical performance without having to reconfigure the dimensions of the medical device 100 to accommodate a completely different spring.

Figure 4A:
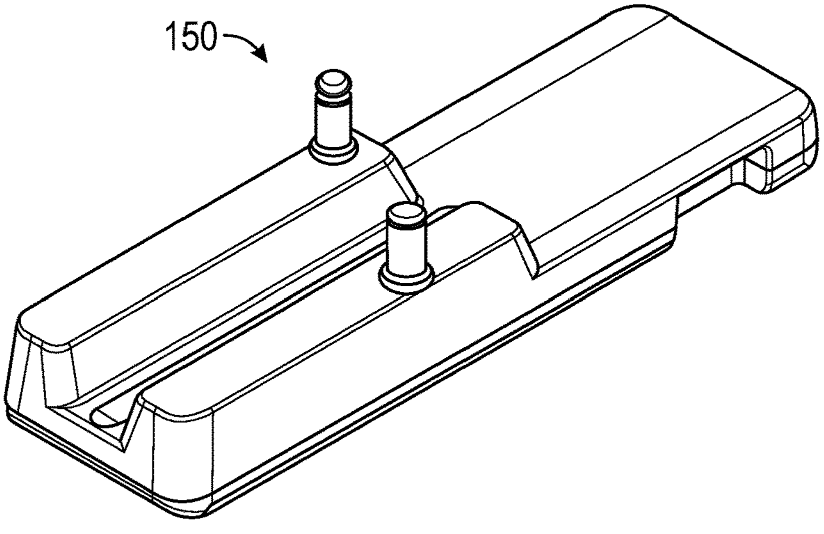
FIG. 4A shows a perspective view of an exemplary magnetizer that can magnetize the medical device of FIG. 1A, in accordance with embodiments disclosed herein.
Figure 4B:
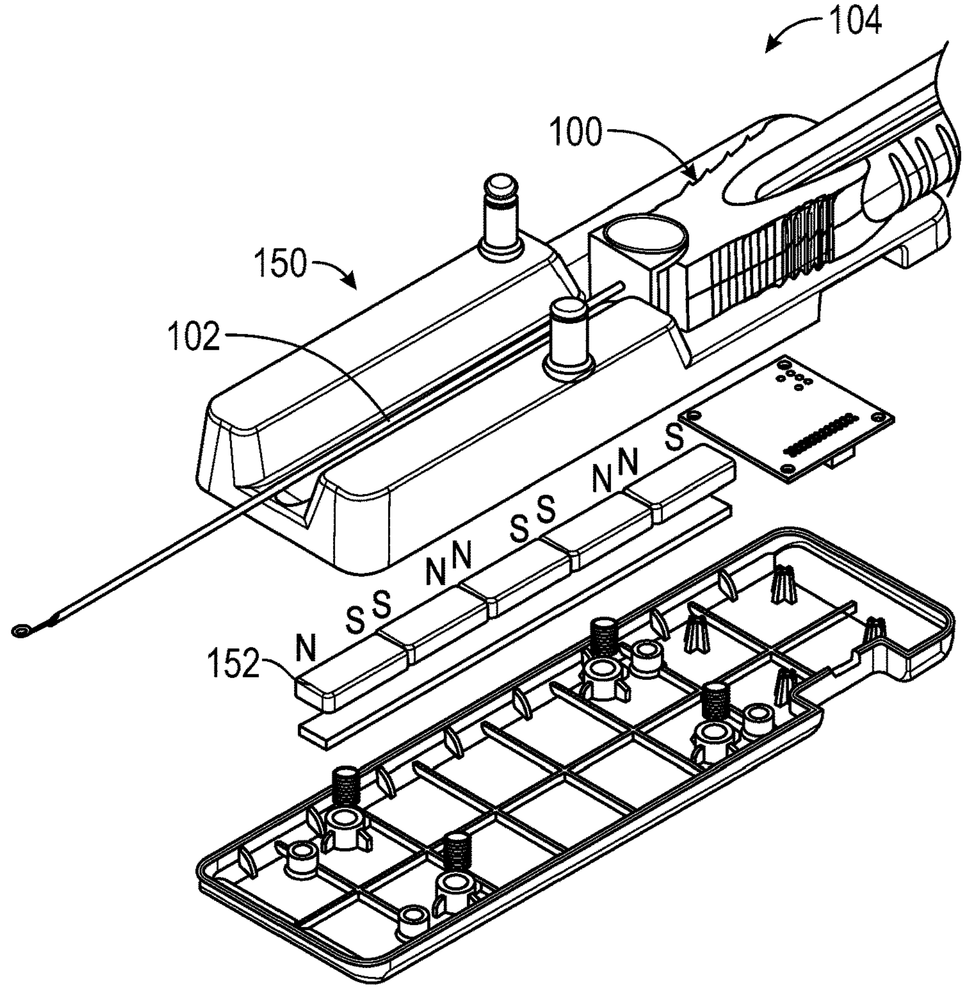
FIG. 4B shows an exploded view the magnetizer device of FIG. 4A, in accordance with embodiments disclosed herein.

As shown in FIGS. 4A-4B, in an embodiment, an exemplary method of magnetizing the medical device 100 is provided. As shown in FIG. 4A, a magnetization device ("magnetizer") 150 is provided that includes one or more magnetic elements 152. The magnetic element 152 can include either permanent magnets, electro-magnets, or combinations thereof. The magnetization device 150 can be configured to align the medical device 100 relative to the magnetic elements 152 at a predetermined orientation. The magnetization device 150 then exposes the medical device 100, or a portion thereof, to the magnetic elements 152 to magnetize the medical device 100. Exposure of the medical device 100 to the magnetic elements 152 aligns the electrons of the metallic portions of the medical device 100 and imparts a magnetic field on the medical device 100. In an embodiment, the field lines of the magnetic field are aligned with an axis of the medical device 100. Further details of exemplary magnetizing devices can be found in U.S. Pub. No. 2018/0310955 which is hereby incorporated by reference in its entirety.

Advantageously, magnetizing the medical device 100 directly provides a simplified manufacture process, reducing complexity, and improving manufacturing speed and costs. This is relative to a medical device that includes a separate, permanent, magnetic material included with the medical device 100 to provide a magnetic field. For example, providing a needle 102 of a medical device 100 formed of a first material, e.g. 304 stainless steel, and including a permanent magnet formed of a second material, e.g. ferrite, requires increased complexity in combining the two contrasting materials into the one device. Further, the device requires aligning the magnetic field with the orientation of the needle 102. Similarly, forming a medical device 100 including an electromagnetic element requires yet further complexity in manufacturing and requires a power source.

As will be appreciated, one or more components of the medical device 100 can become magnetized when the medical device 100 is placed in proximity to the magnetizer 150. Since these additional components, e.g. magnetizable spring 134, are positioned and aligned differently relative to the magnetic elements 152 of the magnetizer 150, the secondary magnetic signal(s) 242 imparted on these one or more components can interfere with the primary magnetic signal 240 of the needle 102, as described herein.

In an embodiment, a medical device 100 is provided including a non-magnetizable spring 334 being formed of a copper, beryllium, copper beryllium alloy, silver coated copper beryllium, or combinations thereof, and configured as described in Table 1. Advantageously, the non-magnetizable spring 334 can be particularly resistant to being magnetized when the medical device 100 is exposed to the magnetizer 150, thereby reducing or eliminating any secondary magnetic signal 242 or "background noise" from the spring 334. Further, the spring 334 formed of copper, beryllium, or alloys thereof and configured as described in Table 1, can provide the same outer dimensions and the same mechanical performance as the magnetizable spring 134 formed of steel, stainless steel, 304 stainless steel, or the like. As such, the non-magnetizable spring 334 can be placed within the medical device 100 without any further redesign or reconfiguration of the medical device 100 reducing inventory and associated costs in manufacturing and logistics.

TABLE 2

Composition comparison of 17-7 Stainless Steel and 304 Stainless Steel

| Chemical | 17-7 Stainless Steel (%) | 304 Stainless Steel (%) |
|---|---|---|
| Chromium | 16.0-18.0 | 18.0-20.0 |
| Nickel | 6.50-7.75 | 8.0-10.5 |
| Aluminum | 0.75-1.50 | 0.00 |
| Manganese | up to 1.00 | up to 2.0 |
| Silicon | up to 1.00 | up to 0.75 |
| Carbon | up to 0.09 | up to 0.08 |
| Phosphorus | up to 0.04 | up to 0.045 |
| Sulfur | up to 0.03 | up to 0.03 |
| Nitrogen | 0.00 | up to 0.10 |
| Iron | makes up the remainder | makes up the remainder |

In an embodiment, the medical device 100 can include a needle 102 formed of 17-7 PH SS. Table 2 above compares the chemical composition of 17-7 Stainless Steel with that of 304 Stainless Steel. In an embodiment, the 17-7 stainless steel, as detailed in Table 2, is further treated using a precipitation hardening process. The precipitation hardening process generally includes applying a solution treatment that includes heating the 17-7 stainless steel to a relatively high temperature and treating with a solution. This is followed by a quenching treatment which includes rapidly cooling the solution-soaked metal. This is followed by an aging process which includes heating the metal to a relative medium temperature followed by rapid cooling. The precipitation hardening process can be performed in a vacuum, or an inert atmosphere, and can include temperatures ranging from between 900 degrees and 1150 degrees Fahrenheit. However, it will be appreciated that higher and lower temperatures are also contemplated. In an embodiment, the process can range in length time from one to several hours, depending on the exact material and characteristics desired, although shorter and longer times are also contemplated. The precipitation hardening process of 17-7 stainless steel provides 17-7 PH SS which includes uniformly dispersed particles within the metal's grain structure. This can hinder motion of the particles and thereby providing improved mechanical strength properties.

The 17-7 PH SS can display comparable, or improved, mechanical and corrosion resistant properties to that of standard 304 stainless steel ("304 SS"). Further, 17-7 PH SS can demonstrate improved magnetic permeability allowing the needle 102 of the medical device 100 to develop a stronger magnetic field, relative to devices formed of 304 stainless steel, when subjected to the same magnetization methods using the magnetizer 150, as described herein.

Advantageously, devices formed of 17-7 PH SS provide surprisingly improved tracking properties, relative to similar devices formed of 304 stainless steel. As such, medical devices formed of 17-7 PH SS can provide improved drop-out distance of approximately double the distance, an improved pairing distance of approximately double the distance, an improved true position vs. calculated position by reducing the error distance by up to half, or an improved immunity to magnetic interference. The improved immunity to magnetic interference can be shown by reducing the error distance from between 34% and 57%, as seen in devices formed of 304 stainless steel, down to less than 3%, as seen in similar devices formed from 17-7 PH SS, as described in more detail herein. (See Table 4). Further, there was less variation in magnetic field strength between individual needles formed of 17-7 PH SS when subjected to the same processes of magnetization. Further, needles formed of 17-7 PH SS were more resistant to demagnetization. Worded differently, the strength of magnetic fields were more reliable. As such, in an embodiment, a medical device 100 is provided including a needle 102 formed of 17-7 PH SS and a spring 334 formed of copper, beryllium, or alloys thereof and configured as detailed in Table 1. As such the medical device 100 can be magnetized by a magnetizer 150 to impart a strong and stable magnetic signal 240 on the needle 102 and minimizing any secondary magnetic signals 242 being imparted on the spring 334. This provides a high signal-to-noise ratio between the primary magnetic signal 240 and the secondary magnetic signal 242 improving accuracy and reliability of tracking the needle 102 using multi-modal tracking systems 220, as described herein.

This invention is further illustrated by the following exemplary experiment(s), which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Experiment 1

This exemplary experiment shows superiority in the magnetic tracking properties of exemplary needles formed of 17-7 PH SS, compared with exemplary needles formed of 304 stainless steel, when magnetized by proximity to a magnetic source, as disclosed herein.

Scope

These exemplary test results illustrate a difference in magnetic tracking performance between three exemplary magnetized needles.

Materials

The three exemplary needle types that were tested include A) a 21 G needle formed of 304 stainless steel; B) an 18 G needle formed of 304 stainless steel; and C) an 18 G needle formed of 17-7 PH SS. The specifications of the three types of needles used in the experiment are set forth below in Table 3:

TABLE 3

Specifications of three types of needles used in the experiment

| Specifications | Needle A | Needle B | Needle C |
|---|---|---|---|
| Gauge (G) | 21G | 18G | 18G |
| Material | 304 Stainless Steel | 304 Stainless Steel | 17-7 PH SS |

Figure 5B:
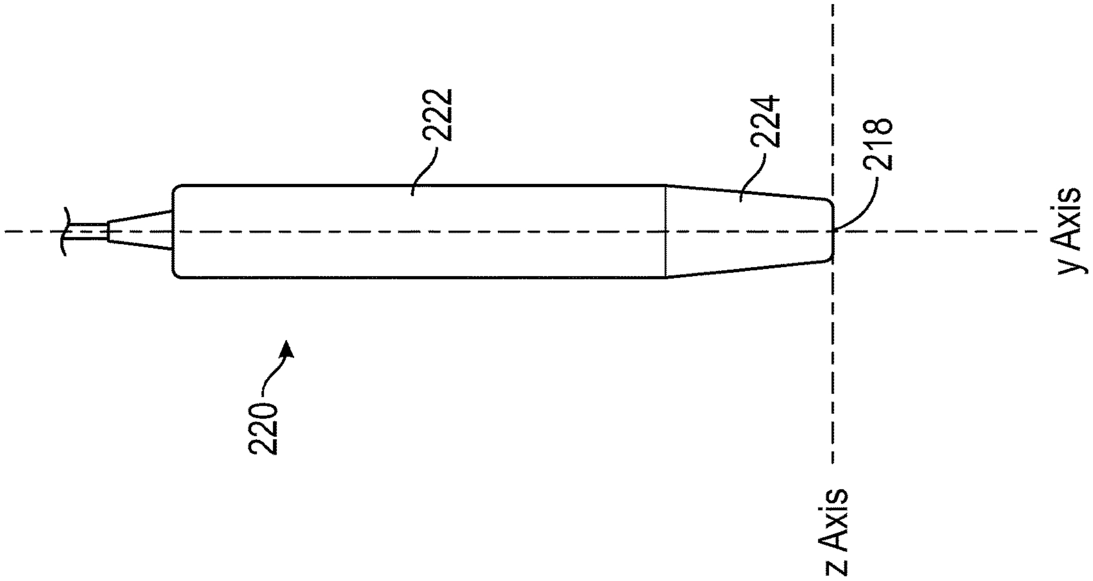
FIG. 5B shows a side view of a sensor of a tracking system including the z-axis and the y-axis, in accordance with embodiments disclosed herein.
Figure 5A:
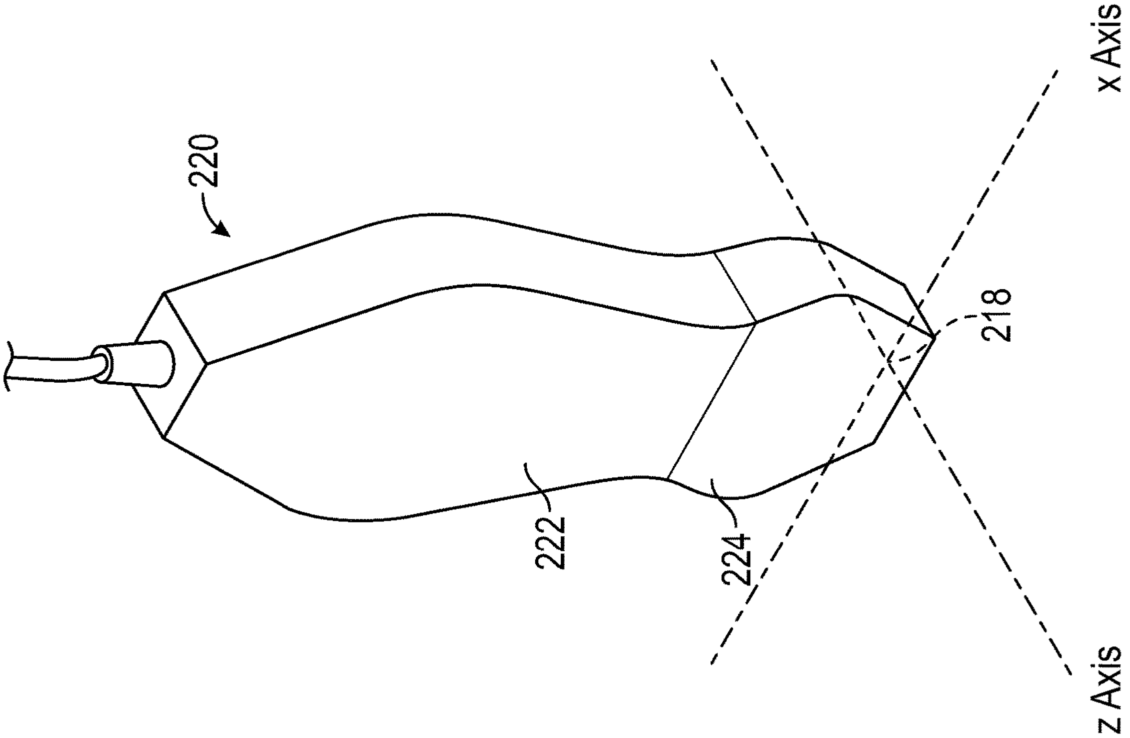
FIG. 5A shows a perspective view of a sensor of a tracking system including the x-axis and the z-axis, in accordance with embodiments disclosed herein.

The tracking system 220 includes a probe 222 and a magnetic sensor 224 configured for detecting a magnetic field. The magnetic tracking properties were quantified based on the position of the test needle 102 relative to the sensor 224 in three-dimensional space. FIGS. 5A-5B show the x, y, and z-axes as defined in three dimensional space relative to the sensor 224 of the tracking system 220. The x, and z-axes extend horizontally and extend normally relative to each other, they axis extends vertically relative to the x, z-axes. The x, y, and z-axes intersect at a center point 218 where the sensor 224 is located.

Methods

The medical device(s) 100 to be tested included three separate needles 102 of each needle type A, B, C (See Table 3), i.e. needle A.1, A.2, A.3, B.1, B.2 etc. for a total of nine needles. As used herein a "true" distance is defined as a distance that is directly measured in three-dimensional space. As used herein a "calculated distance" is defined as a distance that is measured by a tracking system 220, such as those described herein, in three-dimensional space.

Test 1) Drop-Out Distance: As used herein, a drop-out distance is the maximum calculated distance between the magnetized needle 102 and the sensor 224 before the sensor 224 can no longer detect the presence of the needle 102. The test needle 102 was paired with the tracking system 220 and then moved away from the sensor 224 until the tracking system 220 failed to detect the needle 102, i.e. became unpaired. The last known position of the needle 102 was then recorded from the tracking system 220.

Test 2) Pairing Distance: As used herein, a pairing distance is the maximum true distance between the needle 102 and the sensor 224, at which the tracking system 220 can detect the presence of the needle 102, i.e. a successful pairing. The test needle(s) 102 were positioned at a predetermined location as defined by the x, y, and z-axes, and a successful pairing at the location was recorded. The needle 102 was then placed at different predetermined locations that were progressively further from the sensor 224, until the tracking system 220 could no longer pair with the needle 102. The last known successful pairing distance for each needle 102 was recorded.

Test 3) True position vs. Calculated position: As used herein, the true position vs. calculated position is defined as a comparison between the true location of the needle 102, as measured by true distance in three-dimensional space, compared with the calculated position of the needle 102, as measured by the tracking system 220. Initially the needle 102 is placed at a predetermined location, as defined by the x, y, and z-axes, and paired with the tracking system 220. The true position, as defined by the x, y, z-axes is then compared with the calculated position as defined by the tracking system 220 and the differences recorded.

Test 4) Immunity to Magnetic Interference: As used herein, immunity is defined as changes induced by the presence of a magnetic interference source. The changes measured were differences between the true position vs. the calculated position. The needle 102 was paired with the tracking device 220 and positioned at a predetermined location, as defined by the x, y, and z-axes. The true location and the calculated location were recorded without a magnetic interference source present. A constant source of magnetic interference (e.g. a permanent magnet) was introduced, and the difference between the true position vs. the calculated position was re-recorded and compared. In an embodiment, the magnetic interference source was positioned further from the sensor 224 than the needle 102.

Data

Figure 6A:
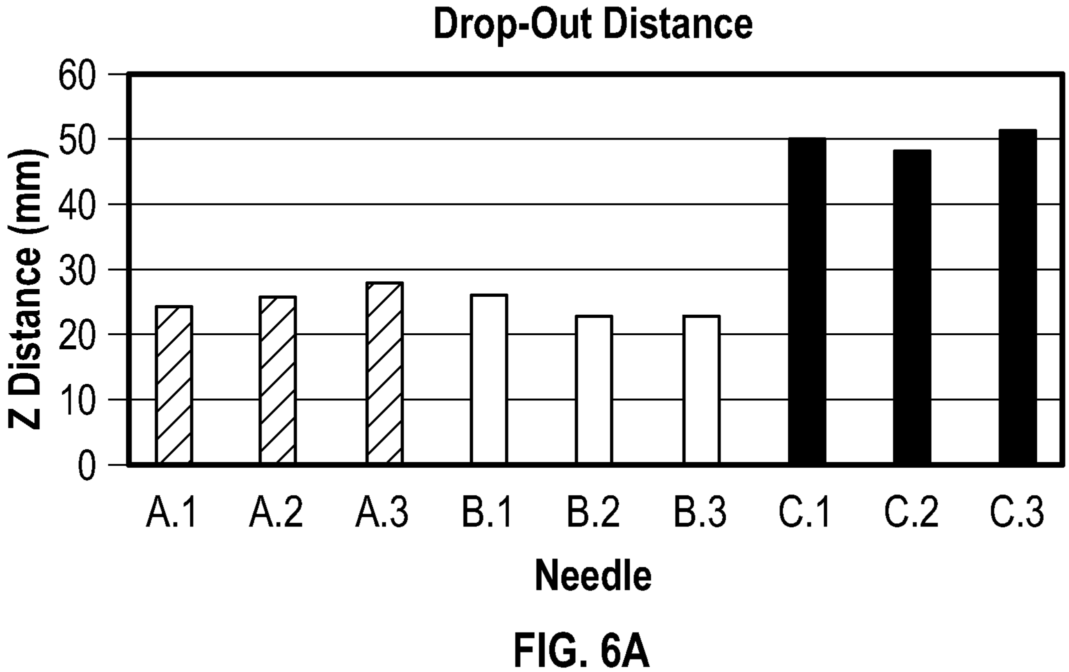
FIGS. 6A-6D show bar charts of the results from testing exemplary medical devices, in accordance with embodiments disclosed herein.
Figure 6B:
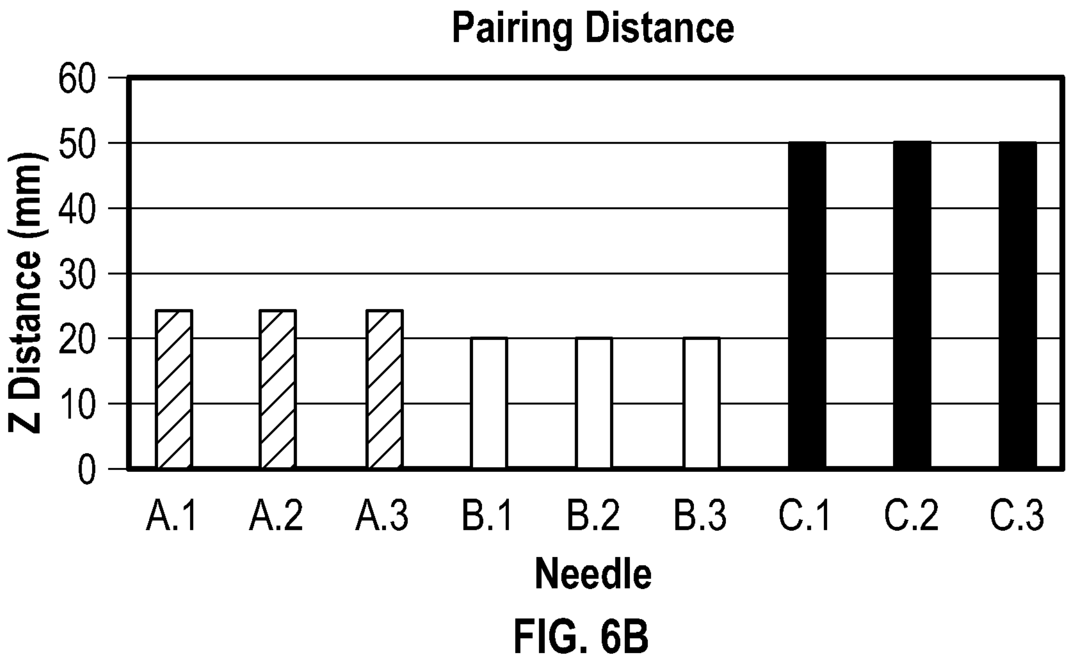
Figure 6C:
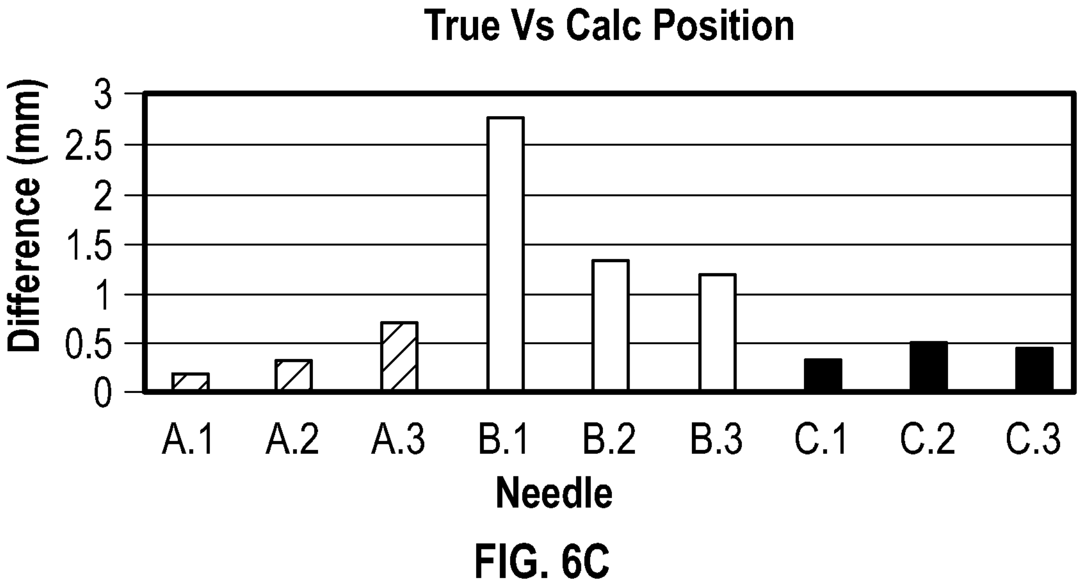
Figure 6D:
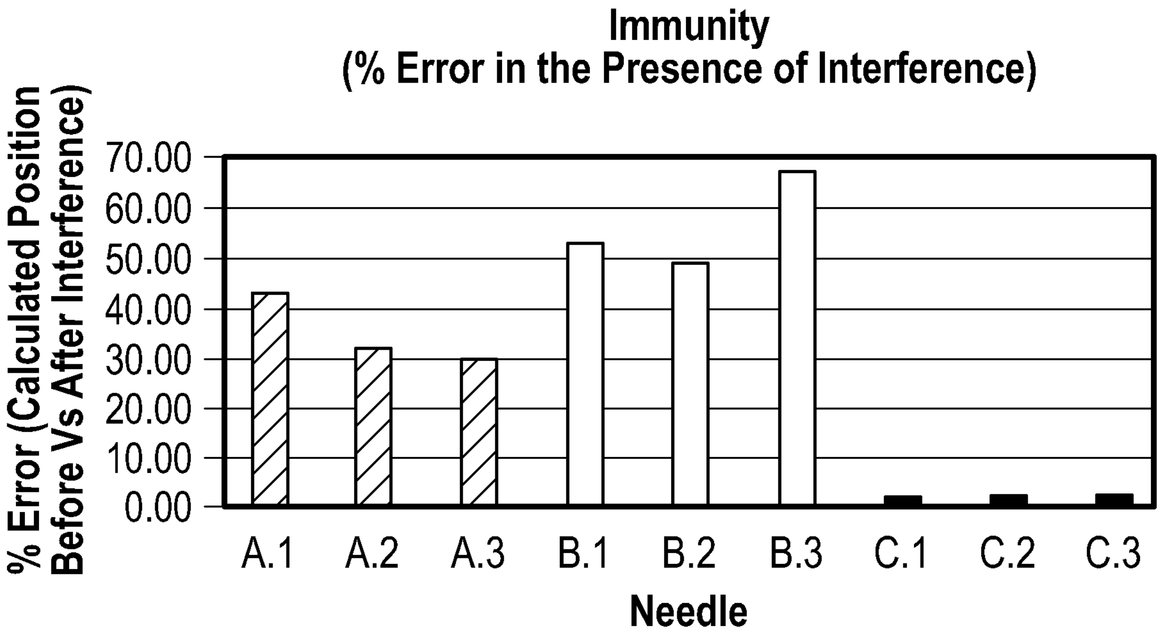

FIGS. 6A-6D show bar charts illustrating the data collected. The data is from a total of 9 total needles with 3 needles of each type, as described herein. FIG. 6A shows the drop-out distance for each needle. FIG. 6B shows the averaged pairing distance for each needle. FIG. 6C shows the difference between the true position and the calculated position for each needle. FIG. 6D shows a percentage change in error in calculated position in the presence of a magnetic interference source. It is important to note that the data presented herein is exemplary only and should not be considered as limiting to the scope of the invention.

Results

Advantageously, it was found that needles formed of 17-7 PH SS, e.g. needle C, displayed a drop out distance and a pairing distance that was substantially double the drop out distance and pairing distance of needles formed of 304 SS, e.g. needle A and needle B. Further, the immunity of the 17-7 PH SS needles, needle C, to an interference source was improved by between 15 to 25 times. As such the calculated position of the needle varied less than 3% in the presence of the magnetic interference source. This compares with a change of between 34% and 57% of the calculated position for the 304 SS needles in the presence of the same magnetic interference source. The results of the exemplary tests are shown below in Table 4:

TABLE 4

Results of the exemplary tests

| Tests | | Needle A | Needle B | Needle C |
|---|---|---|---|---|
| Drop-Out (mm) | | 27.0 | 23.9 | 50.3 |
| Pairing (mm) | | 25.0 | 20.0 | 50.0 |
| Immunity | (mm) | 7.2 | 12.9 | 0.5 |
| | % error | 34.1 | 56.4 | 2.5 |
| True Vs Calc. (mm) | | 0.4 | 1.7 | 0.4 |

Based on these exemplary results, needles formed of 17-7 PH SS outperforms needles formed of 304 stainless steel in the measured aspects of magnetic based tracking. Overall, the needles formed of 17-7 PH SS offer a greater window of use when used with magnetic tracking systems, and are considerably less affected by magnetic interference.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A trackable catheter placement system, comprising:

a needle formed of a magnetizable material and magnetized to produce a magnetic field having one or both of a magnetic field strength and a magnetic field signature detectable by a sensor of a tracking system; and a spring formed of a non-magnetizable material including an alloy having copper and beryllium and configured to display one or both of the same physical dimensions and mechanical performance properties as a spring formed of the magnetizable material.

2. The trackable catheter placement system according to claim 1, wherein the alloy having copper and beryllium includes a silver coated copper beryllium alloy.

3. The trackable catheter placement system according to claim 1, wherein the magnetizable material includes 17-7 precipitation hardened stainless steel.

4. The trackable catheter placement system according to claim 1, wherein the spring includes a wire core diameter of 0.0113±0.001 inches.

5. The trackable catheter placement system according to claim 1, wherein the spring includes between 30 and 37 active coils.

6. The trackable catheter placement system according to claim 1, wherein the spring includes a solid length of between 0.45 inches and 0.49 inches.

7. The trackable catheter placement system according to claim 1, wherein the spring includes a coil pitch angle of between 12 degrees and 16 degrees.

8. The trackable catheter placement system according to claim 1, wherein the spring includes a spring diameter of 0.205±0.005 inches.

9. The trackable catheter placement system according to claim 1, wherein the spring includes 3 dead coils at a distal end and 2 dead coils at a proximal end.

10. The trackable catheter placement system according to claim 1, wherein the spring includes a distal flared diameter of 0.215 inches.

11. The trackable catheter placement system according to claim 1, wherein the tracking system includes a passive magnetic tracking system configured to detect the magnetic field strength of the needle.

12. The trackable catheter placement system according to claim 1, wherein the tracking system includes an electro-magnetic tracking system configured to detect the magnetic field signature of the needle.

13. A method of tracking a catheter placement system, comprising:

providing the catheter placement system comprising:

a needle formed of a magnetizable material; and a spring formed of a non-magnetizable material including an alloy having copper and beryllium and configured to display one or both of the same physical dimensions and mechanical properties as a spring formed of the magnetizable material;

magnetizing the catheter placement system;

producing a magnetic field from the needle, having a magnetic field strength or a magnetic field signature; and detecting the magnetic field by a sensor of a tracking system.

14. The method according to claim 13, wherein the alloy having copper and beryllium includes a silver coated copper beryllium alloy.

15. The method according to claim 13, wherein the magnetizable material includes a ferrous material, steel, stainless steel, 304-stainless steel, or 17-7 precipitation hardened stainless steel.

16. The method according to claim 13, wherein the spring includes a wire core diameter of 0.0113±0.001 inches.

17. The method according to claim 13, wherein the spring includes between 30 and 37 active coils.

18. The method according to claim 13, wherein the spring includes a solid length of between 0.45 inches and 0.49 inches.

19. The method according to claim 13, wherein the spring includes a coil pitch angle of between 12 degrees and 16 degrees.

20. The method according to claim 13, wherein the spring includes a spring diameter of 0.205±0.005 inches.

21. The method according to claim 13, wherein the spring includes 3 dead coils at a distal end and 2 dead coils at a proximal end.

22. The method according to claim 13, wherein the spring includes a distal flared diameter of 0.215 inches.

23. The method according to claim 13, further including determining one of a location, an orientation, or a trajectory of the needle.

24. The method according to claim 13, wherein the tracking system includes a passive magnetic tracking system configured to detect the magnetic field strength of the needle.

25. The method according to claim 13, wherein the tracking system includes an electro-magnetic tracking system configured to detect the magnetic field signature of the needle.

26. A method of manufacturing a trackable medical device, comprising:

providing a medical device including a needle extending from a distal end of a body and a spring disposed within the body, the needle configured to access a vasculature of a patient and formed of one of 304-stainless steel or 17-7 precipitation hardened stainless steel, the spring including copper and beryllium;

placing a portion of the medical device within a magnetizer that includes a magnetic element;

magnetizing the needle and the spring; and providing a first magnetic signal from the needle.

* * * * *